US012708667B2

(12) United States Patent
Gajewski et al.

(10) Patent No.: US 12,708,667 B2
(45) Date of Patent: Aug. 18, 2026

(54) COMPOSITIONS AND METHODS CONCERNING COMBINATIONS OF IMMUNOLOGIC INHIBITORS FOR THE TREATMENT OF CANCER

(71) Applicant: The University of Chicago, Chicago, IL (US)

(72) Inventors: Thomas F. Gajewski, Chicago, IL (US); Stefani Spranger, Chicago, IL (US); Michael Leung, Chicago, IL (US)

(73) Assignee: The University of Chicago, Chicago, IL (US)

( * ) Notice: Subject to any disclaimer, the term of this patent is extended or adjusted under 35 U.S.C. 154(b) by 640 days.

(21) Appl. No.: 17/248,745

(22) Filed: Feb. 5, 2021

(65) Prior Publication Data

US 2021/0228715 A1 Jul. 29, 2021

Related U.S. Application Data

(60) Division of application No. 16/031,650, filed on Jul. 10, 2018, now Pat. No. 10,967,060, which is a continuation of application No. 14/438,310, filed as application No. PCT/US2013/066936 on Oct. 25, 2013, now Pat. No. 10,034,939.

(60) Provisional application No. 61/719,202, filed on Oct. 26, 2012.

(51) Int. Cl.

| | |
|---|---|
| ***A61K 31/4245*** | (2006.01) |
| ***A61K 39/395*** | (2006.01) |
| ***A61K 45/06*** | (2006.01) |
| *A61K 39/00* | (2006.01) |

(52) U.S. Cl.
CPC .... *A61K 39/39558* (2013.01); *A61K 31/4245* (2013.01); *A61K 45/06* (2013.01); *A61K 2039/507* (2013.01)

(58) Field of Classification Search
CPC .......... A61K 31/4245; A61K 2039/507; A61K 39/39541; A61K 39/39558
USPC ...................................................... 424/142.1
See application file for complete search history.

(56) References Cited

U.S. PATENT DOCUMENTS

| | | | |
|---|---|---|---|
| 6,682,736 B1 | 1/2004 | Hanson et al. | |
| 6,984,720 B1 | 1/2006 | Korman et al. | |
| 7,034,121 B2 | 4/2006 | Carreno et al. | |
| 7,109,003 B2 | 9/2006 | Hanson et al. | |
| 7,132,281 B2 | 11/2006 | Hanson et al. | |
| 7,229,628 B1 | 6/2007 | Allison et al. | |
| 7,307,064 B2 | 12/2007 | Rusnak | |
| 7,311,910 B2 | 12/2007 | Linsley et al. | |
| 8,088,803 B2 | 1/2012 | Combs et al. | |
| 9,855,302 B2 | 1/2018 | Gajewski et al. | |
| 9,944,992 B2 | 4/2018 | Zheng et al. | |
| 10,034,939 B2 * | 7/2018 | Gajewski | A61K 45/06 |
| 10,206,871 B2 | 2/2019 | Lin et al. | |
| 10,517,822 B2 | 12/2019 | Lin et al. | |
| 10,753,938 B2 | 8/2020 | Gajewski et al. | |
| 10,780,045 B2 | 9/2020 | Lin et al. | |
| 10,806,694 B2 | 10/2020 | Lin et al. | |
| 10,815,531 B2 | 10/2020 | Zheng et al. | |
| 10,967,060 B2 * | 4/2021 | Gajewski | A61K 39/39558 |
| 11,574,747 B2 * | 2/2023 | Hubbell | G21F 7/005 |
| 2004/0234623 A1 | 11/2004 | Munn et al. | |
| 2006/0258719 A1 | 11/2006 | Combs et al. | |
| 2007/0185165 A1 | 8/2007 | Combs et al. | |
| 2010/0055111 A1 | 3/2010 | Sharma et al. | |
| 2012/0058079 A1 | 3/2012 | Combs et al. | |
| 2015/0307617 A1 | 10/2015 | Du et al. | |
| 2016/0024593 A1 | 1/2016 | Zheng et al. | |
| 2016/0101128 A1 | 4/2016 | Wang et al. | |
| 2016/0108045 A1 | 4/2016 | Andres et al. | |
| 2016/0108123 A1 | 4/2016 | Freeman et al. | |
| 2016/0355597 A1 | 12/2016 | Rhee et al. | |
| 2016/0368994 A1 | 12/2016 | Kelley et al. | |
| 2023/0032934 A1 * | 2/2023 | Langer | A61K 39/0011 |
| 2023/0377764 A1 * | 11/2023 | Hubbell | C07K 14/522 |
| 2024/0156911 A1 * | 5/2024 | Wittrup | A61K 38/2013 |

FOREIGN PATENT DOCUMENTS

| | | |
|---|---|---|
| WO | WO 9929310 | 6/1999 |
| WO | WO 03087347 | 10/2003 |
| WO | WO 2004094409 | 11/2004 |
| WO | WO 200713648 | 10/2007 |
| WO | WO 2011100295 | 8/2011 |
| WO | WO 2015119944 | 8/2015 |
| WO | 2021108727 * | 6/2021 |

OTHER PUBLICATIONS

Tang et al (J Hematol Oncol 14:68 (2021)).*
Fujiwara et al (Cancer Treatment Reviews 110:102461; (Nov. 2022)).*
Jiang et al (Aging 12(12):11349 (Jun. 22, 2020)).*
Guo et al (Acta Pharmacol Sin. 41(3): 423-431 (Mar. 2020)).*
Ai et al (Drug Design, Development and Therapy 2020:14 3625-3649).*
Liu et al (Frontiers in Pharmacol 12:731798 (Sep. 1, 2021).*
Acurcio et al (J Immunother Cancer 2022;10:e004695.*
Deshmukh (J Cancer Immunol. 2020 vol. 2, Issue 1:10-12).*
Chang et al (The Oncologist 2021;26:e1786-e1799).*
Rowshanravan et al (Blood Jan. 4, 2018 | vol. 131, No. 1:58-67).*
De Corte et al (epi Information | "Assessment of Assertions of (Continued)

*Primary Examiner* — Lynn A Bristol
(74) *Attorney, Agent, or Firm* — Norton Rose Fulbright US LLP

(57) ABSTRACT

Aspects herein relate to combinations of inhibitors useful in the treatment of cancer, and methods of treating cancer using such combinations. In some embodiments, the methods involve the use of a combination of at least two of the following: an inhibitor of indoleamine-2,3-dioxygenase (IDO), an inhibitor of the PD-L1/PD-1 pathway, an inhibitor of CTLA-4, an inhibitor of CD25, or IL-7.

18 Claims, 19 Drawing Sheets

(56) References Cited

OTHER PUBLICATIONS

Synergy as a Basis for Inventive Step in Compositions Comprising Mixtures" 1: 1-12 , Feb. 2019).*
Feng et al (Antibody Therapeutics, 2020, vol. 3, No. 4 265-270; Publication on Dec. 3, 2020).*
Clinicaltrials.gov (Incyte; NCT01604889); May 24, 2012).*
Charehjoo et al (International Immunopharmacology vol. 118, May 2023, 110032).*
Affolter et al (PLoS One May 21, 2019;14(5):e0217276. doi: 10.1371/journal.pone.0217276. eCollection 2019).*
Fujiwara et al (Cancer Treat Rev Nov. 2022;110:102461. doi: 10.1016/j.ctrv.2022.102461. Epub Aug. 30, 2022).*
Gibney et al. Journal for Immuno Therapy of Cancer (2019) 7:80.*
ATTC "UC10-4F10-1" Hybridoma Product Data Sheet pp. 1-6; Dec. 16, 2024.*
Blank et al., "PD-L1/B7H-1 Inhibits the Effector Phase of Tumor Rejection by T Cell Receptor (TCR) Transgenic CD8+ T Cells," *Cancer Res*., 64:1140-1145, 2004.
Brown et al., "Homeostatic Proliferation as an Isolated Variable Reverses CD8+ T Cell Anergy and Promotes Tumor Rejection," *J Immunol*. 177:4521-4529, 2006.
ClinicalTrials.gov (NCT02318277; "A Study of Epacadostat (INCB024360) in Combination with Durvakumab (MEDI4736) in Subjects with Selected Advanced Solid Tumors (ECHO-203)"; pp. 1-6; Aug. 28, 2017.
Curran et al., *PNAS* 107(9):4275-4280, 2010.
Däubener, et al., "Activated Indoleamine 2,3-Dioxygenase Activity in Human Cells is an Antiparasitic and an Antibacterial Effector Mechanism," *Adv. Exp. Med. Biol*., 467: 517-24, 1999.
Elpek et al., "CD4+CD25+ T Regulatory Cells Dominate Multiple Immune Evasion Mechanisms in Early but Not Late Phases of Tumor Development in a B Cell Lymphoma Model," *The Journal of Immunology*, 178: 6840-6848, 2007.
Gajewski et al., "Gene Signature in Melanoma Associated With Clinical Activity: A Potential Clue to Unlock Cancer Immunotherapy," *Cancer J*., 16:399-403, 2010.
Gajewski et al., "Immune resistance orchestrated by the tumor microenvironment," *Immunol. Rev*., 213:131-145, 2006.
Gajewski, et al., "Immune Suppression in the Tumor Microenvironment," *Journal of Immunotherapy*, 29(3); 233-240, 2006.
Grohmann, et al., "Tolerance, DCs and tryptophan: much ado about IDO," *Trends Immunol*., 24: 242-8, 2003.
Harlin et al., "Chemokine Expression in Melanoma Metastases Associated with CD8+ T-Cell Recruitment," *Cancer Res*., 69(7):3077-85, 2009.
Harlin et al., "Tumor progression despite massive influx of activated CD8+ T cells in a patient with malignant melanoma ascites," *Cancer Immunol. Immunother*., 55:1185-1197, 2006.
Ibrahim, et al., "PD-L1 Blockade for Cancer Treatment: MEDI4736," *Seminars in Oncology*, 42(3); pp. 474-483, 2015.
International Search Report and Written Opinion for PCT/US2013/066936, mailed Mar. 3, 2014.
Kline et al., "Homeostatic Proliferation Plus Regulatory T-Cell Depletion Promotes Potent Rejection of B16 Melanoma," *Clin. Cancer Res*. 14:3156-3167, 2008.
Logan, et al., "HeLa cells cocultured with peripheral blood lymphocytes acquire an immuno-inhibitory phenotype through upregulation of indoleamine 2,3-dioxygenase activity," *Immunology*, 105: 478-87, 2002.
Muller et al., "Inhibition of indoleamine 2,3-dioxygenase, an immunoregulatory target of the cancer suppression gene Bin1, potentiates cancer chemotherapy," *Nature Med*., 11: 312-319, 2005.
Munn, et al., "Expression of indoleamine 2,3-dioxygenase by plasmacytoid dendritic cells in tumor-draining lymph nodes," *J. Clin. Invest*., 114(2): 280-90, 2004.
Munn, et al., "Inhibition of T Cell Proliferation by Macrophage Tryptophan Catabolism" *J Exp Med*, 189(9):1363-72, 1999.
Munn, et al., "Macrophages and the Regulation of Self-Reactive T Cells," *Curr Pharm Des*, 9(3):257-264, 2003.
Munn, et al., "Potential Regulatory Function of Human Dendritic Cells Expressing Indoleamine 2,3-Dioxygenase," *Science*, 297: 1867-70, 2002.
Partial Supplementary European Search Report for EP13849295.4, mailed Jun. 17, 2016.
Quezada et al., "CTLA4 blockade and GM-CSF combination immunotherapy alters the intratumor balance of effector and regulatory T cells," *J Clin. Invest*., 116: 1935-1945, 2006.
Sharma, et al., Plasmacytoid Dendritic Cells from Mouse Tumor-Draining Lymph Nodes Directly Active Mature Tregs via Indoleamine 2,3-Dioxygenase, *Journal of Clinical Investigation*, 117(9); 2570-2582, 2007.
Spranger, et al., "Mechanism of Tumor Rejection with Doublets of CTLA-4, PD-1/PD- L1, or IDO Blockade Involves Restored IL-2 Production and Proliferation of CD8+ Cells Directly Within the Tumor Microenvironment," *Journal of Immunotherapy*, 2(3): 1-14, 2014.
Spranger, et al., "Up-Regulation of PD-L1, IDO, and Tregs in the Melanoma Tumor Microenvironment is Driven by CD8+ T Cells," *Science Translational Medicine*, 5(200): 200, 2013.
Stewart et al., "Identification and Characterization of MEDI4736, an Antagonistic Anti-PD-L1 Monoclonal Antibody," *Cancer Immunology Research*, 3(9): 1052-1062, 2015.
Sweis, et al., Molecular Drivers of the Non-T-Cell-Inflamed Tumor Microenvironment in Urothelial Bladder Cancer, Cancer Immunology Research, 4(7): 563-568, 2016.
Taylor, et al., "Relationship between interferon-gamma, indoleamine 2,3-dioxygenase, and tryptophan catabolism" *FASEB J*., 5: 2516-22, 1991.
Uyttenhove et al., "Evidence for a tumoral immune resistance mechanism based on tryptophan degradation by indoleamine 2,3-dioxygenase," *Nature Med*., 9: 1269-74, 2003.
Wainwright et al., "Durable Therapeutic Efficacy Utilizing Combinatorial Blockade against IDO, CTLA-4, and PD-L1 in Mice with Brain Tumors" *Clin Cancer Res*. 2014, 20(20), 5290-5301.
Wirleitner, et al., "Interferon-γ-Induced Conversion of Tryptophan: Immunologic and Neuropsychiatric Aspects," *Curr. Med. Chem*., 10: 1581-91, 2003.
Zha et al., "T cell anergy is reversed by active Ras and is regulated by diacylglycerol kinase-α," *Nat. Immunol*. 7:1166-1173, 2006.
Zhang et al., "PD-1/PD-L1 interactions inhibit antitumor immune responses in a murine acute myeloid leukemia model," *Blood*, 114:1545-1552, 2009.

* cited by examiner

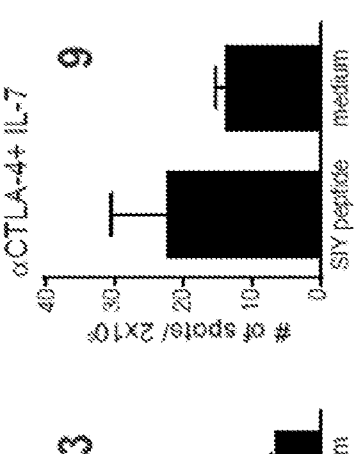
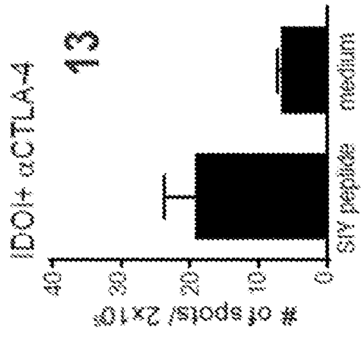
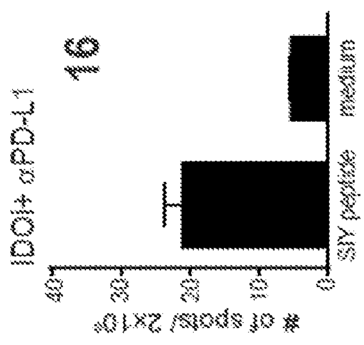
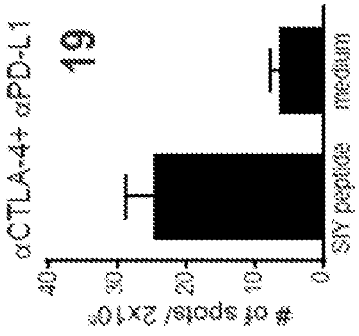
FIG. 7

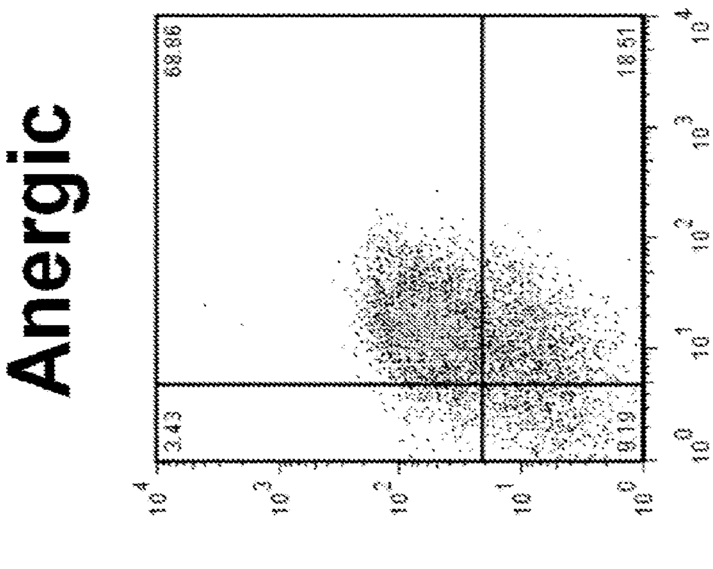
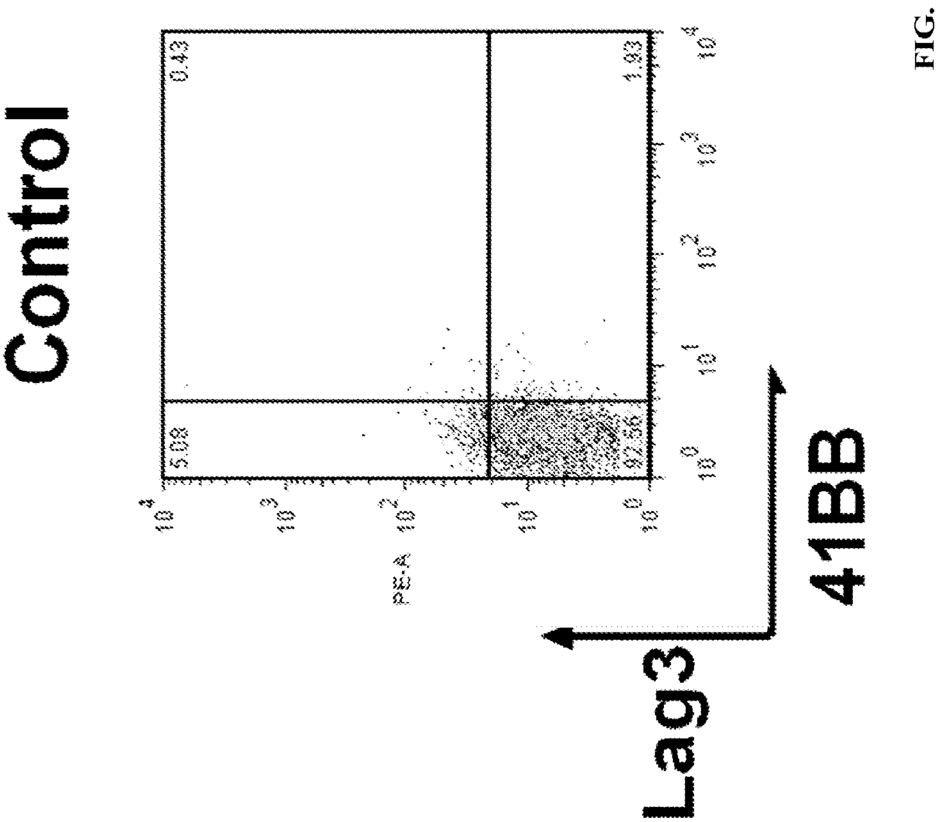
FIG. 8

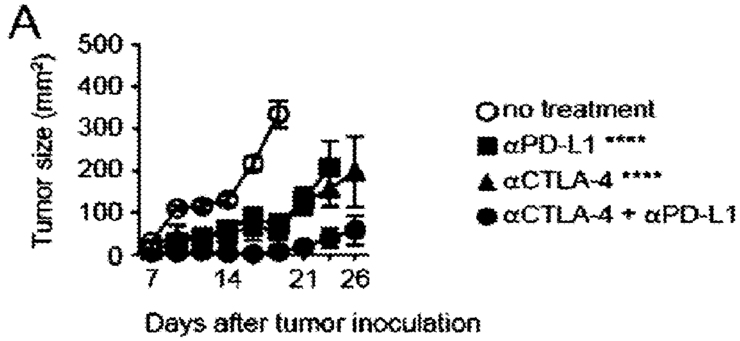
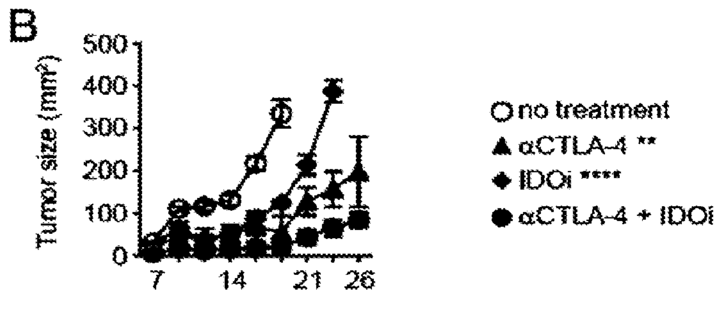
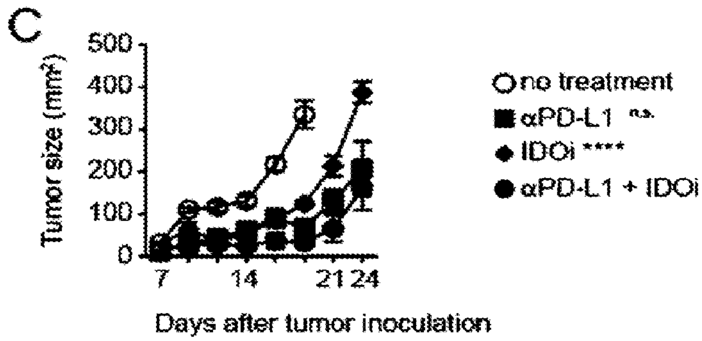
FIGS. 9A-C

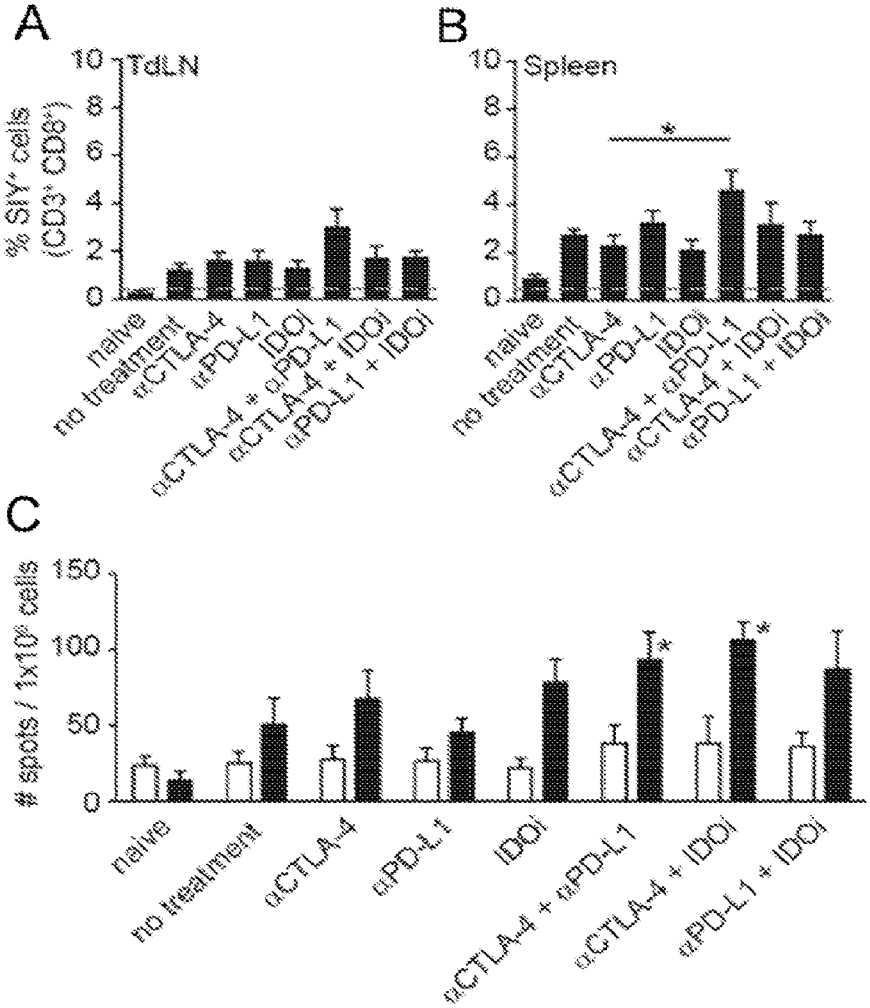
FIGS. 10A-C

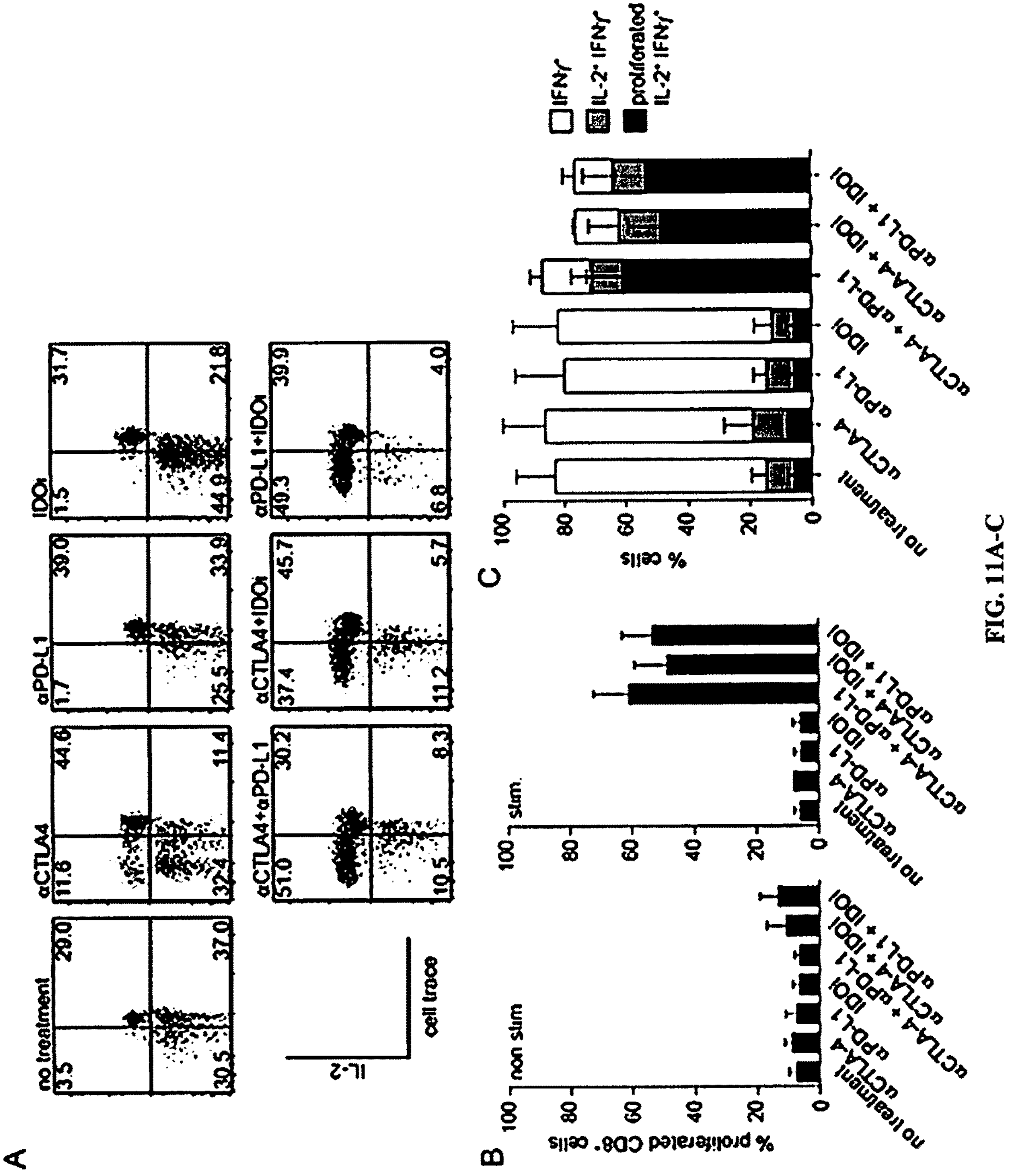
FIG. 11A-C

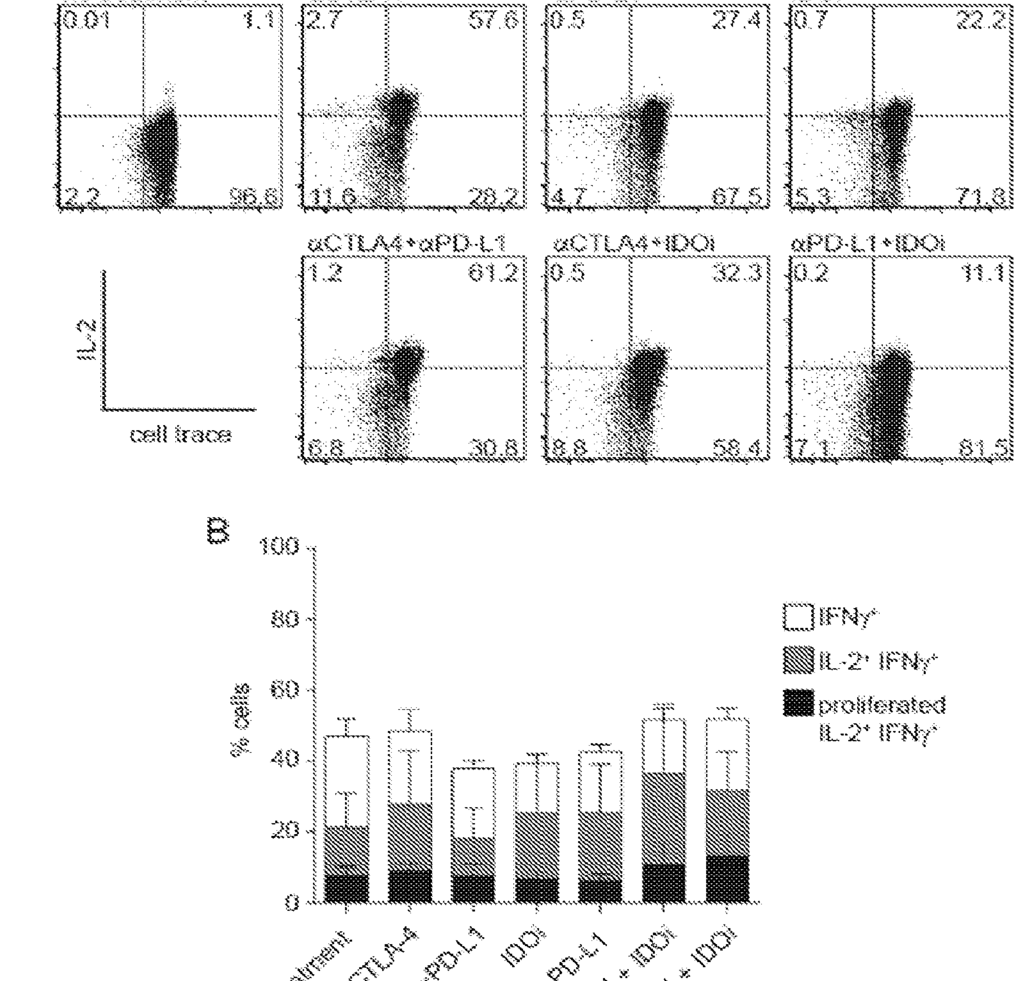
FIGS. 12A-B

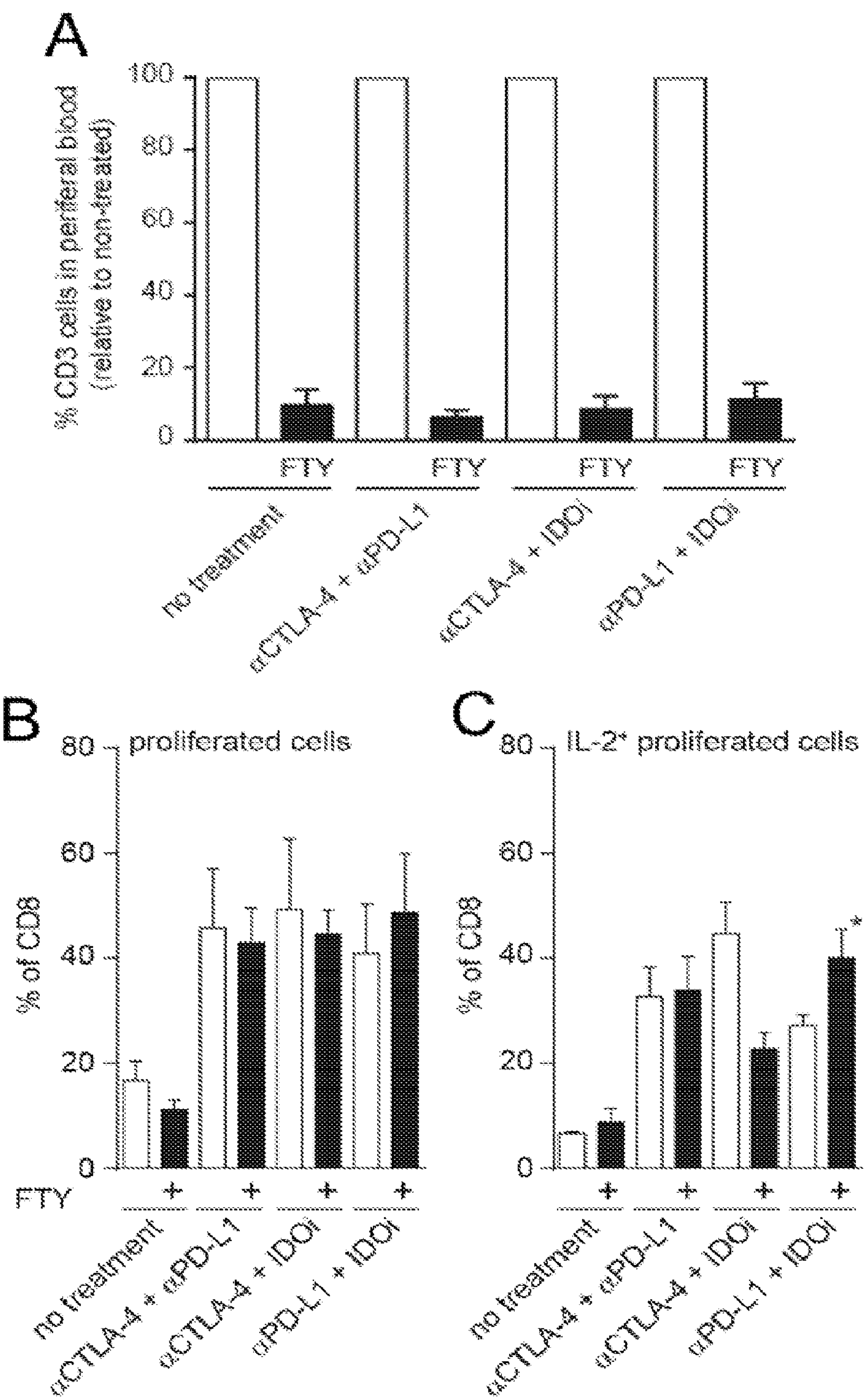
FIGS. 13A-C

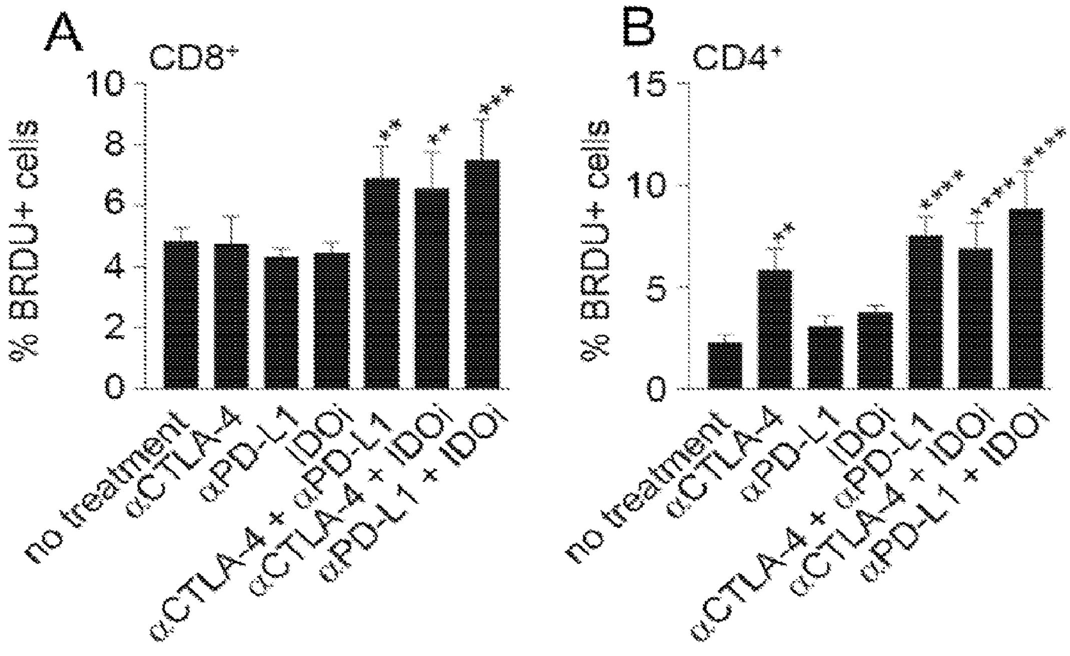
FIGS. 14A-B

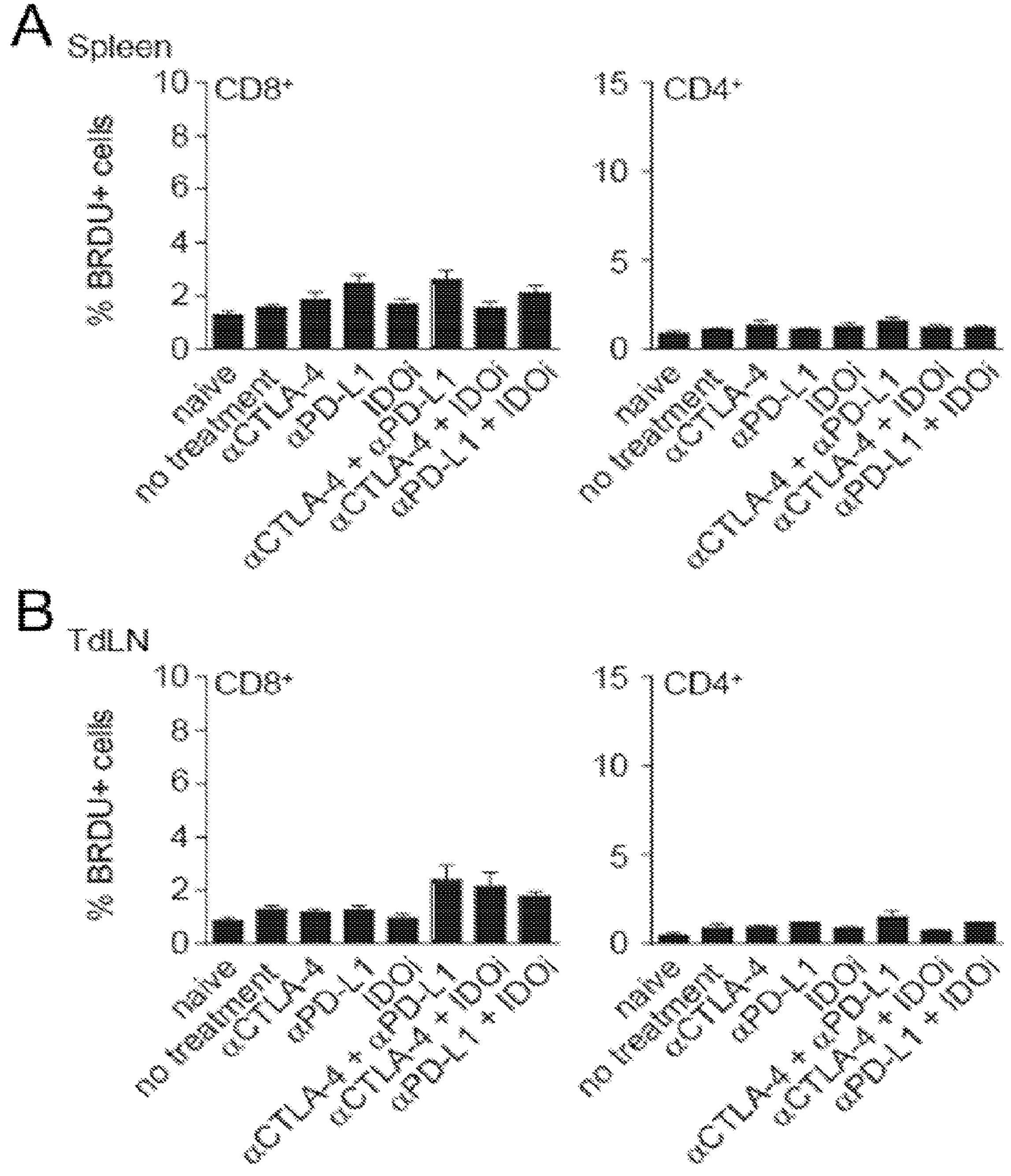
FIGS. 15A-B

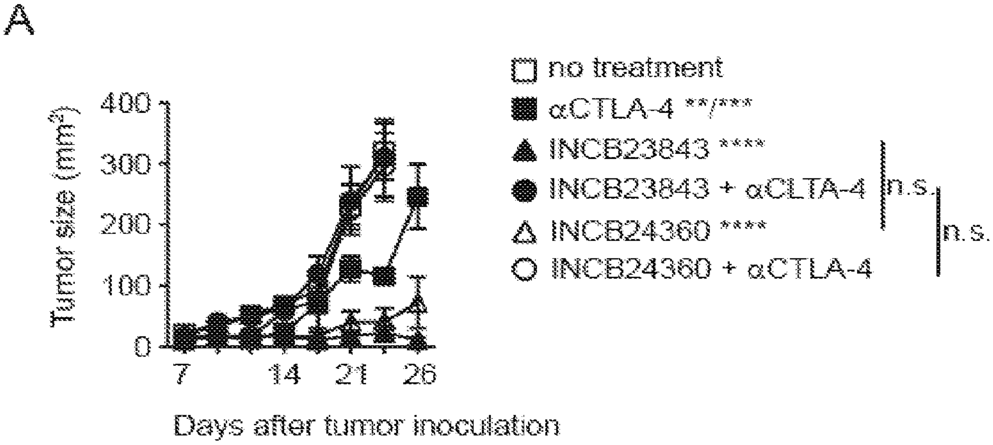
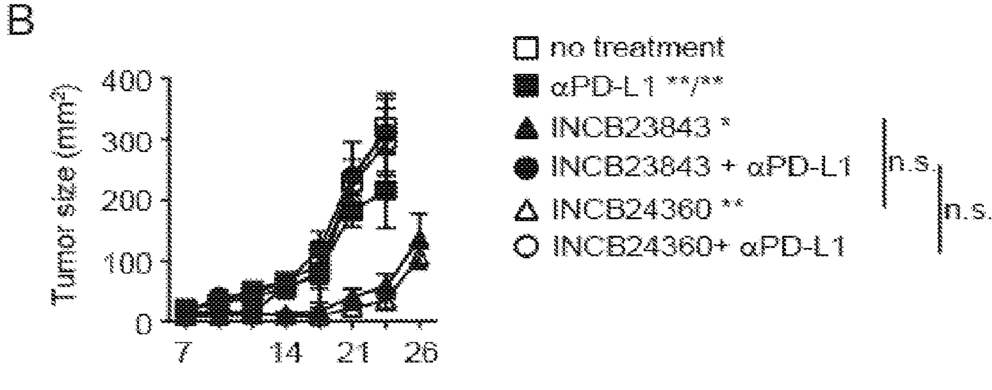
FIGS. 18A-B

COMPOSITIONS AND METHODS CONCERNING COMBINATIONS OF IMMUNOLOGIC INHIBITORS FOR THE TREATMENT OF CANCER

CROSS-REFERENCE TO RELATED APPLICATION

This application is a divisional of U.S. patent application Ser. No. 16/031,650 filed Jul. 10, 2018, which is a continuation of U.S. patent application Ser. No. 14/438,310 filed Apr. 24, 2015, which is a national phase application under 35 U.S.C. § 371 of International Application No. PCT/US2013/066936 filed Oct. 25, 2013, which claims the benefit of priority to U.S. Provisional Patent Application Ser. No. 61/719,202, filed Oct. 26, 2012. The entire contents of each of the above-referenced disclosures are specifically incorporated herein by reference.

BACKGROUND OF THE INVENTION

I. Field of the Invention

Embodiments of this invention are directed generally to microbiology and medicine. In certain aspects the invention is directed to treatment of cancer.

II. Description of the Related Art

Over the last two decades, numerous mechanisms have been identified that contribute to immune suppression in the context of a growing tumor. Recent work has suggested that failed immune-mediated tumor rejection is attributable to the dominant inhibitory effect of immune suppressive mechanisms that largely act at the level of the tumor microenvironment. At least 4 such mechanisms appear to be operative in individual tumors: ligation of PD-1 on T cells by PD-L1 expressed by tumor cells, extrinsic suppression by regulatory T cells (Tregs), classical T cell anergy, and tryptophan catabolism by indoleamine-2,3-dioxygenase (IDO). Preclinical studies have revealed that manipulation each of these pathways individually can have a positive effect on anti-tumor immunity.

Data also suggest that Treg cells may serve as an important therapeutic target for patients with early stages of cancer and that more vigorous combinatorial approaches simultaneously targeting multiple immune evasion as well as immunosurveillance mechanisms for the generation of a productive immune response against tumor may be required for effective immunotherapy in patients with advanced disease (Elpek et al., 2007).

The first therapeutic approach to reach clinical practice is the blockade of CTLA-4 using the anti-CTLA-4 mAb ipilimumab. Despite this therapeutic advance, this regimen is effective in only a minority of patients, and therefore further treatment developments are required. Preclinical studies have revealed that manipulation each of these pathways individually can have a positive effect on anti-tumor immunity. However, as the tumor microenvironment appears to involve the complex interplay between multiple pathways together, it may be necessary to block 2 or more immune suppressive mechanisms in concert in order to achieve a maximal therapeutic effect. In addition, other immunomodulatory pathways appear to be operational outside the tumor microenvironment in secondary lymphoid structures-one such regulatory molecule is CTLA-4, and the anti-CTLA-4 mAb ipilimumab was recently approved for treatment of patients with metastatic melanoma. Simultaneous manipulation of pairs of immune regulatory pathways together may yield synergistic effects on the anti-tumor immune response, thus translating into improved tumor control in vivo.

SUMMARY OF THE INVENTION

In some aspects, there are methods of treating cancer in a subject comprising administering to the subject an effective amount of at least two of the following: an inhibitor of indoleamine-2,3-dioxygenase (IDO), an inhibitor of the PD-L1/PD-1 pathway, an inhibitor of CTLA-4, an inhibitor of CD25, or IL-7. Any combination of at least two of the following: an inhibitor of indoleamine-2,3-dioxygenase (IDO), an inhibitor of the PD-L1/PD-1 pathway, an inhibitor of CTLA-4, an inhibitor of CD25, or IL-7 may be used. In some embodiments, the method may comprise the use of two or more inhibitors. In some embodiments, the method may comprise the use of three or more inhibitors. In some embodiments, the method may comprise the use of four or more inhibitors. In some embodiments, the method may comprise the use of five or more inhibitors. In some embodiments, the method comprises administering an inhibitor of IDO and an inhibitor of CTLA-4. In some embodiments, the method comprises administering an inhibitor of IDO and an inhibitor of the PD-L1/PD-1 pathway. In some embodiments, the method comprises administering an inhibitor of IDO, an inhibitor of the PD-L1/PD-1 pathway, and an inhibitor of CTLA-4. In some embodiments, the method comprises administering an inhibitor of the PD-L1/PD-1 pathway and an inhibitor of CTLA-4.

The IDO inhibitor may be any effective IDO inhibitor. In some embodiments, the inhibitor of IDO is a compound of Formula I:

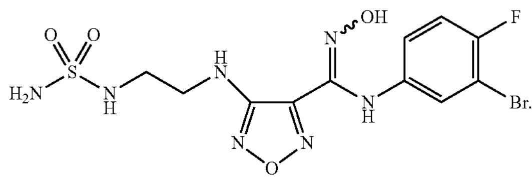 [SMILES: NS(=O)(=O)NCCNc1nonc1C(=NO)Nc1ccc(F)c(Br)c1]

or a pharmaceutically acceptable salt thereof, wherein $R^1$ is $NH_2$ or $CH_3$, $R^2$ is Cl, F, $CF_3$, $CH_3$, Br, or CN, $R^3$ is H or F, $R^4$ is H or $CH_3$, and, n is 1 or 2. In some embodiments, the inhibitor of IDO is the compound of:

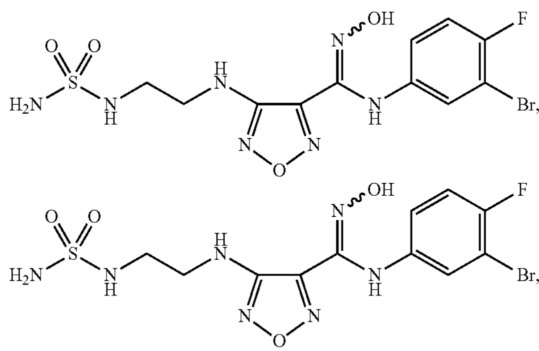

-continued

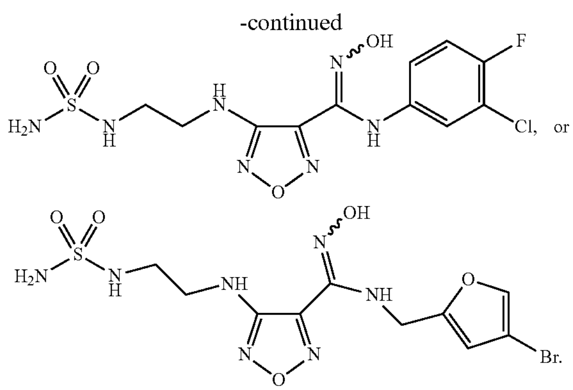

or

The inhibitor of the PD-L1/PD-1 pathway may be any effective inhibitor of the PD-L1/PD-1 pathway. In some embodiments, the inhibitor of the PD-L1/PD-1 pathway is an anti-PD-L1 antibody or an anti-PD-1 antibody. In some embodiments, the anti-PD-L1 or anti-PD-1 antibody is a monoclonal antibody. In some embodiments, the monoclonal antibody is a human antibody. In some embodiments, the anti-PD-L1 or anti-PD-1 antibody is a humanized antibody. In some embodiments, the anti-PD-L1 monoclonal antibody is BMS-936559, MIPDL3280A, BMS-936558, MK-3475, CT-011, or MEDI4736.

The inhibitor of CTLA-4 may be any effective inhibitor of CTLA-4. In some embodiments, the inhibitor of CTLA-4 is an anti-CTLA-4 antibody. In some embodiments, the anti-CTLA-4 antibody is a monoclonal antibody. In some embodiments, the anti-CTLA-4 antibody monoclonal antibody is a human antibody. In some embodiments, the anti-CTLA-4 antibody is a humanized antibody. In some embodiments, the anti-CTLA-4 monoclonal antibody is ipilimumab.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease. In some embodiments, treating cancer is further defined as reducing the size of a tumor or inhibiting growth of a tumor.

The compounds may be administered by any acceptable route. In some embodiments, the compounds are administered orally, intraadiposally, intraarterially, intraarticularly, intracranially, intradermally, intralesionally, intramuscularly, intranasally, intraocularally, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, orally, parenterally, rectally, subconjunctival, subcutaneously, sublingually, topically, transbuccally, transdermally, vaginally, in cremes, in lipid compositions, via a catheter, via a lavage, via continuous infusion, via infusion, via inhalation, via injection, via local delivery, via localized perfusion, bathing target cells directly, or any combination thereof. In specific embodiments, the inhibitor ipilimumab is administered intravenously.

A dose may be administered on an as needed basis or every 1, 2, 3, 4, 5, 6, 7, 8, 9, 10, 11, 12, 18, or 24 hours (or any range derivable therein) or 1, 2, 3, 4, 5, 6, 7, 8, 9, or times per day (or any range derivable therein). A dose may be first administered before or after signs of an infection are exhibited or felt by a patient or after a clinician evaluates the patient for an infection. In some embodiments, the patient is administered a first dose of a regimen 1, 2, 3, 4, 5, 6, 7, 8, 9, 10, 11, 12 hours (or any range derivable therein) or 1, 2, 3, 4, or 5 days after the patient experiences or exhibits signs or symptoms of an infection (or any range derivable therein). The patient may be treated for 1, 2, 3, 4, 5, 6, 7, 8, 9, 10 or more days (or any range derivable therein) or until symptoms of an infection have disappeared or been reduced or after 6, 12, 18, or 24 hours or 1, 2, 3, 4, or 5 days after symptoms of an infection have disappeared or been reduced. In specific embodiments, the inhibitor ipilimumab is administered every three weeks.

The at least two inhibitors may be in a single composition or may be in separate compositions. If the inhibitors are in separate compositions, they may be administered simultaneously or with a delay between administrations. In some embodiments, second or subsequent inhibitors may be administered 1, 2, 3, 4, 5, 6, 7, 8, 9, 10, 15, 20, 25, 30, 40, 50, or 60 minutes or longer (or any range derivable therein) after the first inhibitor is administered. In some embodiments, second or subsequent inhibitors may be administered 1, 2, 3, 4, 5, 6, 7, 8, 9, 10, 15, 20, or 24 hours or longer (or any range derivable therein) after the first inhibitor is administered. In some embodiments, subsequent inhibitors may be administered 1, 2, 3, 4, 5, 6, 7, 8, 9, 10, 15, 20, or 30 days or longer (or any range derivable therein) after the first inhibitor is administered. In some embodiments, subsequent inhibitors may be administered 1, 2, 3, 4, 5, 6, 7, 8, 9, 10, 15, 20, 25, 30, 40, or 50 weeks or longer (or any range derivable therein) after the first inhibitor is administered. In some embodiments, subsequent inhibitors may be administered 1, 2, 3, 4, 5, 6, 7, 8, 9, or 10 years or longer (or any range derivable therein) after the first inhibitor is administered. In some embodiments, the first inhibitor is an inhibitor of IDO and the second inhibitor is an inhibitor of the PD-L1/PD-1 pathway. In some embodiments, the first inhibitor is an inhibitor of IDO and the second inhibitor is an inhibitor of CTLA-4. In some embodiments, the first inhibitor is an inhibitor of the PD-L1/PD-1 pathway and the second inhibitor is an inhibitor of IDO. In some embodiments, the first inhibitor is an inhibitor of the PD-L1/PD-1 pathway and the second inhibitor is an inhibitor of CTLA-4. In some embodiments, the first inhibitor is an inhibitor of CTLA-4 and the second inhibitor is an inhibitor of the PD-L1/PD-1 pathway. In some embodiments, the first inhibitor is an inhibitor of CTLA-4 and the second inhibitor is an inhibitor of IDO.

The cancer may be any cancer. In some embodiments, the cancer is melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplastic syndrome, multiple myeloma, transitional cell carcinoma, neuroblastoma, plasma cell neoplasms, Wilm's tumor, glioblastoma, retinoblastoma, or hepatocellular carcinoma. In some embodiments, the cancer is melanoma.

The compositions may be administered one or more times. In some embodiments, the compositions are administered 1, 2, 3, 4, 5, 6, 7, 8, 9, or 10 times or more. In specific embodiments, the inhibitor ipilimumab is administered 4 times.

Methods may be used in combination with additional cancer therapy. In some embodiments, the distinct cancer therapy comprises surgery, radiotherapy, chemotherapy, toxin therapy, immunotherapy, cryotherapy or gene therapy. In some embodiments, the cancer is a chemotherapy-resistant or radio-resistant cancer.

In some aspects, provided herein are methods of monitoring the patient's response to the treatments disclosed herein. In particular embodiments, disclosed are methods for monitoring the treatment of cancer by any of the methods disclosed herein comprising determining the level of IL-2 in a first sample from the subject, determining the level of IL-2 in a second sample from the subject, and comparing the level of IL-2 in the first sample to the level of IL-2 in the second sample, wherein a level of IL-2 in the second sample that is greater than the level of IL-2 in the first sample indicates that the patient is responding to the treatment. The first sample may be obtained at any time before or after treatment begins. In some embodiments, the first sample is obtained before treatment begins. In some embodiments, the first sample is obtained at the time treatment begins. In some embodiments, the first sample is obtained after treatment is administered. The second sample may be obtained at any time after treatment is administered. In some embodiments, the second sample is obtained 1, 2, 3, 4, 5, 6, 7, or more days, 1, 2, 3, 4, or more weeks, 1, 2, 3, 4, 5, 6, 7, 8, 9, 10, 11, 12 or more months after treatment begins. In some embodiments, the second sample is obtained three days after treatment is administered. In some embodiments, samples may be obtained from several tumor sites.

"Effective amount" or "therapeutically effective amount" or "pharmaceutically effective amount" means that amount which, when administered to a subject or patient for treating a disease, is sufficient to effect such treatment for the disease. In some embodiments, the subject is administered at least about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 20, 30, 40, 50, 60, 70, 80, 90, or 100 mg/kg (or any range derivable therein). In specific embodiments, 50 mg/10 mL (5 mg/mL) of the inhibitor ipilimumab is administered. In specific embodiments, 200 mg/40 mL (5 mg/mL) of the inhibitor ipilimumab is administered.

In other aspects, embodiments provide compositions comprising at least two of the following: an inhibitor of indoleamine-2,3-dioxygenase (IDO), an inhibitor of the PD-L1/PD-1 pathway, an inhibitor of CTLA-4, an inhibitor of CD25, or IL-7. In some embodiments, the composition comprises an inhibitor of IDO and an inhibitor of CTLA-4. In some embodiments, the composition comprises an inhibitor of IDO and an inhibitor of the PD-L1/PD-1 pathway. In some embodiments, the composition comprises an inhibitor of IDO, an inhibitor of the PD-L1/PD-1 pathway, and an inhibitor of CTLA-4. In some embodiments, the composition comprises an inhibitor of the PD-L1/PD-1 pathway and an inhibitor of CTLA-4. It is contemplated that compositions may be pharmaceutical compositions or may be pharmaceutically acceptable compositions.

As used herein, "hydrogen" means —H; "hydroxy" means —OH; "oxo" means =O; "halo" means independently —F, —Cl, —Br or —I; "amino" means $—NH_2$ (see below for definitions of groups containing the term amino, e.g., alkylamino); "hydroxyamino" means —NHOH; "nitro" means $—NO_2$; imino means =NH (see below for definitions of groups containing the term imino, e.g., alkylamino); "cyano" means —CN; "azido" means $—N_3$; "mercapto" means —SH; "thio" means =S; "sulfonamido" means $—NHS(O)_2—$ (see below for definitions of groups containing the term sulfonamido, e.g., alkylsulfonamido); "sulfonyl" means $—S(O)_2—$ (see below for definitions of groups containing the term sulfonyl, e.g., alkylsulfonyl); and "silyl" means $—SiH_3$ (see below for definitions of group(s) containing the term silyl, e.g., alkylsilyl).

For the groups below, the following parenthetical subscripts further define the groups as follows: "(Cn)" defines the exact number (n) of carbon atoms in the group; "(C≤n)" defines the maximum number (n) of carbon atoms that can be in the group; (Cn-n') defines both the minimum (n) and maximum number (n') of carbon atoms in the group. For example, "$alkoxy_{(C≤10)}$" designates those alkoxy groups having from 1 to 10 carbon atoms (e.g., 1, 2, 3, 4, 5, 6, 7, 8, 9, or 10, or any range derivable therein (e.g., 3-10 carbon atoms)). Similarly, "$alkyl_{(C2-10)}$" designates those alkyl groups having from 2 to 10 carbon atoms (e.g., 2, 3, 4, 5, 6, 7, 8, 9, or 10, or any range derivable therein (e.g., 3-10 carbon atoms)).

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$. Similarly, it is contemplated that one or more carbon atom(s) of a compound described herein may be replaced by a silicon atom(s). Further, it is contemplated that any oxygen atom discussed in any compound herein may be replaced by a sulfur or selenium atom.

Any undefined valency on an atom of a structure shown in this application implicitly represents a hydrogen atom bonded to the atom.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dehydrate) water molecules associated with each compound molecule, such as in solid forms of the compound.

As used herein, the term "$IC_{50}$" refers to an inhibitory dose which is 50% of the maximum response obtained.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dogs, cat, mouse, rat, guinea pig, or transgenic species thereof. In certain embodiments, the patient or subject is a primate. Non-limiting examples of human subjects are adults, juveniles, infants and fetuses.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds that are pharmaceutically acceptable, as defined above, and that possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of described embodiments is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002), "Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject of patient which may be at risk and/or predisposed to the disease but does not yet experience or display any or all of the pathology or symptomatology of the disease.

"Prodrug" means a compound that is convertible in vivo metabolically into an inhibitor according to embodiments described herein. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers.

As used herein, the term "water soluble" means that the compound dissolves in water at least to the extent of 0.010 mole/liter or is classified as soluble according to literature precedence.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 7 illustrates the impact on T cell function. IFN-γ ELISpot was performed using splenocytes from day 35 or earlier. $2\times10^6$ splenocytes were cultured for 24 h with or w/o SIY peptide. Depicted are means (+/−SEM) of 4 mice. The red number indicates the number of spots relative to non-stimulated control and two representative examples are displayed.

FIG. 8 illustrates expression of LAG-3 and 4-1BB on anergic T cells as assessed by flow cytometry.

FIGS. 9A-C illustrate tumor outgrowth in response to single and pairwise combinations of αCTLA-4, αPD-L1 and IDOi. Tumor outgrowth measured in $mm^2$ comparing single treatment to the respective combined double treatment of αCTLA-4 and αPD-L1 C (A), αCTLA-4 and IDOi (B), and αPD-L1 and IDOi (C).

FIGS. 10A-C depicts the incidence of tumor-reactive, SIY-specific $CD8^+$ T cells in the tumor-draining lymph node (TdLN) and in the spleen. Peptide/$K^b$ pentamer staining was performed on gated CD3+CD8+ T cells, isolated from TdLN (A) or spleen (B). (C) The functional capacity of these cells was further assessed by IFN-γ ELISpot.

FIGS. 11A-C illustrates double treatments restore capacity of lymphocytes within the tumor to produce IL-2 and proliferate. (A) A representative FACS plot showing proliferation via cell trace dilution on the x-axis and intracellular IL-2 staining on the y-axis. (B) Double treatments show a significant increase in proliferation compared to non-stimulated and single treatments when tested with a one-way Anova. (C) The percentages of IFN-$\gamma^+$ (open bar), IFN-$\gamma^+$ and IL-$2^+$ (gray bar), and proliferating IFN-$\gamma^+$IL-$2^+$ cells (filled bar) were calculated within the $CD3^+CD8^+$ cell population.

FIGS. 12A-B are the non-stimulated controls corresponding to FIGS. 11 (A) and (C).

FIGS. 13A-C demonstrates restoration of IL-2 production and proliferation of tumor-infiltrating lymphocytes in the absence of new T cell migration. (A) B16-SIY bearing mice were either treated with FTY720 or control vehicle prior to initiation of therapy, to prevent migration of new lymphocytes into the tumor. Peripheral blood T cell numbers following FTY720 treatment on the day of tumor harvest for analysis. Open bars depict the number of $CD45^+CD3^+$ T cells detected in 200 ul peripheral blood of vehicle treated mice set to 100%. Filled bars represent the number found in FTY720-treated mice, relative to the vehicle-treated group. Single cell suspensions from tumor were labeled with cell trace and stimulated with plate-bound anti-CD3 antibody for 48 h prior then with anti-CD3 and anti-CD28 in the presence of Brefeldin A. Cells were then analyzed for proliferation by cell trace dilution and production of IL-2 via intracellular staining. Depicted are the percentages of proliferating cells (B) or proliferating and IL-2 producing cells (C) comparing vehicle-treated groups (open bar) to FTY720-treated groups (filled bar).

FIGS. 14A-B demonstrates the immunotherapy doublets that result in increased BrdU incorporation by CD8+ and CD4+ tumor-infiltrating T cells in vivo. Tumor-infiltrating lymphocytes were harvested on day 7, 24 h after a single BrdU pulse in vivo, and cells were stained for BrdU along with anti-CD3, anti-CD4, and anti-CD8. Depicted are percentages of $BrdU^+$ cells that were $CD3^+$ $CD8^+$ (A) and $CD3^+$ $CD4^+$ (B).

FIGS. 15A-B illustrates in vivo proliferation of CD8+ and CD4+ positive T cells in spleen (A) and TdLN (B).

FIGS. 18A-B illustrates IDOi tumor outgrowth in response to single αCTLA-4, αPD-L1, IDOc and IDOi treatment (A) and pairwise (B) combinations of αCTLA-4 and αPD-L1 with IDOc and IDOi. Results were analyzed using a 2 way Anova comparing the single to double regimes as well as the double regimes to each other.

DETAILED DESCRIPTION

In some embodiments, the methods described herein involve the use of a combination of at least two of the following: an inhibitor of indoleamine-2,3-dioxygenase (IDO), an inhibitor of the PD-L1/PD-1 pathway, an inhibitor of CTLA-4, an inhibitor of CD25, or IL-7. The inventors particularly observed a major synergistic effect of combining anti-CTLA-4 with either an IDO inhibitor, with anti-PD-L1 mAb, or with CD-25 depletion. Such combinations have been found to demonstrate a synergistic effect in treating cancer and tumors, for example by reducing tumor size, increasing the percentage of antigen-specific T cells, and increasing T cell function.

A. SYNERGISTIC THERAPEUTIC EFFECTS

Figure 1:
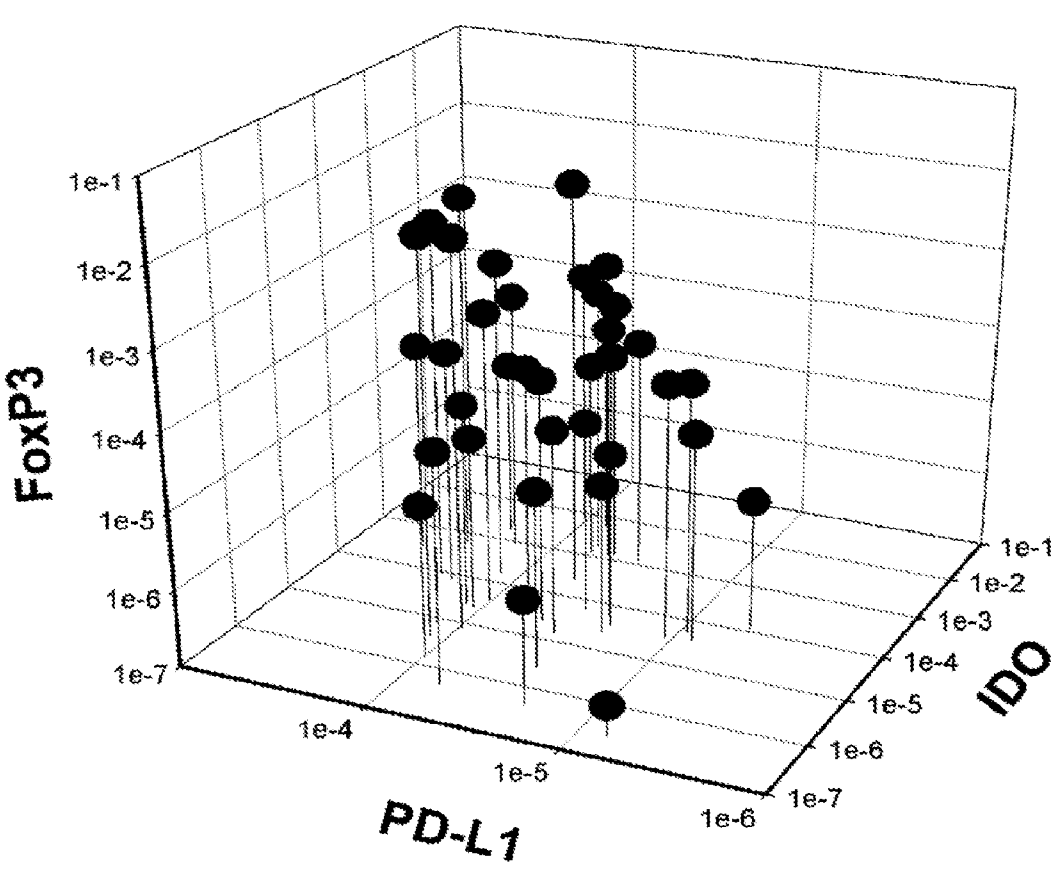
FIG. 1 illustrates the expression of FoxP3, PD-L1, and IDO in individual melanoma metastases as assessed by qRT-PCR.
Figure 2:
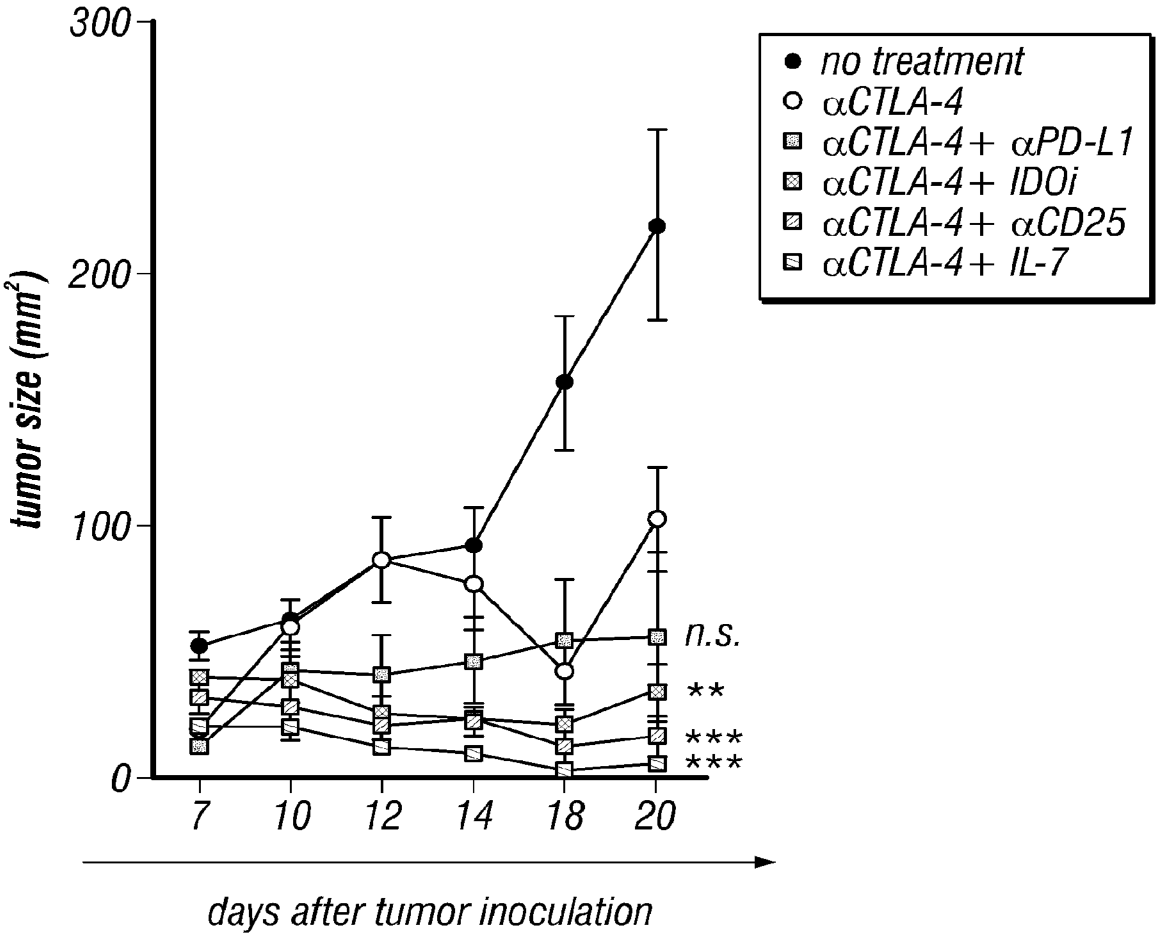
FIG. 2 illustrates the anti-CTLA-4 blockade, alone or in combination with other inhibitors. Measurement of tumor growth initiated 7 days post-tumor inoculation and continued throughout the experiment. Depicted are all time points until first animals had to be sacrificed. Two-way ANOVA test comparing each combination to anti-CTLA4 treatment.
Figures 3A, 3B:
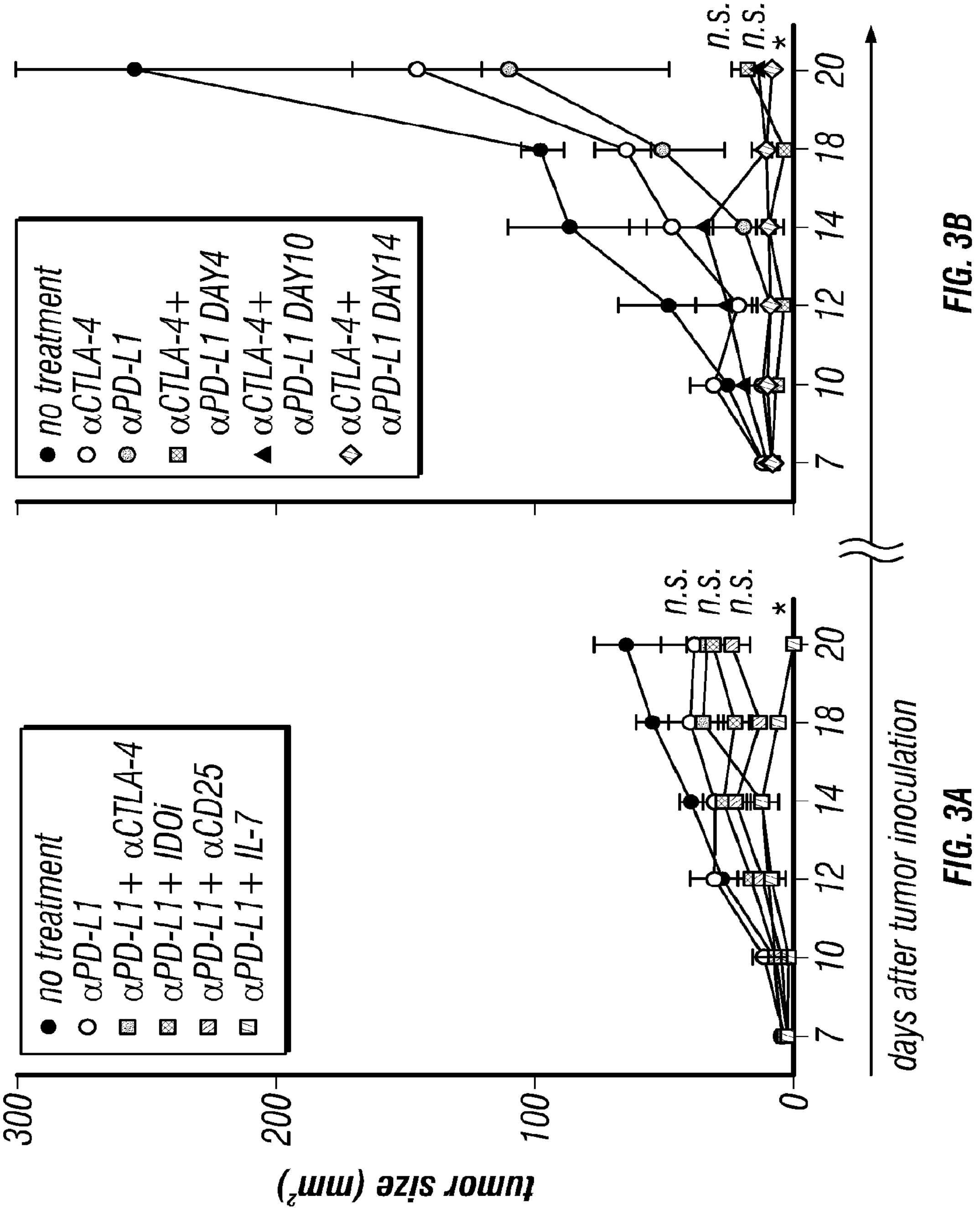
FIGS. 3A-B illustrates the anti-PD-L1 blockade, alone or in combination with other inhibitors. (A) Tumor measurement over time. (B) Anti-CTLA-4 regime and sequential administration of anti-PD-L1 starting either on day 4, day 10, or day 14 post-tumor inoculation. Time points are displayed until sacrifice of first animal. Two-way ANOVA test comparing each combination to anti-PD-L1 treatment.
Figures 4A, 4B:
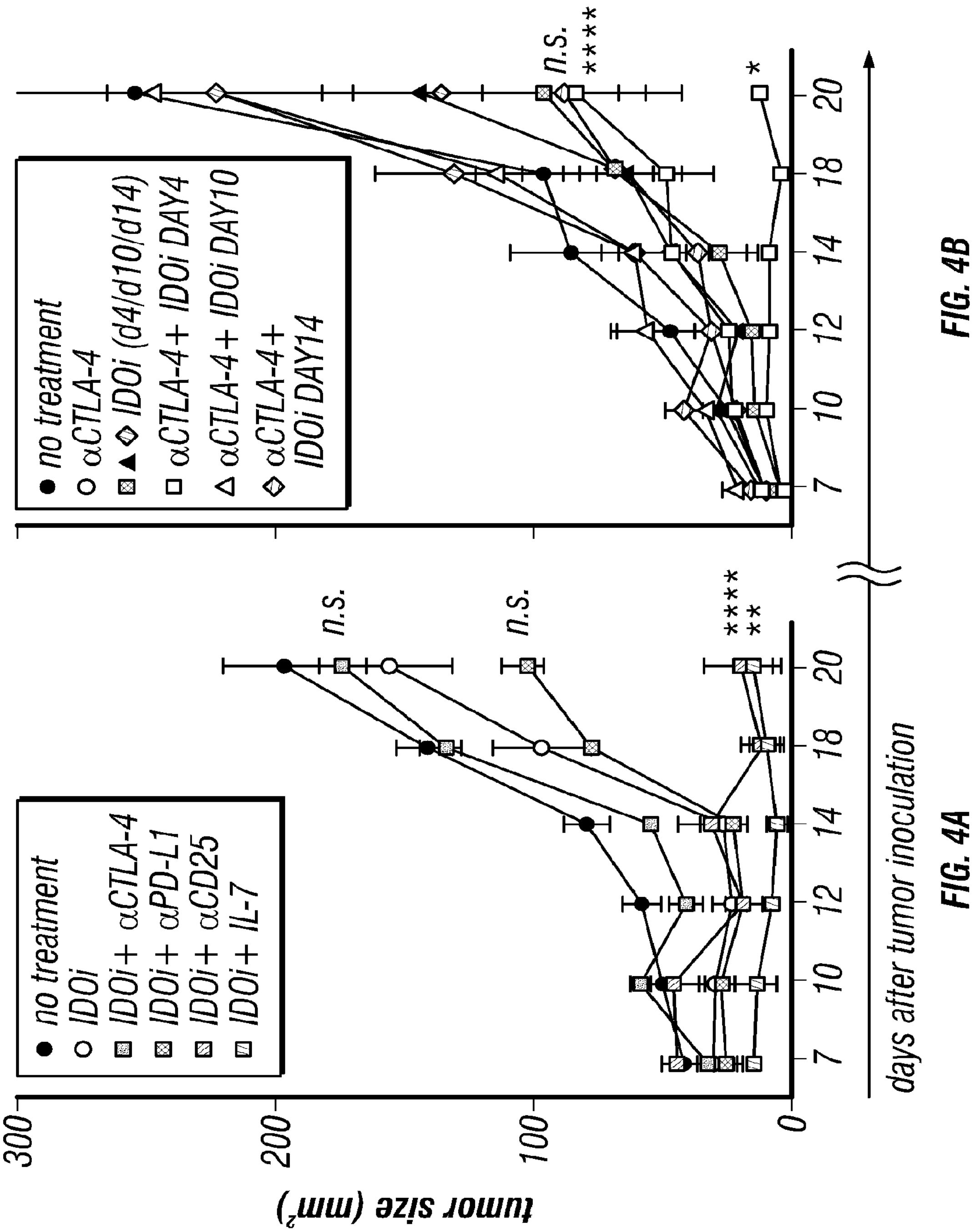
FIGS. 4A-B illustrates the effects of IDO inhibition. (A) Tumor measurement over time. (B) Anti-CTLA-4 regime and sequential administration of IDOi starting either on day 4, day 10, or day 14 post-tumor inoculation. Time points are displayed until sacrifice of first animal. Two-way ANOVA test comparing each combination to the matching IDOi treatment.
Figures 5A, 5B:
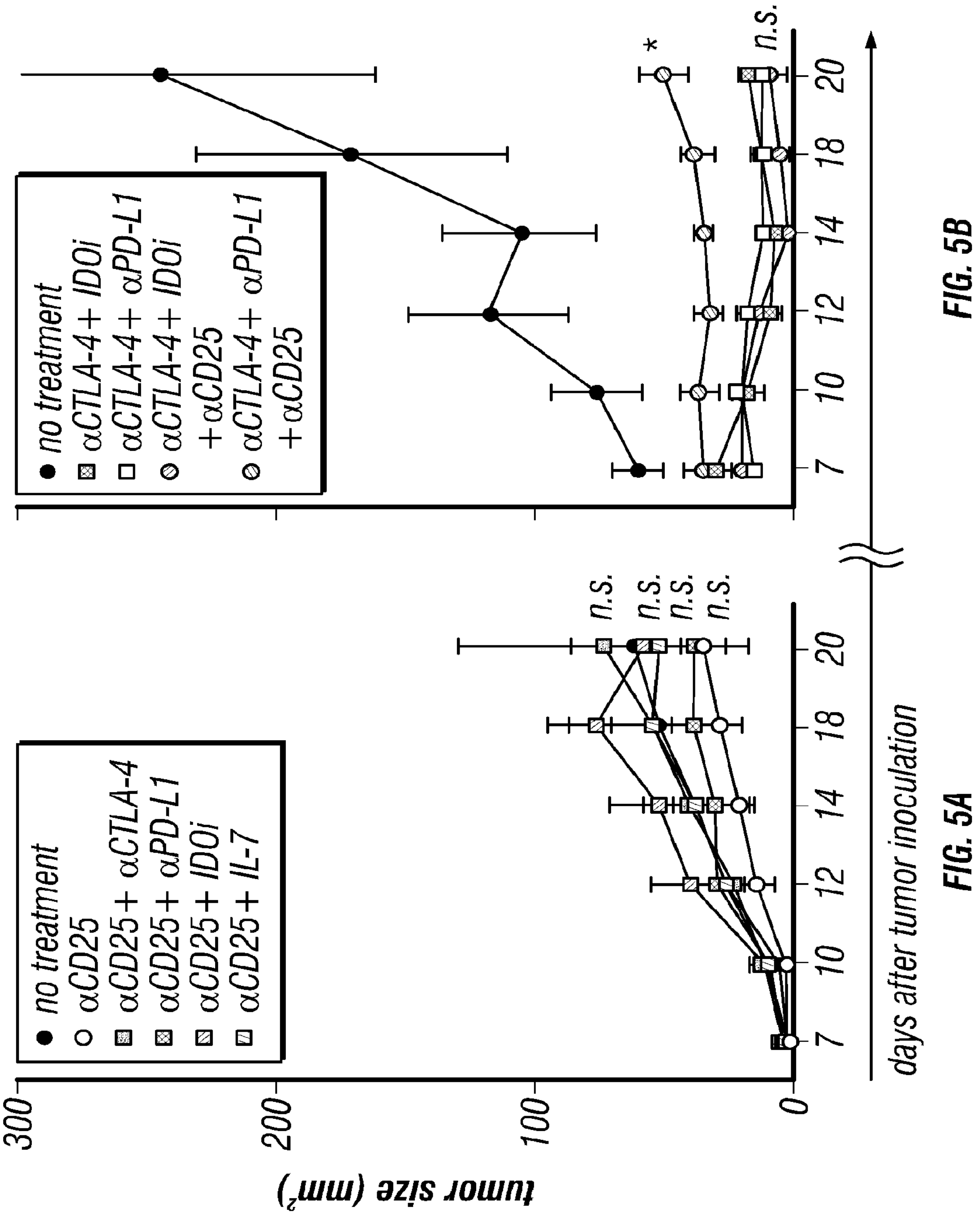
FIGS. 5A-B illustrates the effects of CD25-depletion. (A) Tumor outgrowth measured over time. (B) Combinations of anti-CTLA-4+anti-PD-L1 or IDOi, in combination with anti-CD25-mediated Treg depletion (circles). Time points are displayed until sacrifice of first animal. Two-way ANOVA test comparing each combination to anti-CD25 treatment or combination.

Human melanoma metastases co-express PD-L1, IDO, and Tregs, and show signs of classical anergy. The inventors performed a detailed analysis of the tumor microenvironment utilizing biopsies from patients with metastatic melanoma and identified two major subsets of tumors. One subset has a broad signature of inflammation that includes T cell markers and chemokines for lymphocyte recruitment, while the second subset is "bland" and lacks this inflammatory profile (Harlin et al., 2009). Clinical responses to melanoma vaccines appear to fall within the first subset, implying that non-inflamed tumors that lack chemokines might not be capable of supporting recruitment of activated T cells to enable tumor rejection (Gajewski et al., 2010). However, the question arises as to why the inflamed tumor phenotype that includes activated CD8+ T cells does not get rejected spontaneously by the host immune system. In fact, the inventors found that these tumors also show evidence of at least 4 immune inhibitory mechanisms: expression of PD-L1, presence of FoxP3+ Tregs, T cell anergy, and expression of IDO (Gajewski et al., 2006). A positive correlation was observed between the extent of the T cell infiltrate and the expression of PD-L1, FoxP3, and IDO (FIG. 1). An anergic phenotype was implied by lack of expression of B7-1 and B7-2 within the tumor microenvironment, and evidence for antigen-specific intrinsic T cell dysfunction (Harlin et al., 2006). Together, these results argue that immune suppressive mechanisms may dominate in the tumor microenvironment and prevent immune-mediated tumor elimination.

Treg depletion and reversal of anergy through homeostatic proliferation act synergistically to control B16 melanoma in vivo. The inventors have found that blockade of the PD-L1/PD-1 pathway, either using PD-1 knockout T cells or an anti-PD-L1 mAb, can have a positive impact on T cell-mediated tumor control (Blank et al., 2004; Zhang et al., 2009). Similarly, depletion of Tregs alone can have some impact (Kline et al., 2008), as can reversal of T cell anergy through homeostatic proliferation (Brown et al., 2006). However, in the B16 melanoma model, these effects are usually partial and don't result in complete tumor elimination. Interestingly, when Treg depletion was combined with homeostatic proliferation, complete eradication of B16 melanoma was observed (Kline et al., 2008). These results indicate that the combinatorial blockade of two or more regulatory pathways have a synergistic effect, thus enabling improved tumor control. In experiments, the inventors also have observed that combined blockade of PD-1/PD-L1 interactions plus homeostatic proliferation can also be synergistic.

Anergic T cells express LAG3, Tim3, and 4-1BB. Inasmuch as classical T cell anergy appears to be operational as one mechanism of immune escape in the tumor context, a detailed analysis of the molecular mechanisms controlling the anergic, dysfunctional state was performed. The inventors determined that the transcriptional regulator Egr2 drives expression of the anergy program, which includes genes encoding inhibitory signaling molecules such as DGK-α (Zha et al., 2006) and Cbl-b (unpublished data). The inventors utilized conditional Egr2-KO mice to demonstrate that T cells consequently become anergy resistant and show improved tumor control in vivo. Through an analysis of the entire Egr2-driven transcriptome in anergy, the inventors identified new surface markers that may help characterize the anergic phenotype but also may allow manipulation of anergic cells to restore their function. Two of these markers are LAG-3 and 4-1BB (FIG. 8). More detailed phenotyping has also revealed expression of Tim-3. Both LAG-3 and Tim3 are inhibitory molecules that can contribute to the blunting of T cell activation. Data indicates 4-1BB is a costimulatory receptor that might allow restoration of the function of anergic cells once ligated. Analysis of CD8+ T cells infiltrating B16 melanoma has revealed co-expression of all of these surface markers, on a subset of cells expression PD-1. Therefore, the administration of mAbs against LAG-3, 4-1BB, and Tim3 can also be performed in concert with IDO inhibition.

B. INDOLEAMINE-2,3-DIOXYGENASE (IDO)

Tryptophan (Trp) is an essential amino acid required for the biosynthesis of proteins, niacin and the neurotransmitter 5-hydroxytryptamine (serotonin). IDO catalyzes the first and rate limiting step in the degradation of L-tryptophan to N-formyl-kynurenine. In human cells, a depletion of Trp resulting from IDO activity is a prominent gamma interferon (IFN-γ)-inducible antimicrobial effector mechanism. IFN-γ stimulation induces activation of IDO, which leads to a depletion of Trp, thereby arresting the growth of Trp-dependent intracellular pathogens such as *Toxoplasma gondii* and *Chlamydia trachomatis*. IDO activity also has an antiproliferative effect on many tumor cells, and IDO induction has been observed in vivo during rejection of allogeneic tumors, indicating a possible role for this enzyme in the tumor rejection process (Daubener 1999; Taylor 1991).

It has been observed that HeLa cells co-cultured with peripheral blood lymphocytes (PBLs) acquire an immuno-inhibitory phenotype through up-regulation of IDO activity. A reduction in PBL proliferation upon treatment with interleukin-2 (IL2) was believed to result from IDO released by the tumor cells in response to IFN-γ secretion by the PBLs. This effect was reversed by treatment with 1-methyl-tryptophan (1MT), a specific IDO inhibitor. It was proposed that IDO activity in tumor cells may serve to impair antitumor responses (Logan 2002).

Further evidence for a tumoral immune resistance mechanism based on tryptophan degradation by IDO comes from the observation that most human tumors constitutively express IDO, and that expression of IDO by immunogenic mouse tumor cells prevents their rejection by preimmunized mice. This effect is accompanied by a lack of accumulation of specific T cells at the tumor site and can be partly reverted by systemic treatment of mice with an inhibitor of IDO, in the absence of noticeable toxicity. Thus, it was suggested that the efficacy of therapeutic vaccination of cancer patients might be improved by concomitant administration of an IDO inhibitor (Uyttenhove et al., 2003). It has also been shown that the IDO inhibitor, 1-MT, can synergize with chemotherapeutic agents to reduce tumor growth in mice, suggesting that IDO inhibition may also enhance the anti-tumor activity of conventional cytotoxic therapies (Muller et al., 2005).

One mechanism contributing to immunologic unresponsiveness toward tumors may be presentation of tumor antigens by tolerogenic host APCs. A subset of human IDO-expressing antigen-presenting cells (APCs) that coexpressed CD 123 (IL3RA) and CCR6 and inhibited T-cell proliferation have also been described. Both mature and immature CD123-positive dendritic cells suppressed T-cell activity, and this IDO suppressive activity was blocked by 1MT (Munn et al., 2002). It has also been demonstrated that mouse tumor-draining lymph nodes (TDLNs) contain a subset of plasmacytoid dendritic cells (pDCs) that constitutively express immunosuppressive levels of IDO. Despite comprising only 0.5% of lymph node cells, in vitro, these pDCs potently suppressed T cell responses to antigens presented by the pDCs themselves and also, in a dominant fashion, suppressed T cell responses to third-party antigens presented by nonsuppressive APCs. Within the population of pDCs, the majority of the functional IDO-mediated suppressor activity segregated with a novel subset of pDCs coexpressing the B-lineage marker CD19. Thus, it was hypothesized that IDO-mediated suppression by pDCs in TDLNs creates a local microenvironment that is potently suppressive of host antitumor T cell responses (Munn et al., 2004).

IDO degrades the indole moiety of tryptophan, serotonin and melatonin, and initiates the production of neuroactive and immunoregulatory metabolites, collectively known as kynurenines. By locally depleting tryptophan and increasing proapoptotic kynurenines, IDO expressed by dendritic cells (DCs) can greatly affect T-cell proliferation and survival. IDO induction in DCs could be a common mechanism of deletional tolerance driven by regulatory T cells. Because such tolerogenic responses can be expected to operate in a variety of physiopathological conditions, tryptophan metabolism and kynurenine production might represent a crucial interface between the immune and nervous systems (Grohmann, et al., 2003, Trends Immunol., 24: 242-8). In states of persistent immune activation, availability of free serum Trp is diminished and, as a consequence of reduced serotonin production, serotonergic functions may also be affected (Wirleitner et al., 2003).

Small molecule inhibitors of IDO are being developed to treat or prevent IDO-related diseases. For example, oxadiazole and other heterocyclic IDO inhibitors are reported in US 2006/0258719 and US 2007/0185165. PCT Publication WO 99/29310 reports methods for altering T cell-mediated immunity comprising altering local extracellular concentrations of tryptophan and tryptophan metabolites, using an inhibitor of IDO such as 1-methyl-DL-tryptophan, p-(3-benzofuranyl)-DL-alanine, p-[3-benzo(b)thienyl]-DL-alanine, and 6-nitro-L-tryptophan) (Munn et al., 1999). Reported in WO 03/087347, also published as European Patent 1501918, are methods of making antigen-presenting cells for enhancing or reducing T cell tolerance (Munn et al., 2003). Compounds having indoleamine-2,3-dioxygenase (IDO) inhibitory activity are further reported in WO 2004/094409; and U.S. Patent Application Publication No. 2004/0234623 is directed to methods of treating a subject with a cancer or an infection by the administration of an inhibitor of indoleamine-2,3-dioxygenase in combination with other therapeutic modalities. In some embodiments, the small molecule inhibitors are those found in the Examples below or disclosed in U.S. Pat. No. 8,088,803, which is incorporated in its entirety herein.

C. CTLA-4

CTLA4 (Cytotoxic T-Lymphocyte Antigen 4) is a CD28-family receptor expressed on activated CD8+ and CD4+ T cells. It binds the same ligands as CD28 (CD80 and CD86 on B cells and dendritic cells), but with higher affinity than CD28. In contrast to CD28, which enhances cell function when bound at the same time as the T cell receptor, CTLA4 inhibits T cell functioning. CTLA4 blockade releases inhibitory controls on T cell activation and proliferation, inducing antitumor immunity in both preclinical and early clinical trials (Quezada et al., 2006). The CTLA4 pathway is the subject of much interest (see, for example, U.S. Pat. No. 7,229,628).

Inhibitors of the CTLA4 pathway include, but are not limited to antibodies, peptides, nucleic acid molecules (including, for example, an antisense molecule, a PNA, or an RNAi), peptidomimetics, small molecules, a soluble CTLA4 ligand polypeptide, or a chimeric polypeptide (for example, a chimeric CTLA4 ligand/immunoglobulin molecule). An antibody may be an intact antibody, an antibody binding fragment, or a chimeric antibody. A chimeric antibody may include both human and non-human portions. An antibody may be a polyclonal or a monoclonal antibody. An antibody may be derived from a wide variety of species, including, but not limited to mouse and human. An antibody may be a humanized antibody. An antibody may be linked to another functional molecule, for example, another peptide or protein, a toxin, a radioisotype, a cytotoxic agent, cytostatic agent, a polymer, such as, for example, polyethylene glycol, polypropylene glycol or polyoxyalkenes. In some embodiments, a mixture or cocktail of various inhibitors of the CTLA4 pathway may be administered.

Any of a variety of antibodies may be used, including, but not limited to, any of those described herein and those commercially available, for example, ipilimumab from Bristol-Myers Squibb and tremelimumab from MedImmune. Other anti-CTLA4 antibodies include, but are not limited to, those taught in U.S. Pat. Nos. 7,311,910; 7,307,064; 7,132,281; 7,109,003; 7,034,121; 6,984,720; and 6,682,736. In some embodiments, one or more anti-CTLA4 antibodies may be humanized.

D. PD-L1/PD-1 AXIS

Programmed death ligand 1 (PD-L1) is a 40 kDa type 1 transmembrane protein that has been speculated to play a major role in suppressing the immune system during particular events such as pregnancy, tissue allografts, autoimmune disease and other disease states such as hepatitis. Normally the immune system reacts to foreign antigens where there is some accumulation in the lymph nodes or spleen which triggers a proliferation of antigen-specific CD8+ T cell. The formation of PD-1 receptor/PD-L1 ligand complex transmits an inhibitory signal which reduces the proliferation of these CD8+ T cells at the lymph nodes and supplementary to that PD-1 is also able to control the accumulation of foreign antigen specific T cells in the lymph nodes through apoptosis which is further mediated by a lower regulation of the gene Bcl-2. PD-L1 binds to its receptor, PD-1, found on activated T cells, B cells, and myeloid cells, to modulate activation or inhibition. The affinity between PD-L1 and PD-1, as defined by the dissociation constant Kd, is 770 nM.

Inhibitors of the PD-L1/PD-1 pathway include, but are not limited to, antibodies, peptides, nucleic acid molecules (including, for example, an antisense molecule, a PNA, or an RNAi), peptidomimetics, small molecules, a soluble PD-1 ligand polypeptide, or a chimeric polypeptide (for example, a chimeric PD-1 ligand/Immunoglobulin molecule). An antibody may be an intact antibody, an antibody binding fragment, or a chimeric antibody. A chimeric antibody may include both human and non-human portions. An antibody may be a polyclonal or a monoclonal antibody. An antibody may be a derived from a wide variety of species, including, but not limited to mouse and human. An antibody may be a humanized antibody. An antibody may be linked to another functional molecule, for example, another peptide or protein, a toxin, a radioisotype, a cytotoxic agent, cytostatic agent, a polymer, such as, for example, polyethylene glycol, polypropylene glycol or polyoxyalkenes.

Any of a variety of antibodies may be used, including, but not limited to, any of those described herein and those commercially available, for example, BMS-936559 or BMS-936558 from Bristol-Myers Squibb, MPDL3280A from Genentech, MK-3475 from Merck, CT-011 from Curetech, and MEDI4736 from MedImmune.

In some embodiments, one or more anti-PDL-1 antibodies may be humanized.

E. ANTIBODIES

The term "antibody" as used herein refers to an immunoglobulin which possesses the ability to combine with an antigen. It comprises at least two heavy (H) chains and two light (L) chains inter-connected by disulfide bonds. Non-limiting examples of antibodies include monoclonal antibodies (e.g., full length or intact monoclonal antibodies), polyclonal antibodies, multivalent antibodies, and multi-specific antibodies (e.g., bi-specific antibodies as long as they exhibit the desired biological activity). An antibody can be human, humanized or affinity-matured, or combinations thereof.

The term "antibody fragment" comprises only a portion of an intact antibody, wherein the portion preferably retains at least one, preferably most or all, of the functions normally associated with that portion when present in an intact antibody. Examples of antibody fragments include Fab, Fab', F(ab')2, and Fv fragments; diabodies; linear antibodies; single-chain antibody molecules; and multispecific antibodies formed from antibody fragments. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody. In one embodiment, an antibody fragment is a monovalent antibody that has an in vivo half-life substantially similar to an intact antibody. For example, such an antibody fragment may comprise an antigen-binding arm linked to an Fc sequence capable of conferring in vivo stability to the fragment.

An "isolated" antibody is one which has been identified and separated or recovered, or both, from a component of its natural environment. Contaminant components of an isolated antibody's natural environment are materials which would interfere with diagnostic or therapeutic uses of the antibody. Non-limiting examples of such contaminants include enzymes, hormones, and other proteinaceous or non-proteinaceous solutes. In some embodiments, for example, the antibody may be purified to greater than 95% by weight of antibody as determined by the Lowry method, and sometimes more than 99% by weight. Isolated antibody includes the antibody in situ within recombinant cells because at least one component of the antibody's natural environment will not be present. Ordinarily, however, isolated antibody will be prepared by at least one purification step.

The terms "monoclonal antibody" or "monoclonal antibody composition" as used herein refer to a preparation of antibody molecules of single molecular composition. A monoclonal antibody composition displays a single binding specificity and affinity for a particular epitope. The monoclonal antibodies herein specifically include "chimeric" antibodies in which a portion of the heavy or light chain, or both, is identical with or homologous to corresponding sequences in antibodies derived from a particular species or belonging to a particular antibody class or subclass, while the remainder of the chain or chains are identical with or homologous to corresponding sequences in antibodies derived from another species or belonging to another antibody class or subclass, as well as fragments of such antibodies so long as they exhibit the desired biological activity.

The term "variable" refers to the fact that certain portions of the variable domain sequences differ extensively among antibodies and are important to the binding and specificity of each particular antibody for its particular antigen. However, such variability is not evenly distributed throughout the variable domains of antibodies and is concentrated in three segments called complementarity-determining regions (CDRs) or hypervariable regions which occur in both of the light-chain and the heavy-chain variable domains. The more highly conserved portions of variable domains are called the framework (FR). The variable domains of native heavy and light chains each comprise four FR regions (largely adopting a beta-sheet configuration) connected by three CDRs (which form loops connecting, and in some cases forming part of, the beta sheet structure). The CDRs in each chain are held together in close proximity by the FR regions and, with the CDRs from the other chain, contribute to the formation of the antigen-binding site of antibodies. The constant domains are not involved directly in binding an antibody to an antigen, but exhibit various effector functions, such as participation of the antibody in antibody-dependent cellular toxicity.

The term "hypervariable region," "HVR," or "HV," when used herein, refers to the regions of an antibody variable domain which are hypervariable in sequence or form structurally defined loops, or both. Generally, antibodies comprise six hypervariable regions; three in the VH (H1, H2, H3), and three in the VL (L1, L2, L3).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired specificity, affinity, and capacity. In some instances, FR residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody may comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally may also comprise at least a portion of an immunoglobulin constant region (Fc), typically that of a human immunoglobulin.

The term "recombinant human antibody," as used herein, includes all human antibodies that are prepared, expressed, created or isolated by recombinant means, such as (a) antibodies isolated from an animal (e.g., a mouse) that is transgenic or trans-chromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. In other certain embodiments, pre-assembled trinucleotides are used in the chemical synthesis of the CDR sequences for such recombinant human antibodies.

"Chimeric" antibodies (immunoglobulins) have a portion of the heavy or light chain, or both, that is identical or homologous to corresponding sequences in antibodies derived from a particular species or belonging to a particular antibody class or subclass, while the remainder of the chain or chains are identical or homologous to corresponding sequences in antibodies derived from another species or belonging to another antibody class or subclass, as well as fragments of such antibodies, so long as they exhibit the desired biological activity. Humanized antibody as used herein is a subset of chimeric antibodies.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding.

An "antigen" is a predetermined antigen to which an antibody can selectively bind. The target antigen may be polypeptide, carbohydrate, nucleic acid, lipid, hapten or other naturally occurring or synthetic compound.

An "epitope" is the portion of the antigen to which the antibody selectively binds. For a polypeptide antigen, the epitope is generally a peptide portion of about four to ten amino acids.

The term "diabodies" refers to small antibody fragments with two antigen-binding sites, such fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

A "human antibody" is one which possesses an amino acid sequence which corresponds to that of an antibody produced by a human or has been made using any of the techniques for making human antibodies as disclosed herein, or both. This definition of a human antibody specifically excludes a humanized antibody comprising non-human antigen-binding residues.

An "affinity-matured" antibody is one with one or more alterations in one or more CDRs thereof which result in an improvement in the affinity of the antibody for antigen, compared to a parent antibody which does not possess those alteration(s). For example, affinity-matured antibodies may have nanomolar or even picomolar affinities for the target antigen. Affinity-matured antibodies are produced by procedures well-known in the art.

A "blocking" antibody or an "antagonist" antibody is one which inhibits or reduces biological activity of the antigen it binds. Preferred blocking antibodies or antagonist antibodies substantially or completely inhibit the biological activity of the antigen.

1. General Methods for the Production of Antibodies and Nucleic Acids Encoding Antibodies Embodiments include isolated antibodies or antibody fragments that bind immunologically to native cell surface-expressed CTLA4, PD-L1, or PD-1 and isolated polynucleotides comprising sequences encoding one or more antibodies or antibody fragments that bind to CTLA4, PD-L1, or PD-1. Embodiments also include pharmaceutical compositions that include antibodies or antibody fragments that binds immunologically to native cell surface-expressed CTLA4, PD-L1, or PD-1 and polynucleotides comprising sequences encoding one or more antibodies or antibody fragments that bind to CTLA4, PD-L1, or PD-1.

In particular embodiments the anti-CTLA4, anti-PD-1, or anti-PD-L1 antibodies are monoclonal antibodies. Monoclonal antibodies can be produced by a variety of techniques, such as by conventional monoclonal antibody methodology using standard somatic cell hybridization techniques and viral or oncogenic transformation of B lymphocytes.

Monoclonal antibodies may be obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

The anti-CTLA4, anti-PD-1, or anti-PD-L1 monoclonal antibodies can be made using a hybridoma method, or may be made by recombinant DNA methods well-known to those of ordinary skill in the art.

Regarding the hybridoma method, the first step is immunization of an appropriate host, as may be achieved by coupling a peptide or polypeptide immunogen to a carrier. Exemplary carriers are keyhole limpet hemocyanin (KLH), bovine serum albumin (BSA, ovalbumin, mouse serum albumin and rabbit serum albumin). As also is well known in the art, the immunogenicity of a particular immunogen composition can be enhanced by the use of non-specific stimulators of the immune response, known as adjuvants.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. One or more additional booster injections may be given. The process of boosting and titering is repeated until a suitable titer is achieved. When a desired level of immunogenicity is obtained, the immunized animal can be bled and the serum isolated and stored, and/or the animal can be used to generate monoclonal antibodies.

Following immunization, somatic cells with the potential for producing antibodies, specifically B lymphocytes (B cells), are selected for use in the monoclonal antibody-generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized. Any one of a number of myeloma cells may be used, as are known to those of skill in the art. For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions. One particular murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell C line. Additional fusion partner lines for use with human B cells include KR12 (ATCC® CRL-8658; K6H6/B5 (ATCC® CRL-1823 SHM-D33 (ATCC® CRL-1668) and HMMA2.5 (Posner et al., 1987). In a particular embodiment, the line used to generate the antibody in this invention is OUR-1.

Methods for generating hybrids of antibody-producing spleen or lymph node cells and myeloma cells usually comprise mixing somatic cells with myeloma cells in the presence of an agent or agents (chemical or electrical) that promote the fusion of cell membranes.

The viable, fused hybrids may be differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

Hypoxanthine aminopterm thymidine (HAT) may be used as a selection medium. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas are then serially diluted and cloned into individual antibody-producing cell lines, which clones can then be propagated indefinitely to provide monoclonal antibodies. The cell lines may be exploited for monoclonal antibody production using any method known to those of ordinary skill in the art. In one example, a sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as severe combined immunodeficient (SCID) mice, to prevent tumor rejection. The injected animal develops tumors secreting the specific monoclonal antibody produced by the fused cell hybrid. The body fluids of the animal, such as serum or ascites fluid, can then be tapped to provide monoclonal antibodies in high concentration. The individual cell lines could also be cultured in vitro, where the monoclonal antibodies are naturally secreted into the culture medium from which they can be readily obtained in high concentrations.

In the hybridoma method, a mouse or other appropriate host animal is immunized to elicit lymphocytes that produce or are capable of producing antibodies that will specifically bind to the protein used for immunization. Antibodies to CTLA4, PD-L1, or PD-1 may generally be raised in animals by multiple subcutaneous (sc) or intraperitoneal (ip) injections of CTLA4, PD-L1, or PD-1 and an adjuvant. CTLA4, PD-L1, or PD-1 may be prepared using methods well-known in the art.

In some embodiments, lymphocytes may be immunized in vitro. Lymphocytes then are fused with myeloma cells using a suitable fusing agent, such as polyethylene glycol, to form a hybridoma cell.

The hybridoma cells thus prepared may be seeded and grown in a suitable culture medium that preferably contains one or more substances that inhibit the growth or survival of the unfused, parental myeloma cells. Culture medium in which hybridoma cells are growing is assayed for production of monoclonal antibodies directed against CTLA4, PD-L1, or PD-1. The binding specificity of monoclonal antibodies produced by hybridoma cells may be determined be techniques well-known to those in the art, such as by immunoprecipitation or by an in vitro binding assay (e.g., radioimmunoassay (RIA) or enzyme-linked immunoabsorbent assay (ELISA)). The binding affinity of the monoclonal antibody can, for example, be determined by a Scatchard analysis. After hybridoma cells are identified that produce antibodies of the desired specificity, affinity, and/or activity, the clones may be subcloned by limiting dilution procedures and grown by standard methods. The monoclonal antibodies secreted by the subclones may be suitably separated from the culture medium by conventional immunoglobulin purification procedures such as, for example, protein A-Sepharose®, hydroxylapatite chromatography, gel electrophoresis, dialysis, or affinity chromatography.

The anti-CTLA4, anti-PD-1, or anti-PD-L1 antibodies can be made by using combinatorial libraries, such as a phage display library, to screen for synthetic antibody clones with the desired activity or activities. In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. In a certain embodiment, the anti-CTLA4, anti-PD-1, or anti-PD-L1 antibodies are produced in bacteria and the library is screened using phage display to identify the antibody with a high affinity to CTLA4, PD-L1, or PD-1.

Monoclonal antibodies produced by any means may be further purified, if desired, using any technique known to those of ordinary skill in the art, such as filtration, centrifugation and various chromatographic methods such as FPLC or affinity chromatography or any other method known to those of ordinary skill in the art.

Nucleic acids encoding antibody gene fragments may be obtained from immune cells harvested from humans or animals. If a library biased in favor of anti-CTLA4, anti-PD-1, or anti-PD-L1 clones is desired, the subject is immunized with CTLA4, PD-L1, or PD-1 to generate an antibody response, and spleen cells and/or circulating B cells or other peripheral blood lymphocytes (PBLs) are recovered for library construction. Additional enrichment for anti-CTLA4, anti-PD-L1, or anti-PD-1 reactive cell populations can be obtained by using a suitable screening procedure to isolate B cells expressing CTLA4, PD-L1, or PD-1-specific membrane bound antibody. Alternatively, the use of spleen cells and/or B cells or other PBLs from an unimmunized donor provides a better representation of the possible antibody repertoire, and also permits the construction of an antibody library using any animal (human or non-human) species in which CTLA4, PD-L1, or PD-1 is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, etc. Nucleic acid encoding antibody variable gene segments are recovered from the cells of interest and amplified.

Nucleic acid sequence encoding a CTLA4, PD-L1, or PD-1 polypeptide can be designed using the amino acid sequence of the desired region of CTLA4, PD-L1, or PD-1. Alternatively, the cDNA sequence (or fragments thereof) may be used. DNAs encoding CTLA4, PD-L1, or PD-1 can be prepared by a variety of methods known in the art. Following construction of the DNA molecule encoding CTLA4, PD-L1, or PD-1, the DNA molecule is operably linked to an expression control sequence in an expression vector, such as a plasmid, wherein the control sequence is recognized by a host cell transformed with the vector. Suitable vectors for expression in prokaryotic and eukaryotic host cells are known in the art. Optionally, the DNA encoding CTLA4, PD-L1, or PD-1 is operably linked to a secretory leader sequence resulting in secretion of the expression product by the host cell into the culture medium. Host cells are transfected and preferably transformed with the expression or cloning vectors and cultured in conventional nutrient media modified as appropriate for inducing promoters, selecting transformants, or amplifying the genes encoding the desired sequences.

The purified CTLA4, PD-L1, or PD-1 can be attached to a suitable matrix such as agarose beads, acrylamide beads, glass beads, cellulose, various acrylic copolymers, hydroxyl methacrylate gels, polyacrylic and polymethacrylic copolymers, nylon, neutral and ionic carriers, and the like, for use in the affinity chromatographic separation of phage display clones. Alternatively, CTLA4, PD-L1, or PD-1 can be used to coat the wells of adsorption plates, expressed on host cells affixed to adsorption plates or used in cell sorting, or conjugated to biotin for capture with streptavidin-coated beads, or used in any other art-known method for panning phage display libraries. The phage library samples are contacted with immobilized CTLA4, PD-L1, or PD-1 under conditions suitable for binding of at least a portion of the phage particles with the adsorbent. Normally, the conditions, including pH, ionic strength, temperature and the like are selected to mimic physiological conditions. The phages bound to the solid phase are washed and then eluted. Moreover, the enriched phages can be grown in bacterial culture and subjected to further rounds of selection.

DNA encoding the hybridoma-derived monoclonal antibodies or phage display Fv clones is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of the desired monoclonal antibodies in the recombinant host cells.

DNA encoding the Fv clones of the invention can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. A Fv clone derived from the variable domain DNA of one animal (such as human) species and then fused to constant region DNA of another animal species to form coding sequence(s) for "hybrid," full length heavy chain and/or light chain is included in the definition of "chimeric" and "hybrid" antibody as used herein. In a preferred embodiment, a Fv clone derived from human variable DNA is fused to human constant region DNA to form coding sequence(s) for all human, full or partial length heavy and/or light chains.

DNA encoding anti-CTLA4 or anti-PD-L1 antibody derived from a hybridoma can also be modified, for example, by substituting the coding sequence for human heavy- and light-chain constant domains in place of homologous murine sequences derived from the hybridoma clone. DNA encoding a hybridoma or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies of the invention.

2. Antibody Fragments

In some embodiments, methods and compositions encompass antibody fragments. In certain circumstances there are advantages of using antibody fragments, rather than whole antibodies. The smaller size of the fragments may allow for rapid clearance, and may lead to improved access to solid tumors.

Non-limiting examples of antibody fragments include Fab, Fab', Fab'-SH and F(ab')2 fragments of the anti-CTLA4 or anti-PD-L1 antibodies provided herein. These antibody fragments can be created by traditional means, such as enzymatic digestion, or may be generated by recombinant techniques. Some antibody fragments may be chimeric or humanized. These fragments are useful for the diagnostic and therapeutic purposes set forth below.

Various techniques may be used for the production of antibody fragments. Traditionally, these fragments were derived via proteolytic digestion of intact antibodies, such as with pepsin or papain and/or by cleavage of disulfide bonds by chemical reduction. However, these fragments can now be produced directly by recombinant host cells. For example, Fab, Fv and ScFv antibody fragments can all be expressed in and secreted from *E. coli*, thus allowing the facile production of large amounts of these fragments. Alternatively, monoclonal antibody fragments can be synthesized using an automated peptide synthesizer.

Antibody fragments can be isolated from the antibody phage libraries discussed above. Alternatively, Fab'-SH fragments can be directly recovered from *E. coli* and chemically coupled to form F(ab')2 fragments. According to another approach, F(ab')2 fragments can be isolated directly from recombinant host cell culture. Other techniques for the production of antibody fragments will be apparent to the skilled practitioner. In other embodiments, the antibody of choice is a single chain Fv fragment (scFv). Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. The antibody fragment may also be a "linear antibody." Such linear antibody fragments may be monospecific or bispecific.

3. Humanized Antibodies

Some embodiments also encompass humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed using any method known to those of ordinary skill in the art. Accordingly, such "humanized" antibodies are chimeric antibodies wherein substantially less than an intact human variable domain has been substituted by the corresponding sequence from a non-human species. In practice, humanized antibodies are typically human antibodies in which some hypervariable region residues.

It is further important that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

4. Human Antibodies

Human anti-CTLA4, anti-PD-1, or anti-PD-L1 antibodies (or fragments thereof) can be constructed by combining Fv clone variable domain sequence(s) selected from human-derived phage display libraries with known human constant domain sequences(s) as described above. Alternatively, human monoclonal anti-CTLA4, anti-PD-1, or anti-PD-L1 antibodies can be made by the hybridoma method. Other methods known to those of ordinary skill in the art can be utilized.

Transgenic animals (e.g. mice) can be produced that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge.

Gene shuffling can also be used to derive human antibodies from non-human, e.g. rodent, antibodies, where the human antibody has similar affinities and specificities to the starting non-human antibody. According to one method, which is also called "epitope imprinting," either the heavy or light chain variable region of a non-human antibody fragment obtained by phage display techniques as described above is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained. Unlike traditional humanization of non-human antibodies by CDR grafting, this technique provides completely human antibodies, which have no FR or CDR residues of non-human origin.

5. Bispecific Antibodies

Bispecific antibodies are monoclonal, preferably human or humanized, antibodies that have binding specificities for at least two different antigens. In the present case, one of the binding specificities is for CTLA4, PD-L1, or PD-1 and the other is for any other antigen. In some embodiments, one of the binding specificities is for CTLA4 and the other is for PD-L1. Exemplary bispecific antibodies may bind to two different epitopes of the CTLA4, PD-L1, or PD-1 protein. Bispecific antibodies may also be used to localize cytotoxic agents to cells which express CTLA4, PD-L1, or PD-1. These antibodies possess a CTLA4, PD-L1, or PD-1-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab')2 bispecific antibodies).

Methods for making bispecific antibodies are known in the art. Traditionally, the recombinant production of bispecific antibodies is based on the co-expression of two immunoglobulin heavy chain-light chain pairs, where the two heavy chains have different specificities.

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In some embodiments, the bispecific antibodies are composed of a hybrid immunoglobulin heavy chain with a first binding specificity in one arm, and a hybrid immunoglobulin heavy chain-light chain pair (providing a second binding specificity) in the other arm. According to another approach, the interface between a pair of antibody molecules can be engineered to maximize the percentage of heterodimers which are recovered from recombinant cell culture.

Techniques for generating bispecific antibodies from antibody fragments have also been described in the literature. For example, bispecific antibodies can be prepared using chemical linkage.

Various techniques for making and isolating bispecific antibody fragments directly from recombinant cell culture have also been described. For example, bispecific antibodies have been produced using leucine zippers. The "diabody" technology provides an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments involves the use of single-chain Fv (sFv) dimmers.

6. Multivalent Antibodies

A multivalent antibody may be internalized (and/or catabolized) faster than a bivalent antibody by a cell expressing an antigen to which the antibodies bind. Antibodies can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody may comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. In some embodiments, the multivalent antibody comprises (or consists of) three to about eight, but preferably four, antigen binding sites. The multivalent antibody comprises at least one polypeptide chain (and preferably two polypeptide chains), wherein the polypeptide chain(s) comprise two or more variable domains.

7. Antibody Variants

In some embodiments, amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid alterations may be introduced in the subject antibody amino acid sequence at the time that sequence is made.

Amino acid sequence insertions include amino- and/or carboxyl-terminal fusions ranging in length from one residue to polypeptides containing a hundred or more residues, as well as intrasequence insertions of single or multiple amino acid residues. Non-limiting examples of terminal insertions include an antibody with an N-terminal methionyl residue or the antibody fused to a cytotoxic polypeptide. Other insertional variants of the antibody molecule include the fusion to the N- or C-terminus of the antibody to an enzyme or a polypeptide which increases the serum half-life of the antibody or to a therapeutic amino acid sequence such as a thrombogenic polypeptide.

Another type of amino acid variant of the antibody alters the original glycosylation pattern of the antibody. Such altering includes deleting one or more carbohydrate moieties found in the antibody, and/or adding one or more glycosylation sites that are not present in the antibody. Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

One type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites are mutated to generate all possible amino acid substitutions at each site. The antibodies thus generated are displayed from filamentous phage particles as fusions to the gene III product of M13 packaged within each particle. The phage-displayed variants are then screened for their biological activity (e.g. binding affinity). In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides, thereby generating a Fc region variant. In accordance with this description and the teachings of the art, it is contemplated that in some embodiments, an antibody used in methods may comprise one or more alterations as compared to the wild type counterpart antibody, e.g. in the Fc region. These antibodies would nonetheless retain substantially the same characteristics required for therapeutic utility as compared to their wild type counterpart.

8. Antibody Derivatives

The antibodies described herein can be further modified to contain additional non-proteinaceous moieties that are known in the art and readily available. For example, in some embodiments, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymers are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In these contexts, one may to link such antibodies to diagnostic or therapeutic agents, or use them as capture agents or competitors in competitive assays.

F. PHARMACEUTICAL COMPOSITIONS AND METHODS

In some embodiments, pharmaceutical compositions are administered to a subject. Different aspects involve administering an effective amount of a composition to a subject. In some embodiments, a composition comprising an inhibitor may be administered to the subject or patient to treat cancer or reduce the size of a tumor. Additionally, such compounds can be administered in combination with an additional cancer therapy.

Inhibitors can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and, the preparations can also be emulsified. In addition to the compounds formulated for parenteral administration, other pharmaceutically acceptable forms include, e.g., aerosolizable, inhalable, or instillable formulations; tablets or other solids for oral administration; time release capsules; creams; lotions; mouthwashes; and the like. The preparation of such formulations will be known to those of skill in the art in light of the present disclosure.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. The term "pharmaceutically acceptable carrier," means a pharmaceutically acceptable material, composition or vehicle, such as a liquid or solid filler, diluent, excipient, solvent or encapsulating material, involved in carrying or transporting a chemical agent.

As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. Pharmaceutically acceptable salts include the conventional non-toxic salts or the quaternary ammonium salts of the parent compound formed, for example, from non-toxic inorganic or organic acids. The pharmaceutically acceptable salts can be synthesized from the parent compound which contains a basic or acidic moiety by conventional chemical methods.

Some variation in dosage will necessarily occur depending on the condition of the subject. The person responsible for administration will, in any event, determine the appropriate dose for the individual subject. An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the effects desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

Typically, for a human adult (weighing approximately 70 kilograms), from about 0.1 mg to about 3000 mg (including all values and ranges there between), or from about 5 mg to about 1000 mg (including all values and ranges there between), or from about 10 mg to about 100 mg (including all values and ranges there between), of a compound are administered. It is understood that these dosage ranges are by way of example only, and that administration can be adjusted depending on the factors known to the skilled artisan.

In certain embodiments, a subject is administered about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 milligrams (mg) or micrograms (mcg) or μg/kg or micrograms/kg/minute or mg/kg/min or micrograms/kg/hour or mg/kg/hour, or any range derivable therein. In specific embodiments, 50 mg/10 mL (5 mg/mL) of the inhibitor ipilimumab is administered. In specific embodiments, 200 mg/40 mL (5 mg/mL) of the inhibitor ipilimumab is administered.

A dose may be administered on an as needed basis or every 1, 2, 3, 4, 5, 6, 7, 8, 9, 10, 11, 12, 18, or 24 hours (or any range derivable therein) or 1, 2, 3, 4, 5, 6, 7, 8, 9, or times per day (or any range derivable therein). A dose may be first administered before or after signs of an infection are exhibited or felt by a patient or after a clinician evaluates the patient for an infection. In some embodiments, the patient is administered a first dose of a regimen 1, 2, 3, 4, 5, 6, 7, 8, 9, 10, 11, 12 hours (or any range derivable therein) or 1, 2, 3, 4, or 5 days after the patient experiences or exhibits signs or symptoms of an infection (or any range derivable therein). The patient may be treated for 1, 2, 3, 4, 5, 6, 7, 8, 9, 10 or more days (or any range derivable therein) or until symptoms of an infection have disappeared or been reduced or after 6, 12, 18, or 24 hours or 1, 2, 3, 4, or 5 days after symptoms of an infection have disappeared or been reduced. In specific embodiments, the inhibitor ipilimumab is administered every three weeks.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder," and "tumor" are not mutually exclusive as referred to herein.

The cancers amenable for treatment include, but are not limited to, melanoma, carcinoma, lymphoma, blastoma, sarcoma, and leukemia or lymphoid malignancies. More particular examples of such cancers include breast cancer, colon cancer, rectal cancer, colorectal cancer, kidney or renal cancer, clear cell cancer lung cancer including small-cell lung cancer, non-small cell lung cancer, adenocarcinoma of the lung and squamous carcinoma of the lung, squamous cell cancer (e.g. epithelial squamous cell cancer), cervical cancer, ovarian cancer, prostate cancer, prostatic neoplasms, liver cancer, bladder cancer, cancer of the peritoneum, hepatocellular cancer, gastric or stomach cancer including gastrointestinal cancer, gastrointestinal stromal tumor, pancreatic cancer, head and neck cancer, glioblastoma, retinoblastoma, astrocytoma, thecomas, arrhenoblastomas, hepatoma, hematologic malignancies including non-Hodgkins lymphoma (NHL), multiple myeloma, myelodysplastic disorders, myeloproliferative disorders, chronic myelogenous leukemia, and acute hematologic malignancies, endometrial or uterine carcinoma, endometriosis, endometrial stromal sarcoma, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma, mast cell sarcoma, ovarian sarcoma, uterine sarcoma, melanoma, malignant mesothelioma, skin carcinomas, Schwannoma, oligodendroglioma, neuroblastomas, neuroectodermal tumor, rhabdomyosarcoma, osteogenic sarcoma, leiomyosarcomas, Ewing Sarcoma, peripheral primitive neuroectodermal tumor, urinary tract carcinomas, thyroid carcinomas, Wilm's tumor, as well as abnormal vascular proliferation associated with phakomatoses, edema (such as that associated with brain tumors), and Meigs' syndrome. In some cases, the cancer is melanoma. The cancerous conditions amenable for treatment include metastatic cancers. "Treatment" as used herein refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, reduction of any direct or indirect pathological consequences of the disease, decreasing the rate of disease progression, amelioration or palliation of the disease state, and remission or improved prognosis. In some embodiments, antibodies are used to delay development of a disease or disorder. In non-limiting examples, antibodies may be used to reduce the rate of tumor growth or reduce the risk of metastasis of a cancer.

"Treatment" as used herein refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, reduction of any direct or indirect pathological consequences of the disease, decreasing the rate of disease progression, amelioration or palliation of the disease state, and remission or improved prognosis. In some embodiments, antibodies of the invention are used to delay development of a disease or disorder. In non-limiting examples, antibodies may be used to reduce the rate of tumor growth or reduce the risk of metastasis of a cancer.

Antibodies or antibody fragments can be used either alone or in combination with other compositions in a therapy. For instance, an antibody or antibody fragment may be co-administered with chemotherapeutic agent(s) (including cocktails of chemotherapeutic agents), other cytotoxic agent(s), anti-angiogenic agent(s), cytokines, thrombotic agents, and/or growth inhibitory agent(s). Such combined therapies noted above include combined administration (where the two or more agents are included in the same or separate formulations), and separate administration, in which case, administration of the antibody can occur prior to, and/or following, administration of the adjunct therapy or therapies.

Combination therapy may be achieved by use of a single pharmaceutical composition that includes both agents, or by administering two distinct compositions at the same time, wherein one composition includes the antibody and the other includes the second agent(s).

The two therapies may be given in either order and may precede or follow the other treatment by intervals ranging from minutes to weeks. In embodiments where the other agents are applied separately, one would generally ensure that a significant period of time did not expire between the time of each delivery, such that the agents would still be able to exert an advantageously combined effect on the patient. In such instances, it is contemplated that one may administer both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

The antibodies and antibody fragments may also be administered in combination with radiotherapy, surgical therapy, immunotherapy (particularly radioimmunotherapy), gene therapy, or any other therapy known to those of ordinary skill in the art for treatment of a disease or disorder associated with vascular proliferation, such as any of the diseases or disorders discussed elsewhere in this specification.

G. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

In Vivo Tumor Growth Assessment 6-8 week old C57BL/6 were purchased form Taconic and used 5-7 days after arrival. On day 0 of the experimental protocol $2\times10^6$ B16-SIY-dsRed cells (expressing the model peptide SIYRYYGL (SEQ ID NO.: 1)) were injected subcutaneously (s.c.) into the right flank. Treatment regimens were initiated on day 4, post tumor inoculation, and carried out through day 16. Tumor growth was recorded every other day starting on day 7. Mice were sacrificed when either the tumor diameter reached 2 cm or the experimental end-point of day 35 was reached. Immune cells from tumor and spleen of were analyzed for the immune status by flow cytometry and ELISpot. See FIGS. 2-5.

TABLE 1

| Drug | Days of administration | Concentration | Route | Clone | Company |
|---|---|---|---|---|---|
| Anti-CTLA4 | Days 4, 7, 10 | 100 μg/dose | i.p. | UC10-4F10-11 | BioXcell |
| Anti-PD-L1 | Every other day (4-16) | 100 mg/dose | i.p. | 10F.9G2 | BioXcell |
| Anti-CD25 | Day 4 | 100 mg/dose | i.p. | PC-61.5.3 | BioXcell |
| IL-7 | Every day (4-15) | 8 ng/dose | s.c. (left flank) | | Peprotech |
| IDOi | Days 4-8 and 11-15 | 300 mg/g QD | Oral gavage | | Incyte |

Flow Cytometry

Figure 6:
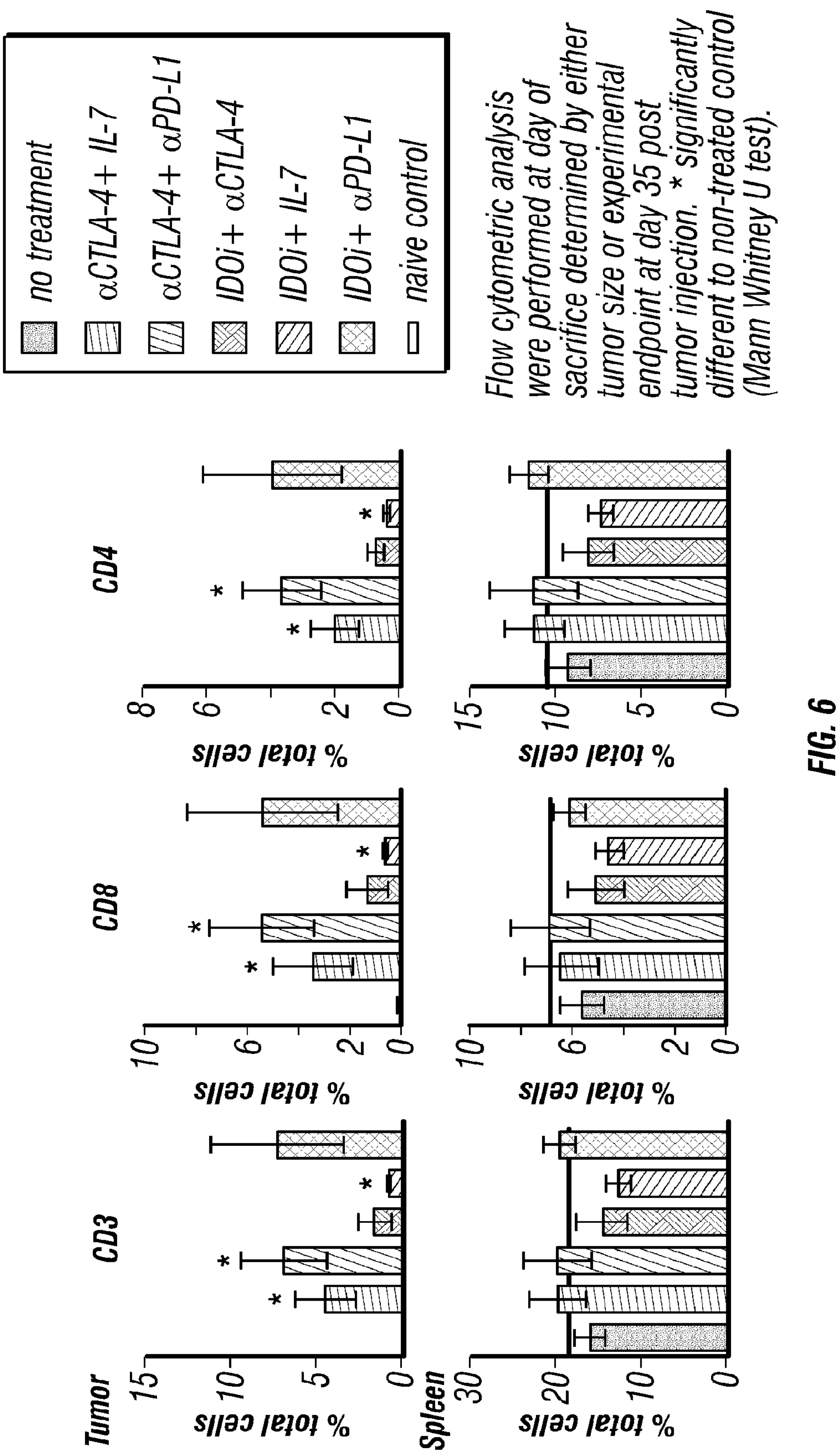
FIG. 6 illustrates the impact on T cell numbers. Flow cytometric analysis was performed at day of sacrifice determined by either tumor size or experimental endpoint at day 35 post-tumor injection. *significantly different to non-treated control (Mann Whitney U test).
Figure 6:
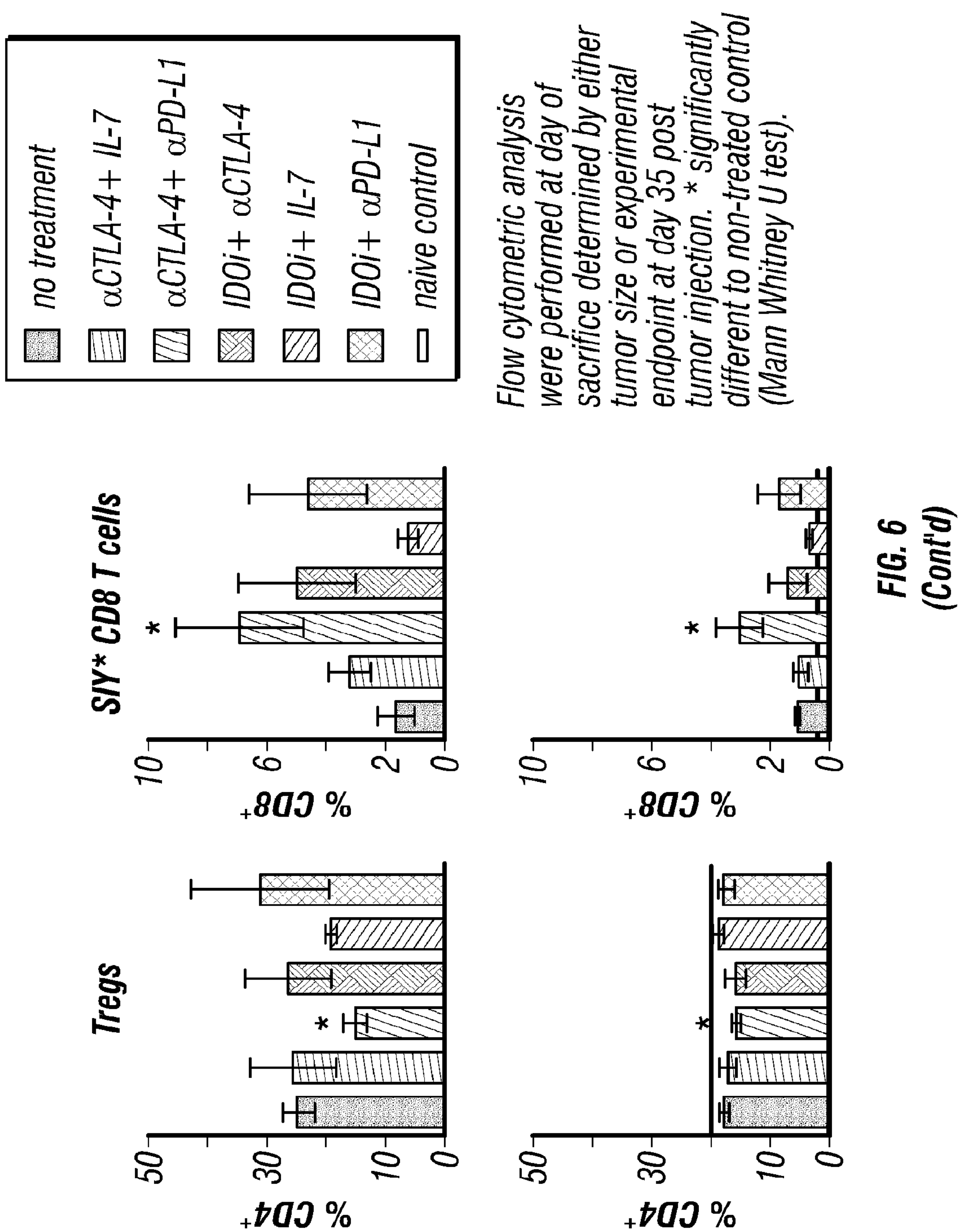

For flow cytometry analysis, spleens and tumors were isolated from mice, smashed, and single cell suspensions were prepared. Lymphocytes from tumor samples were enriched via a ficoll (BD) centrifugation step (450 g, 10 min., no break), and interphases were harvested and washed before used for staining procedure. Cells were stained with surface antibodies and multimer for 45 min in FACS Buffer at 4° C. (PBS, 10% FCS, 0.5 mM EDTA). Following staining with multimer, cells were fixed in 4% PFA (BD) for 30 minutes and kept until acquisition in 1% PFA. Samples stained for T cell markers were fixed using a FoxP3 staining kit (eBioscience®) and stained for FoxP3 according to manufacturer's instructions. Samples were acquired on the LSRII blue machine (BD) and the data was analyzed using FlowJo® (TrekStar®). The results are shown in FIG. 6.

TABLE 2

| | Clone | Conjugate | Company |
|---|---|---|---|
| Staining panel T cell marker | | | |
| CD3 | 17A2 | AlexaF ™ 700 | eBioscience ® |
| CD4 | RM4-5 | PerCP-Cy5.5 ™ | BioLegend ® |
| CD8 | 53-6.7 | APC-Cy7 ™ | BioLegend ® |
| CD44 | IM7 | FITC | BD ® |
| FoxP3 | FJK-16a | APC | eBioscience ® |
| Live/death dye | | PacificBlue ™ | eBioscience ® |
| Multimer panel | | | |
| CD3 | 17A2 | AlexaF ™ 700 | eBioscience ® |
| CD4 | RM4-5 | PerCP-Cy5.5 ™ | BioLegend ® |
| CD8 | 53-6.7 | APC-Cy7 ™ | BioLegend ® |
| CD45/B220 | RA3-6B2 | FITC | PharMingen ® |
| SIY Pentamer | | PE | Proimmune ® |
| Live/death dye | | PacificBlue ™ | eBioscience ® |

IFN-γ ELISpot.

For IFN-γ ELISpot (BD) analysis splenocytes were cryopreserved at a cell concentration of $2\times10^7$ cells/ml, collected until all mice from one experiments were available for analysis and thawed directly before initializing the assay. In the assay $2\times10^6$ cells were used per well and specific stimulation was performed using the SIY peptide (160 nM) loaded onto splenocytes directly. Medium only served as negative control while PMA/Ionomycin (2.5 μg/ml and 25 μg/ml final concentration, Sigma) stimulation was carried out as positive control. The assay itself was performed according to manufacturer's instructions and stimulation was performed for an 18 h period. The results are shown in FIG. 7.

Treatment Regimens.

Treatment was initiated on day 4 post tumor inoculation with the following regimens for each drug. αCTLA-4 antibody (clone UC10-4F10-11, Bio-X-Cell) was given i.p. on day 4, 7 and 10 at a dose of 100 μg/mouse. αPD-L1 antibody (clone 10F.9G2, Bio-X-Cell) was given i.p. (100 μg/mouse) every other day starting on day 4 ending on day 16 post tumor inoculation. IDOi (INCB23843, Incyte Corporation) was dissolved in 0.5% methylcellulose and administered at 300 mg/kg po QD on a 5 days on/2 days off schedule starting on day 4. In the case of functional experiments with an earlier endpoint, treatment regimens were carried out as described until the day of T cell analysis. A comparison between IDOi and IDOc (INCB24360, Incyte Corporation) was performed according to the treatment regime described above. Tumor outgrowth was followed starting day 7 onwards and is depicted in combination with anti-CTLA4 (FIG. 18A) or anti-PD-L1 (FIG. 18B). N=5 mice per group, and a two-way Anova test was used to determine significance between the groups.

Flow Cytometry and Antibodies.

For flow cytometric analysis, spleen, tumor-draining lymph node (TdLN), and tumor tissues were harvested at the indicated time point or when tumors reached a volume of 200 $mm^2$. Single cell suspensions were prepared and a Ficoll-Hypaque purification step was performed for the tumor-derived cell suspension. Following a washing step, approximately $2\times10^6$ cells were used for antibody staining. Antibodies against the following molecules were used if not otherwise indicated: CD3 (AF700, 17A2, eBioscience), CD4 (PerCP-Cy5.5, RM4-5, Biolegend), CD8 (APCCy7, 53-6.7, Biolegend), FoxP3 (APC, FJK-16a, eBioscience), IL-2 (PerCP, JES6-5H4, eBioscience), IFN-γ (APC, XMG1.2, eBioscience), and TNF-α (FITC, MP6-XT22, eBioscience). Fixable life/death discrimination was performed using PacBlue or AmCyan (eBioscience). Staining was carried out at RT for 30 min if not indicated differently and intracellular staining was performed using the FoxP3-staining kit according to manufacturer's instructions (BD).

Staining of SIY-specific cells was performed using the SIYRYYGL (SEQ ID NO.: 1)-pentamer (Proimmune®), conjugated with Phycoerythrin (PE), or as a non-specific control with the SIINFEKL (SEQ ID NO.: 2)-pentamer. For staining, pentamers were diluted 1:50 in PBS+10% FCS and incubated for 20 minutes at room temperature (RT). Following a washing step, cells were stained with specific antibodies for 30 minutes on ice prior to fixation in 4% PFA. All flow cytometric analyses were done using an LSR II blue instrument (BD®) and analyzed using FlowJo™ software (Tree Star).

Ex Vivo T Cell Functional Assays.

Single cell suspensions from tumor, spleen, and TdLN were prepared as described above. Cell numbers were determined and cells were labeled with Cell Trace (BD) according to manufacturer's instructions. A maximum of $1\times10^6$ cells was plated per well on either non-treated or anti-CD3 mAb-coated plates. Anti-CD3 mAb coating was performed with a solution of 10 μg/ml αCD3 antibody (145-2C11, Biolegend) in PBS, incubated overnight at 4° C. Following 48 h of incubation, cells were harvested and transferred onto newly anti-CD3-coated or non-treated plates, along with anti-CD28 mAb (2 μg/ml) (EL-4, Biolegend). Medium for all wells included 5 μg/ml BrefeldinA (Sigma). Following a 6 h incubation at 37° C., cells were harvested and stained for surface markers and intracellular cytokines using the technique described above.

Treatment with FTY720.

Prior to the initiation of the therapy regimens (2.5 h pre-treatment), fingolimod (FTY-720, Enzo Life Sciences) was given to mice to inhibit lymphocyte migration out of lymphoid organs. FTY-720 stock solution (10 mg/ml in DMSO) was diluted to a 125 μg/ml concentration in PBS directly before administration. Mice received a dose of 25 μg FTY-720 or PBS containing DMSO as control via oral gavage. Therapy was initiated the same day (2.5 h delayed) and mice were analyzed on day 7 to perform the ex vivo functional assay as described above.

In Vivo Proliferation Assay.

Assessment of in vivo proliferation was performed by Bromodeoxyuridine (BrdU) pulse in vivo, 24 h prior to flow cytometric analysis. Each mouse received 0.8 mg BrdU in 100 μl injected i.p. either on day 6 or day 13 of the treatment protocol. Mice were analyzed on day 7 or day 14, respectively, and cells were prepared for flow cytometry as described above. Following surface staining, cells were fixed using the FoxP3 staining kit (BD). After the 30 minute fixation period, cells were incubated in 100 μl of PBS/DNase solution (300 μg/ml) for 30 minutes at 37° C. Cells were then washed and incubated for 30 minutes at RT with antibodies for FoxP3 and BrdU (FITC, Bu20a, eBioscience) followed by flow cytometric analysis.

Combinational Blockade of CTLA-4, PD-L1 or IDO Pathways Results in Improved Tumor Control In Vivo.

Single blockade of the immune-inhibitory pathways CTLA-4, PD-1/PD-L1, or IDO has been shown to have modest yet significant impact on tumor growth kinetics and to improve tumor-specific immune responses in various mouse models in vivo. The effect of blocking multiple immune-inhibitory pathways on tumor control was investigated. On day 0, B16-SIY cells were inoculated subcutaneously in the flank of C57BL/6 mice. After allowing the tumor cells to engraft, therapy was initiated on day 4. The anti-CTLA-4 mAb (clone: UC10-4F10-11) was given at three single time points. The anti-PD-L1 mAb (clone: 10F.9G2) was given every other day throughout the treatment protocol, and the IDO inhibitor (IDOi, INCB23843) was given daily Monday-Friday via oral gavage. Treatment with single agents versus doublet combinations was compared, using tumor growth measured twice per week as the endpoint. For all three double treatments, improved tumor control was observed compared to the corresponding single regimens. In particular, the combination of αCTLA-4 and αPD-L1 resulted in 15 complete responders out of a total of 27 treated mice (55.5%; FIG. 9B). Lower numbers of complete responders were found for the combination of αCTLA-4 and IDOi (3/16; FIG. 9C) and improved tumor control was also seen with αPD-L1 and IDOi. Together, these results suggest that combinatorial targeting of CTLA-4+/−PD-L1+/−IDO could translate into a therapeutic advantage in vivo.

Effective Combination Therapies do not Substantially Increase the Frequency of Anti-Tumor $CD8^+$ T Cells in the Tumor-Draining Lymph Node at Early Time Points.

The mechanism by which improved immune-mediated tumor control was examined. To test whether successful doublet therapies were first improving the de novo priming of anti-tumor T cells in the tumor-draining lymph node which then subsequently home to tumor sites and improve tumor control, the frequency of SIY-specific $CD8^+$ T cells in the tumor-draining lymph node (TdLN) and in the spleen on day 7, using SIY-$K^b$ pentamer staining was assessed (FIGS. 10A-B). However, only minimal increases in frequencies of tumor-specific $CD8^+$ T cells were observed. The functional capacity of these cells was further assessed by IFN-γ ELISpot (FIG. 10C). No major differences were detected between treatment groups. Only αCTLA-4+αPD-L1 and αCTLA-4+IDOi showed a statistically significant difference compared to no treatment (p=0.0263 and p=0.0101) as well as to their respective single treatments (αCTLA-4+αPD-L to αPD-L1 p=0.0172; αCTLA-4+IDOi to αCTLA-4 p=0.0185). However, this difference did not seem sufficient to account for the major improvement in tumor control observed.

Effective Doublets Result in Increased Frequency of IL-2-Producing and Proliferating Polyfunctional T Cells within the Tumor.

In order to assess whether the therapeutic effect was a result of reactivation of tumor-infiltrating $CD8^+$ T cells, an ex vivo stimulation protocol which is designed to favor analysis of pre-activated T cells was utilized. Responsiveness was assessed by measuring proliferation (cell trace dilution) as well as production of IL-2, IFN-γ and TNF-α by intracellular cytokine staining. As depicted in a representative flow cytometric plot in FIG. 11A, only the therapeutic effective doublet treatments showed a detectable proliferation rate of $CD8^+$ T cells in combination with IL-2 production, and the magnitude of this effect was striking (non-stimulated control shown in FIG. 12A). A statistical analysis of data spanning two independent experiments confirmed that significant ex vivo proliferation was only observed in stimulated T cells from mice that received the effective doublets (FIG. 11B). Modest increases in both IFN-γ and TNF-α production were also seen; however, high production of these cytokines by tumor-infiltrating $CD8^+$ T cells was already observed without treatment. Looking further at IFN-γ-producing cells in the doublet treatment groups, most IFN-γ-producing T cells were positive for IL-2 production and showed significantly increased proliferation (FIG. 11C), while single treatment groups showed mainly IFN-γ-single producing cells. Comparing the stimulated cells to non-stimulated controls confirmed that only the double treatments were able to show increased IL-2 production and proliferation above background levels (FIG. 12B). These T cells also produced TNF-α, indicating a polyfunctional T cell phenotype (FIG. 11D). Detection of cytokine production was dependent on re-stimulation in vitro (FIG. 12B). Thus, all three effective immunotherapy doublets resulted in the same improved functional effect: restoration of IL-2 production and proliferation by $CD8^+$ intratumoral T cells, along with augmented polyfunctionality.

Increased Frequency of Polyfunctional T Cells within the Tumor does not Require New T Cell Migration.

To determine whether the presence of $CD8^+$ T cells showing high levels of IL-2 production and proliferation within the tumor microenvironment following effective immunotherapy doublets was a result of new T cell migration into the tumor site or re-activation of T cells already present, FTY720 treatment was utilized to block the sphingosine 1-phosphate receptor-1 and thereby prohibit T cells from exiting lymphoid organs. Previous studies have shown that the effect can be detected as soon as 2 h after initial administration and is stable for up to 4 days. FTY720 was administered or control vehicle to tumor-bearing mice on day 4, 2.5 h prior to the initiation of immunotherapies. To control for effective depletion of circulating T cells the number of $CD3^+$ cells in the peripheral blood was assessed. Overall, a 90% reduction in circulating $CD3^+$ T cells in FTY720-treated mice was detected (FIG. 13A).

The effect of intratumoral $CD8^+$ T cells on IL-2 production and proliferation restoration was examined. Comparing vehicle-treated groups (open bars) to the FTY720-treated groups (filled bars) a similar increase in proliferation and IL-2 production was observed (FIGS. 13B-C), although there were some subtle differences. A modest reduction of proliferated/IL-$2^+$-cells could be detected after αCTLA-4+IDOi treatment and a modest increase could be observed when mice were treated with αPD-L1+IDOi (p=0.0286) (FIG. 13C). Nevertheless, these data strongly suggest that the major mechanism for improved T cell function within the tumor microenvironment following these effective immunotherapies is through a direct effect on $CD8^+$ T cells already present in the tumor site.

Immunotherapy doublet therapy was employed to examine the effect on proliferation of tumor-infiltrating T cells. A short pulse of BrdU administration in vivo was used. To this end, a single dose of BrdU was administered i.p. on day 6 and proliferation of T cells in the tumor (FIG. 14), spleen and TdLN (FIG. 15) was assessed on day 7. Consistent with the ex vivo results, the doublet-treated mice harbored more proliferating $CD8^+$ T cells in the tumor site than did the single-treated groups or the mice that received no treatment (FIG. 14A). A similar effect was also seen for $CD4^+$ T cells, with the exception that αCTLA4mAb single treatment also resulted in an increased proliferation rate in this cell compartment (FIG. 14B). Taken together, these data indicate that the therapeutically successful combination therapies of anti-CTLA-4+/− anti-PD-L1+/− an IDOi resulted in increased proliferation and reactivation of $CD8^+$ T cells directly within the tumor site.

Combinatorial Treatments Lead to Prolonged Persistence and Higher Frequency of Tumor-Reactive Lymphocytes in the Periphery at Later Time Points.

Figure 16:
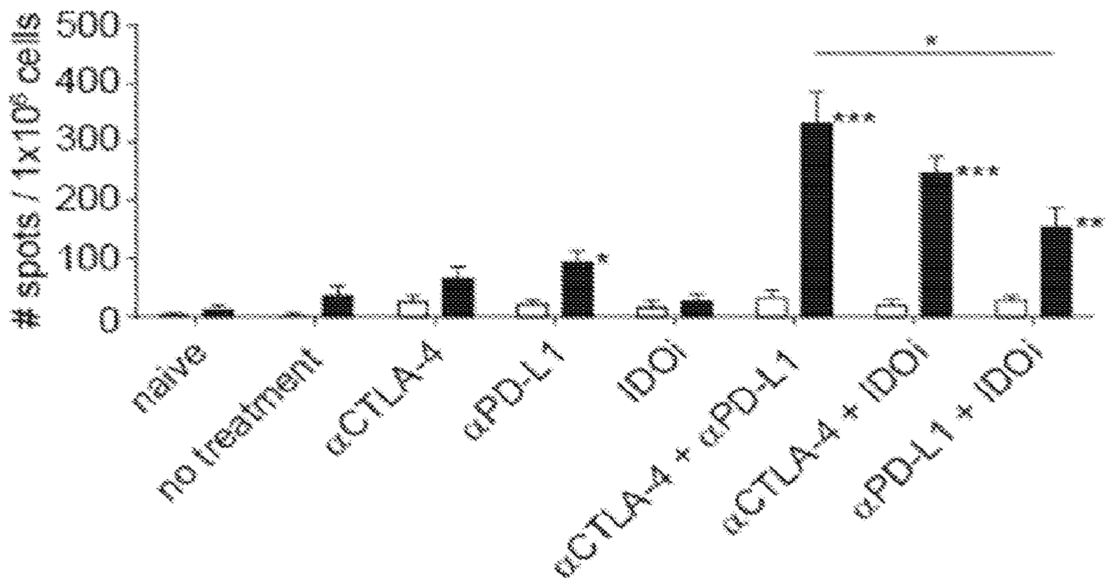
FIG. 16 illustrates immunotherapy doublets that result in increased frequencies of tumor antigen-specific T cells at later time points in the periphery. Depicted is an IFN-γ ELISpot of splenocytes harvested on day 14 with open bars being the un-stimulated control and filled bars representing SIY-stimulation.
Figure 17:
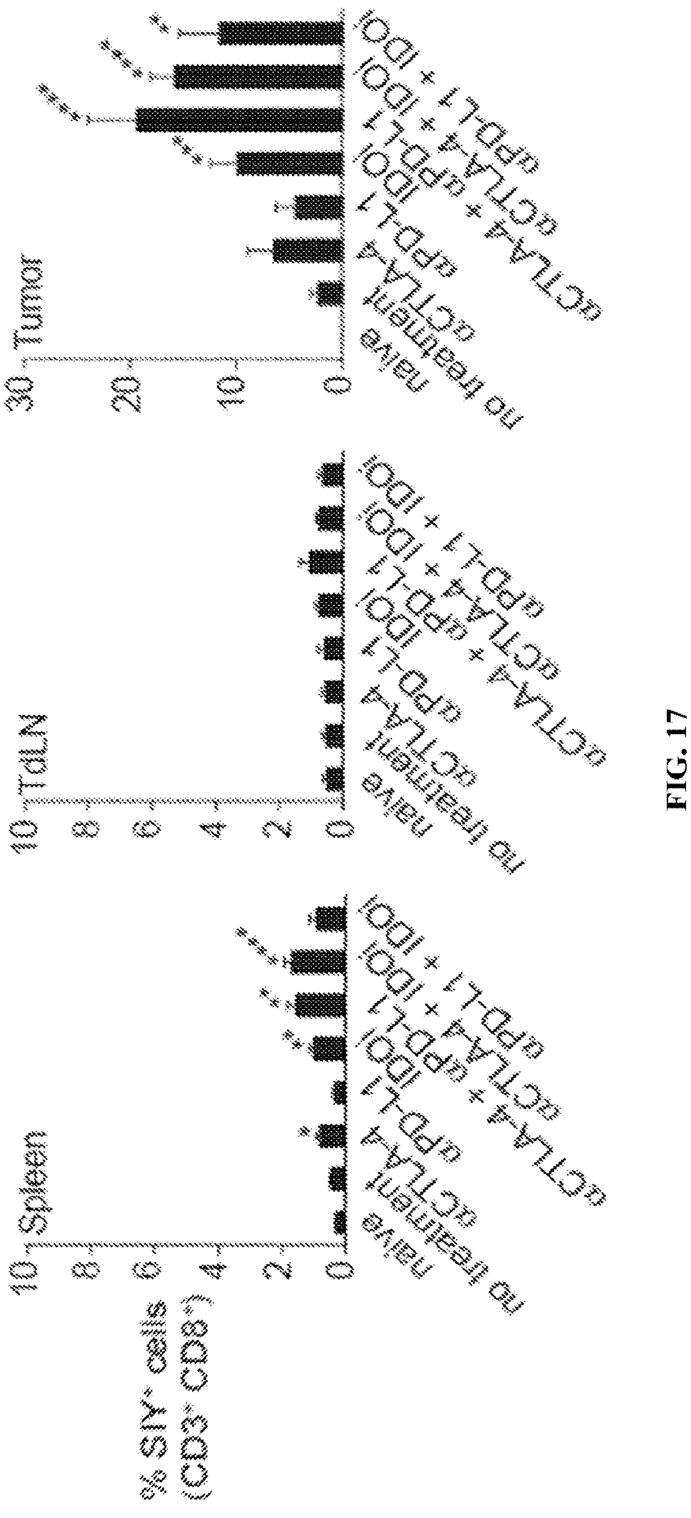
FIG. 17 demonstrates immunotherapy doublets increase frequency and persistence of SIY/$K^b$ pentamer-specific T cells in the periphery and in the tumor.

To test if combinatorial treatment restored T cell function within the tumor site, and led to anti-tumor T cell recirculation in the periphery, functional SIY-specific T cells were assayed for in the spleen on day 14 (FIG. 16). Indeed, a significant increase in the frequency of IFN-γ-producing T cells upon SIY stimulation was observed when comparing the double treatments to the single treatment or no treatment groups. All three of the double treatment groups show an increase in SIY-reactive cells by 2- to even 3.5-fold higher levels compared to day 7. This effect was accompanied by increased frequency of SIY-pentamer positive $CD8^+$ T cells in the spleen, and also within the tumor (FIG. 17). Consistent with these results, re-challenge of mice 6 weeks later that rejected the first tumor were protected against B16.SIY (Table 3). Thus, the successful doublet treatments eventually led to a higher circulating fraction of tumor antigen-specific T cells that likely represents a memory response.

TABLE 3

| treatment | # mice | # complete rejection | # rechallenged | # protective response |
|---|---|---|---|---|
| αCTLA-4 | 37 | 0 | 0 | 0 |
| αPD-L1 | 31 | 0 | 0 | 0 |
| IDOi | 26 | 0 | 0 | 0 |
| αCTLA-4 + αPD-L1 | 27 | 15 | 5 | 4 |

TABLE 3-continued

| treatment | # mice | # complete rejection | # rechallenged | # protective response |
|---|---|---|---|---|
| αCTLA-4 + IDOi | 16 | 3 | 3 | 2 |
| αPD-L1 + IDOi | 10 | 1 | 1 | 0 |

Mice with a complete rejection of the tumor after therapy were rechallenged with 2 × $10^6$ B16-SIY cells 4 weeks after therapy was ended.
Tumor growth was followed up to 8 weeks after rechallenge Pairwise Combinations of αCTLA-4, αPD-L1 or IDOi Blockade Results in Retarded Tumor Outgrowth.

αCTLA-4 was administered on day 4, 7, 10 i.p., αPD-L1 on day 4, 6, 8, 10, 12, 14, 16 i.p. and IDOi was given every day via oral gavage Monday-Friday. Tumor outgrowth measured in $mm^2$ comparing the single treatment to the respective combined double treatment of αCTLA-4 and αPD-L1 C (FIG. 9A), αCTLA-4 and IDOi (FIG. 9B), and αPD-L1 and IDOi (FIG. 9C). Depicted are means+/−SEM of 6 mice from one representative experiment. All experiments were at least done twice with the same overall result. Significance to the single treatments was tested using a two-way-Anova with Bonferroni post-test and is shown in the figure while all treatments regimes were significantly different to the no treatment control (**<0.0001, <0.01).

Pairwise Combinations of αCTLA-4 or αPD-L1 with Either IDOi (INCB23843) or IDOc (INCB24360) Blockade Results in Similar Tumor Outgrowth Retardation.

Treatment was administered in the same fashion as described for FIG. 9, with the exception that IDOi (INCB23843) was replaced by IDOc (INCB24360) in the indicated groups. FIG. 18A shows combination of IDOi and IDOc with αCTLA-4 and FIG. 18B depicts combinations of IDOi and IDOc with αPD-L1. Shown are means+/−SEM of 5 mice per group from a representative experiment and significance was determined using a two-way-Anova with Bonferroni post-test (**<0.0001, *<0.001, **<0.01, n.s.=not significantly different).

Unaffected Fraction Analysis of the Combination Therapies Demonstrates Synergy.

Synergy analysis was performed with day 15 data and with day 23 data. Actual tumor growth inhibition (TGI) is the experimental TGI seen in this experiment for the combinations, and predicted TGI is the TGI that would have been expected for a purely additive combination effect from the performance of the individual agents in this experiment. Actual TGIs higher than predicted TGIs reflect better than additive (synergistic) data. Table 4. demonstrates that IDOi+αCTLA4, IDOi+αPDL1, IDOc+αCTLA4 and IDOc+αPDL-1 are synergistic treatments.

TABLE 4

| | Day 15 (end of dosing) | | Day 23 (last day of vehicles) | |
|---|---|---|---|---|
| IDOc (INCB24360) | anti CTLA4 | antiPDL1 | anti CTLA4 | antiPDL1 |
| Actual TGI | 74% | 81% | 93% | 82% |
| Predicted TGI | 66% | 24% | 65% | 35% |

TABLE 4-continued

| | Day 15 (end of dosing) | | Day 23 (last day of vehicles) | |
|---|---|---|---|---|
| IDOi (INCB23843) | anti CTLA4 | antiPDL1 | anti CTLA4 | antiPDL1 |
| Actual TGI | 75% | 88% | 87% | 78% |
| Predicted TGI | 69% | 31% | 67% | 39% |

Double Regimen Therapy does not Result in Substantially Increased Frequency of Tumor-Reactive T Cells at Early Time Points in the Periphery.

Peptide/$K^b$ pentamer staining was performed on gated CD3+CD8+ T cells, isolated from TdLN (FIG. 10A) or spleen (FIG. 10B) on day 7. Shown are means+/−SEM of a total of 10 mice collected from two experiments. For statistical analysis, Mann-Whitney-U test was performed comparing single treatments to double treatments (*=0.0317 αCTLA-4 to αCTLA-4+αPD-L1 in spleen). None of the other treatments was significantly different to the no treatment control. IFN-γ ELISpot was performed on splenocytes collected on day 7 (FIG. 10C). Data are shown as mean+/−SEM from 10 mice out of two experiments with no stimulation as open bar and SIY-specific stimulation as filled bar. The Mann-Whitney-U test was used to assess significant differences between no treatment group and treatment regimens with * in the figure indicating significant difference compared to no treatment. Results with αCTLA-4 were significantly different to αCTLA-4+IDOi (p=0.0185) and αPD-L1 was significantly different to αCTLA-4+αPD-L1 (p=0.0172).

Double Treatments Restore Capacity of Lymphocytes within the Tumor to Produce IL-2 and Proliferate.

Tumors were harvested on day 7 and single cell suspensions were prepared. Pools of cells from 3-5 mice were combined and subsequently stained with cell trace. Cells were cultured with or without plate-bound anti-CD3 for 48 h then treated with anti-CD3/anti-CD28-stimulation in the presence of Brefeldin A for 6 h. Cells were then stained for production of IL-2, IFN-γ and TNF-α by intracellular flow cytometry. A representative FACS plot showing proliferation via cell trace dilution on the x-axis and intracellular IL-2 staining on the y-axis (FIG. 11A). A pool of five mice was analyzed (FIG. 11B). Statistical analysis of the amount of proliferating $CD3^+CD8^+$ cells in the non-stimulated (left) and stimulated (right) group. Only double treatments show a significant increase in proliferation compared to non-stimulated and single treatments when tested with a one-way Anova. Bars represent mean+/−SEM of a total of 4 pools collected out of 2 experiments. The percentages of IFN-$\gamma^+$ (open bar), IFN-$\gamma^+$ and IL-$2^+$ (gray bar), and proliferating IFN-$\gamma^+$IL-$2^+$ cells (filled bar) were calculated within the $CD3^+CD8^+$ cell population (FIG. 11C).

Restoration of IL-2 Production and Proliferation of Tumor-Infiltrating Lymphocytes in the Absence of New T Cell Migration.

B16-SIY bearing mice were either treated with FTY720 or control vehicle prior to initiation of therapy, to prevent migration of new lymphocytes into the tumor. Peripheral blood T cell numbers following FTY720 treatment on the day of tumor harvest for analysis. Open bars depict the number of $CD45^+CD3^+$ T cells detected in 200 ul peripheral blood of vehicle treated mice set to 100%. Filled bars represent the number found in FTY720-treated mice, relative to the vehicle-treated group (FIG. 13A). Single cell suspensions from tumor were labeled with cell trace and stimulated with plate-bound anti-CD3 antibody for 48 h prior then with anti-CD3 and anti-CD28 in the presence of Brefeldin A. Cells were then analyzed for proliferation by cell trace dilution and production of IL-2 via intracellular staining. Depicted are the percentages of proliferating cells (FIG. 13B) or proliferating and IL-2 producing cells (FIG. 13C) comparing vehicle-treated groups (open bar) to FTY720-treated groups (filled bar). Results are shown as the mean+/−SEM combining two experiments with each having 2 pools of 3 mice. Significance was tested using Mann-Whitney-U test but no significant change between FTY720 and vehicle control could be detected except for increased IL-2 production in the αPD-L1+IDOi treatment group (p=0.02).

Immunotherapy Doublets Result in Increased BrdU Incorporation by CD8+ and CD4+ Tumor-Infiltrating T Cells In Vivo.

Tumor-infiltrating lymphocytes were harvested on day 7, 24 h after a single BrdU pulse in vivo, and cells were stained for BrdU along with anti-CD3, anti-CD4, and anti-CD8. Depicted are percentages of $BrdU^+$ cells that were $CD3^+$ $CD8^+$ (FIG. 14A) and $CD3^+$ $CD4^+$ (FIG. 14B). Data shown present the mean of a total of 5 mice from one experiment and are representative of two independent experiments. Differences were assessed using a two-way Anova test and taking proliferation values from spleen and TdLN into account. * indicates significantly different to no treatment and all double treatments were significantly different to their corresponding single treatments with the exception of αCTLA-4 to both double treatments for CD4 T cell proliferation.

In Vivo Proliferation of CD8+ and CD4+ Positive T Cells in Spleen and TdLN.

To contrast to the increased BrDU incorporation observed among T cells in the tumor, BrdU staining was performed on cells from spleen and TdLN and analyzed side by side to the staining shown in FIGS. 14A-B. Bars represent the mean+/−SEM out of a total of 10 mice. No differences were significant. The results are shown in FIG. 15.

Immunotherapy Doublets Result in Increased Frequencies of Tumor Antigen-Specific T Cells at Later Time Points in the Periphery.

Depicted is an IFN-γ ELISpot of splenocytes harvested on day 14 with open bars being the un-stimulated control and filled bars representing SIY-stimulation. Data are shown as the mean+/−SEM from 10 mice pooled from two experiments. Statistical analysis was done using Mann-Whitney-U test comparing all groups to no treatment. All double treatment groups were significantly different to their respective single treatment and when comparing double treatments within each other a significant difference between αCTLA4+αPD-L1 and αPD-L1+IDOi was observed. The results are shown in FIG. 16.

Immunotherapy Doublets Result in Increased Frequency and Longer Persistence of SIY/$K^b$ Pentamer-Specific T Cells in the Periphery and in the Tumor.

Pentamer staining was performed on gated $CD3^+CD8^+$ T cells, isolated from spleen, TdLN or tumor on day 14. Shown are means+/−SEM of a total of 10 mice collected from two experiments. For statistical analysis, Mann-Whitney-U test was performed comparing all treatments to the no treatment control (indicated by *). The following combinations were significantly different in the spleen: αCTLA4 to αCTLA4+αPD-L1 and αCTLA4+IDOi; αPD-L1 to αCTLA4+αPD-L1 and αPD-L1+IDOi; IDOi to αCTLA4+IDOi; and in the tumor: αCTLA4 to αCTLA4+αPD-L1 and αCTLA4+IDOi; αPD-L1 to αCTLA4+αPD-L1; IDOi to αCTLA4+IDOi. The results are shown in FIG. 17.

Doublet therapies using either anti-CTLA-4, anti-PD-L1 and/or IDOi show a synergistic retardation of tumor outgrowth in vivo. The major biologic correlate to this improved efficacy was restored IL-2 production and proliferation of tumor-infiltrating CD8+ T cells. In addition, this functional restoration does not require new T cell migration as assessed using FTY720 administration. Successful combination immunotherapies function, at least in part, by correcting functional defects of T cells directly within the tumor microenvironment.

CD8+ TILs without any therapy showed significant production of IFN-γ production when analyzed ex vivo. Consistent with this observation, human melanoma metastases showing a T cell-infiltrated phenotype usually show expression of IFN-γ-induced target genes and in many cases IFN-γ itself. IFN-γ produced by CD8+ T cells is necessary for the induction of the negative regulatory factors PD-L1 and IDO within the tumor microenvironment. Thus, the retained ability of TIL to produce at least some IFN-γ may in fact contribute to the negative regulatory network within the tumor site that enable tumor immune evasion.

Example 1

4-({2-[(Aminosulfonyl)amino]ethyl}amino)-N-(3-bromo-4-fluorophenyl)-N'-hydroxy-1,2,5-oxadiazole-3-carboximidamide

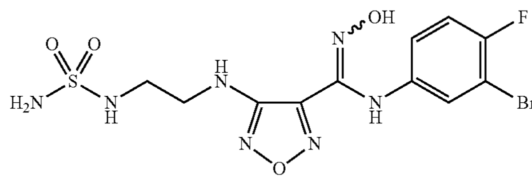

Step 1: 4-Amino-N'-hydroxy-1,2,5-oxadiazole-3-carboximidamide

Malononitrile (320.5 g, 5 mol) was added to water (7 L) preheated to 45° C. and stirred for 5 min. The resulting solution was cooled in an ice bath and sodium nitrite (380 g, 5.5 mol) was added. When the temperature reached 10° C., 6 N hydrochloric acid (55 mL) was added. A mild exothermic reaction ensued with the temperature reaching 16° C. After 15 min the cold bath was removed and the reaction mixture was stirred for 1.5 hrs at 16-18° C. The reaction mixture was cooled to 13° C. and 50% aqueous hydroxylamine (990 g, 15 mol) was added all at once. The temperature rose to 26° C. When the exothermic reaction subsided the cold bath was removed and stirring was continued for 1 hr at 26-27° C., then it was slowly brought to reflux. Reflux was maintained for 2 hrs and then the reaction mixture was allowed to cool overnight. The reaction mixture was stirred in an ice bath and 6 N hydrochloric acid (800 mL) was added in portions over 40 min to pH 7.0. Stirring was continued in the ice bath at 5° C. The precipitate was collected by filtration, washed well with water and dried in a vacuum oven (50° C.) to give the desired product (644 g, 90%). LCMS for $C_3H_6N_5O_2(M+H)^+$: m/z=144.0. $^{13}C$ NMR (75 MHz, $CD_3OD$): δ 156.0, 145.9, 141.3.

Step 2:
4-Amino-N-hydroxy-1,2,5-oxadiazole-3-carboximidoyl chloride

4-Amino-N'-hydroxy-1,2,5-oxadiazole-3-carboximidamide (422 g, 2.95 mol) was added to a mixture of water (5.9 L), acetic acid (3 L) and 6 N hydrochloric acid (1.475 L, 3 eq.) and this suspension was stirred at 42-45° C. until complete solution was achieved. Sodium chloride (518 g, 3 eq.) was added and this solution was stirred in an ice/water/methanol bath. A solution of sodium nitrite (199.5 g, 0.98 eq.) in water (700 mL) was added over 3.5 hrs while maintaining the temperature below 0° C. After complete addition stirring was continued in the ice bath for 1.5 hrs and then the reaction mixture was allowed to warm to 15° C. The precipitate was collected by filtration, washed well with water, taken in ethyl acetate (3.4 L), treated with anhydrous sodium sulfate (500 g) and stirred for 1 hr. This suspension was filtered through sodium sulfate (200 g) and the filtrate was concentrated on a rotary evaporator. The residue was dissolved in methyl t-butyl ether (5.5 L), treated with charcoal (40 g), stirred for 40 min and filtered through Celite®. The solvent was removed in a rotary evaporator and the resulting product was dried in a vacuum oven (45° C.) to give the desired product (256 g, 53.4%). LCMS for C3H4ClN4O2 (M+H)+: m/z=162.9. 13C NMR (100 MHz, CD3OD): δ 155.8, 143.4, 129.7.

Step 3: 4-Amino-N'-hydroxy-N-(2-methoxyethyl)-1,2,5-oxadiazole-3-carboximidamide 4-Amino-N-hydroxy-1,2,5-oxadiazole-3-carboximidoyl chloride (200.0 g, 1.23 mol) was mixed with ethyl acetate (1.2 L). At 0-5° C. 2-methoxyethylamine [Aldrich, product #143693] (119.0 mL, 1.35 mol) was added in one portion while stirring. The reaction temperature rose to 41° C. The reaction was cooled to 0-5° C. Triethylamine (258 mL, 1.84 mol) was added. After stirring 5 min, LCMS indicated reaction completion. The reaction solution was washed with water (500 mL) and brine (500 mL), dried over sodium sulfate, and concentrated to give the desired product (294 g, 119%) as a crude dark oil. LCMS for $C_6H_{12}N_5O_3$ $(M+H)^+$: m/z=202.3. $^1$H NMR (400 MHz, DMSO-$d_6$): δ 10.65 (s, 1H), 6.27 (s, 2H), 6.10 (t, J=6.5 Hz, 1H), 3.50 (m, 2H), 3.35 (d, J=5.8 Hz, 2H), 3.08 (s, 3H).

Step 4: N'-Hydroxy-4-[(2-methoxyethyl)amino]-1,2,5-oxadiazole-3-carboximidamide

4-Amino-N'-hydroxy-N-(2-methoxyethyl)-1,2,5-oxadiazole-3-carboximidamide (248.0 g, 1.23 mol) was mixed with water (1 L). Potassium hydroxide (210 g, 3.7 mol) was added. The reaction was refluxed at 100° C. overnight (15 hours). TLC with 50% ethyl acetate (containing 1% ammonium hydroxide) in hexane indicated reaction completed (product Rf=0.6, starting material Rf=0.5). LCMS also indicated reaction completion. The reaction was cooled to room temperature and extracted with ethyl acetate (3×1 L). The combined ethyl acetate solution was dried over sodium sulfate and concentrated to give the desired product (201 g, 81%) as a crude off-white solid. LCMS for $C_6H_{12}N_5O_3$ $(M+H)^+$: m/z=202.3 $^1$H NMR (400 MHz, DMSO-$d_6$): δ 10.54 (s, 1H), 6.22 (s, 2H), 6.15 (t, J=5.8 Hz, 1H), 3.45 (t, J=5.3 Hz, 2H), 3.35 (m, 2H), 3.22 (s, 3H).

Step 5: N-Hydroxy-4-[(2-methoxyethyl)amino]-1,2,5-oxadiazole-3-carboximidoyl chloride At room temperature N'-hydroxy-4-[(2-methoxyethyl)amino]-1,2,5-oxadiazole-3-carboximidamide (50.0 g, 0.226 mol) was dissolved in 6.0 M hydrochloric acid aqueous solution (250 mL, 1.5 mol). Sodium chloride (39.5 g, 0.676 mol) was added followed by water (250 mL) and ethyl acetate (250 mL). At 3-5° C. a previously prepared aqueous solution (100 mL) of sodium nitrite (15.0 g, 0.217 mol) was added slowly over 1 hr. The reaction was stirred at 3-8° C. for 2 hours and then room temperature over the weekend. LCMS indicated reaction completed. The reaction solution was extracted with ethyl acetate (2×200 mL). The combined ethyl acetate solution was dried over sodium sulfate and concentrated to give the desired product (49.9 g, 126%) as a crude white solid. LCMS for $C_6H_{10}ClN_4O_3$ $(M+H)^+$: m/z=221.0. $^1$H NMR (400 MHz, DMSO-$d_6$): δ 13.43 (s, 1H), 5.85 (t, J=5.6 Hz, 1H), 3.50 (t, J=5.6 Hz, 2H), 3.37 (dd, J=10.8, 5.6 Hz, 2H), 3.25 (s, 3H).

Step 6: N-(3-Bromo-4-fluorophenyl)-N'-hydroxy-4-[(2-methoxyethyl)amino]-1,2,5-oxadiazole-3-carboximidamide N-Hydroxy-4-[(2-methoxyethyl)amino]-1,2,5-oxadiazole-3-carboximidoyl chloride (46.0 g, 0.208 mol) was mixed with water (300 mL). The mixture was heated to 60° C. 3-Bromo-4-fluoroaniline [Oakwood products, product #013091] (43.6 g, 0.229 mol) was added and stirred for 10 min. A warm sodium bicarbonate (26.3 g, 0.313 mol) solution (300 mL water) was added over 15 min. The reaction was stirred at 60° C. for 20 min. LCMS indicated reaction completion. The reaction solution was cooled to room temperature and extracted with ethyl acetate (2×300 mL). The combined ethyl acetate solution was dried over sodium sulfate and concentrated to give the desired product (76.7 g, 98%) as a crude brown solid. LCMS for $C_{12}H_{14}BrFN_5O_3$ $(M+H)^+$: m/z=374.0, 376.0. $^1$H NMR (400 MHz, DMSO-$d_6$): δ 11.55 (s, 1H), 8.85 (s, 1H), 7.16 (t, J=8.8 Hz, 1H), 7.08 (dd, J=6.1, 2.7 Hz, 1H), 6.75 (m, 1H), 6.14 (t, J=5.8 Hz, 1H), 3.48 (t, J=5.2 Hz, 2H), 3.35 (dd, J=10.8, 5.6 Hz, 2H), 3.22 (s, 3H).

Step 7: 4-(3-Bromo-4-fluorophenyl)-3-{4-[(2-methoxyethyl)amino]-1,2,5-oxadiazol-3-yl}-1,2,4-oxadiazol-5(4H)-one A mixture of N-(3-bromo-4-fluorophenyl)-N'-hydroxy-4-[(2-methoxyethyl)amino]-1,2,5-oxadiazole-3-carboximidamide (76.5 g, 0.204 mol), 1,1'-carbonyldiimidazole (49.7 g, 0.307 mol), and ethyl acetate (720 mL) was heated to 60° C. and stirred for 20 min. LCMS indicated reaction completed. The reaction was cooled to room temperature, washed with 1 N HCl (2×750 mL), dried over sodium sulfate, and concentrated to give the desired product (80.4 g, 98%) as a crude brown solid. LCMS for $C_{13}H_{12}BrFN_5O_4$ $(M+H)^+$: m/z=400.0, 402.0. $^1$H NMR (400 MHz, DMSO-$d_6$): δ 7.94 (t, J=8.2 Hz, 1H), 7.72 (dd, J=9.1, 2.3 Hz, 1H), 7.42 (m, 1H), 6.42 (t, J=5.7 Hz, 1H), 3.46 (t, J=5.4 Hz, 2H), 3.36 (t, J=5.8 Hz, 2H), 3.26 (s, 3H).

Step 8: 4-(3-Bromo-4-fluorophenyl)-3-{4-[(2-hydroxyethyl)amino]-1,2,5-oxadiazol-3-yl}-1,2,4-oxadiazol-5(4H)-one 4-(3-Bromo-4-fluorophenyl)-3-{4-[(2-methoxyethyl)amino]-1,2,5-oxadiazol-3-yl}-1,2,4-oxadiazol-5(4H)-one (78.4 g, 0.196 mol) was dissolved in dichloromethane (600 mL). At −67° C. boron tribromide (37 mL, 0.392 mol) was added over 15 min. The reaction was warmed up to −10° C. in 30 min. LCMS indicated reaction completed. The reaction was stirred at room temperature for 1 hour. At 0-5° C. the reaction was slowly quenched with saturated sodium bicarbonate solution (1.5 L) over 30 min. The reaction temperature rose to 25° C. The reaction was extracted with ethyl acetate (2×500 mL, first extraction organic layer is on the bottom and second extraction organic lager is on the top). The combined organic layers were dried over sodium sulfate and concentrated to give the desired product (75 g, 99%) as a crude brown solid. LCMS for $C_{12}H_{10}BrFN_5O_4$ $(M+H)^+$: m/z=386.0, 388.0. $^1H$ NMR (400 MHz, DMSO-$d_6$): δ 8.08 (dd, J=6.2, 2.5 Hz, 1H), 7.70 (m, 1H), 7.68 (t, J=8.7 Hz, 1H), 6.33 (t, J=5.6 Hz, 1H), 4.85 (t, J=5.0 Hz, 1H), 3.56 (dd, J=10.6, 5.6 Hz, 2H), 3.29 (dd, J=11.5, 5.9 Hz, 2H).

Step 9: 2-({4-[4-(3-Bromo-4-fluorophenyl)-5-oxo-4,5-dihydro-1,2,4-oxadiazol-3-yl]-1,2,5-oxadiazol-3-yl}amino)ethyl methanesulfonate To a solution of 4-(3-bromo-4-fluorophenyl)-3-{4-[(2-hydroxyethyl)amino]-1,2,5-oxadiazol-3-yl}-1,2,4-oxadiazol-5(4H)-one (1.5 kg, 3.9 mol, containing also some of the corresponding bromo-compound) in ethyl acetate (12 L) was added methanesulfonyl chloride (185 mL, 2.4 mol) dropwise over 1 h at room temperature. Triethylamine (325 mL, 2.3 mol) was added dropwise over 45 min, during which time the reaction temperature increased to 35° C. After 2 h, the reaction mixture was washed with water (5 L), brine (1 L), dried over sodium sulfate, combined with 3 more reactions of the same size, and the solvents removed in vacuo to afford the desired product (7600 g, quantitative yield) as a tan solid. LCMS for $C_{13}H_{11}BrFN_5O_6SNa$ $(M+Na)^+$: m/z=485.9, 487.9. $^1H$ NMR (400 MHz, DMSO-$d_6$): δ 8.08 (dd, J=6.2, 2.5 Hz, 1H), 7.72 (m, 1H), 7.58 (t, J=8.7 Hz, 1H), 6.75 (t, J=5.9 Hz, 1H), 4.36 (t, J=5.3 Hz, 2H), 3.58 (dd, J=11.2, 5.6 Hz, 2H), 3.18 (s, 3H).

Step 10: 3-{4-[(2-Azidoethyl)amino]-1,2,5-oxadiazol-3-yl}-4-(3-bromo-4-fluorophenyl)-1,2,4-oxadiazol-5(4H)-one To a solution of 2-({4-[4-(3-bromo-4-fluorophenyl)-5-oxo-4,5-dihydro-1,2,4-oxadiazol-3-yl]-1,2,5-oxadiazol-3-yl}amino)ethyl methanesulfonate (2.13 kg, 4.6 mol, containing also some of the corresponding bromo-compound) in dimethylformamide (4 L) stirring in a 22 L flask was added sodium azide (380 g, 5.84 mol). The reaction was heated at 50° C. for 6 h, poured into ice/water (8 L), and extracted with 1:1 ethyl acetate:heptane (20 L). The organic layer was washed with water (5 L) and brine (5 L), and the solvents removed in vacuo to afford the desired product (1464 g, 77%) as a tan solid. LCMS for $C_{12}H_8BrFN_8O_3Na$ $(M+Na)^+$: m/z=433.0, 435.0. $^1H$ NMR (400 MHz, DMSO-$d_6$): δ 8.08 (dd, J=6.2, 2.5 Hz, 1H), 7.72 (m, 1H), 7.58 (t, J=8.7 Hz, 1H), 6.75 (t, J=5.7 Hz, 1H), 3.54 (t, J=5.3 Hz, 2H), 3.45 (dd, J=11.1, 5.2 Hz, 2H).

Step 11: 3-{4-[(2-Aminoethyl)amino]-1,2,5-oxadiazol-3-yl}-4-(3-bromo-4-fluorophenyl)-1,2,4-oxadiazol-5(4H)-one hydrochloride Sodium iodide (1080 g, 7.2 mol) was added to 3-{4-[(2-azidoethyl)amino]-1,2,5-oxadiazol-3-yl}-4-(3-bromo-4-fluorophenyl)-1,2,4-oxadiazol-5(4H)-one (500 g, 1.22 mol) in methanol (6 L). The mixture was allowed to stir for 30 min during which time a mild exotherm was observed. Chlorotrimethylsilane (930 mL, 7.33 mol) was added as a solution in methanol (1 L) dropwise at a rate so that the temperature did not exceed 35° C., and the reaction was allowed to stir for 3.5 h at ambient temperature. The reaction was neutralized with 33 wt % solution of sodium thiosulfate pentahydrate in water (~1.5 L), diluted with water (4 L), and the pH adjusted to 9 carefully with solid potassium carbonate (250 g—added in small portions: watch foaming). Di-tert-butyl dicarbonate (318 g, 1.45 mol) was added and the reaction was allowed to stir at room temperature. Additional potassium carbonate (200 g) was added in 50 g portions over 4 h to ensure that the pH was still at or above 9. After stirring at room temperature overnight, the solid was filtered, triturated with water (2 L), and then MTBE (1.5 L). A total of 11 runs were performed (5.5 kg, 13.38 mol). The combined solids were triturated with 1:1 THF:dichloromethane (24 L, 4 runs in a 20 L rotary evaporator flask, 50° C., 1 h), filtered, and washed with dichloromethane (3 L each run) to afford an off-white solid. The crude material was dissolved at 55° C. tetrahydrofuran (5 mL/g), treated with decolorizing carbon (2 wt %) and silica gel (2 wt %), and filtered hot through celite to afford the product as an off-white solid (5122 g). The combined MTBE, THF, and dichloromethane filtrates were concentrated in vacuo and chromatographed (2 kg silica gel, heptane with a 0-100% ethyl acetate gradient, 30 L) to afford more product (262 g). The combined solids were dried to a constant weight in a convection oven (5385 g, 83%).

In a 22 L flask was charged hydrogen chloride (4 N solution in 1,4-dioxane, 4 L, 16 mol). tert-Butyl [2-({4-[4-(3-bromo-4-fluorophenyl)-5-oxo-4,5-dihydro-1,2,4-oxadiazol-3-yl]-1,2,5-oxadiazol-3-yl}amino)ethyl]carbamate (2315 g, 4.77 mol) was added as a solid in portions over 10 min. The slurry was stirred at room temperature and gradually became a thick paste that could not be stirred. After sitting overnight at room temperature, the paste was slurried in ethyl acetate (10 L), filtered, re-slurried in ethyl acetate (5 L), filtered, and dried to a constant weight to afford the desired product as a white solid (combined with other runs, 5 kg starting material charged, 4113 g, 95%). LCMS for $C_{12}H_{11}BrFN_6O_3$ $(M+H)^+$: m/z=384.9, 386.9. $^1H$ NMR (400 MHz, DMSO-$d_6$): δ 8.12 (m, 4H), 7.76 (m, 1H), 7.58 (t, J=8.7 Hz, 1H), 6.78 (t, J=6.1 Hz, 1H), 3.51 (dd, J=11.8, 6.1 Hz, 2H), 3.02 (m, 2H).

Step 12: tert-Butyl ({[2-({4-[4-(3-bromo-4-fluorophenyl)-5-oxo-4,5-dihydro-1,2,4-oxadiazol-3-yl]-1,2,5-oxadiazol-3-yl}amino)ethyl]amino}sulfonyl)carbamate A 5 L round bottom flask was charged with chlorosulfonyl isocyanate [Aldrich, product #142662] (149 mL, 1.72 mol) and dichloromethane (1.5 L) and cooled using an ice bath to 2° C. tert-Butanol (162 mL, 1.73 mol) in dichloromethane (200 mL) was added dropwise at a rate so that the temperature did not exceed 10° C. The resulting solution was stirred at room temperature for 30-60 min to provide tert-butyl [chlorosulfonyl]carbamate.

A 22 L flask was charged with 3-{4-[(2-aminoethyl)amino]-1,2,5-oxadiazol-3-yl}-4-(3-bromo-4-fluorophenyl)-1,2,4-oxadiazol-5(4H)-one hydrochloride (661 g, 1.57 mol) and 8.5 L dichloromethane. After cooling to −15° C. with an ice/salt bath, the solution of tert-butyl [chlorosulfonyl]carbamate (prepared as above) was added at a rate so that the temperature did not exceed −10° C. (addition time 7 min). After stirring for 10 min, triethylamine (1085 mL, 7.78 mol) was added at a rate so that the temperature did not exceed −5° C. (addition time 10 min). The cold bath was removed, the reaction was allowed to warm to 10° C., split into two portions, and neutralized with 10% conc HCl (4.5 L each portion). Each portion was transferred to a 50 L separatory funnel and diluted with ethyl acetate to completely dissolve the white solid (~25 L). The layers were separated, and the organic layer was washed with water (5 L), brine (5 L), and the solvents removed in vacuo to afford an off-white solid. The solid was triturated with MTBE (2×1.5 L) and dried to a constant weight to afford a white solid. A total of 4113 g starting material was processed in this manner (5409 g, 98%). 1H NMR (400 MHz, DMSO-$d_6$): δ 10.90 (s, 1H), 8.08 (dd, J=6.2, 2.5 Hz, 1H), 7.72 (m, 1H), 7.59 (t, J=8.6 Hz, 1H), 6.58 (t, J=5.7 Hz, 1H), 3.38 (dd, J=12.7, 6.2 Hz, 2H), 3.10 (dd, J=12.1, 5.9 Hz, 2H), 1.41 (s, 9H).

Step 13: N-[2-({4-[4-(3-Bromo-4-fluorophenyl)-5-oxo-4,5-dihydro-1,2,4-oxadiazol-3-yl]-1,2,5-oxadiazol-3-yl}amino)ethyl]sulfamide To a 22 L flask containing 98:2 trifluoroacetic acid:water (8.9 L) was added tert-butyl ({[2-({4-[4-(3-bromo-4-fluorophenyl)-5-oxo-4,5-dihydro-1,2,4-oxadiazol-3-yl]-1,2,5-oxadiazol-3-yl}amino)ethyl]amino}sulfonyl)carbamate (1931 g, 3.42 mol) in portions over 10 minutes. The resulting mixture was stirred at room temperature for 1.5 h, the solvents removed in vacuo, and chased with dichloromethane (2 L). The resulting solid was treated a second time with fresh 98:2 trifluoroacetic acid:water (8.9 L), heated for 1 h at 40-50° C., the solvents removed in vacuo, and chased with dichloromethane (3×2 L). The resulting white solid was dried in a vacuum drying oven at 50° C. overnight. A total of 5409 g was processed in this manner (4990 g, quant. yield). LCMS for $C_{12}H_{12}BrFN_7O_5S$ $(M+H)^+$: m/z=463.9, 465.9. $^1$H NMR (400 MHz, DMSO-$d_6$): δ 8.08 (dd, J=6.2, 2.5 Hz, 1H), 7.72 (m, 1H), 7.59 (t, J=8.7 Hz, 1H), 6.67 (t, J=5.9 Hz, 1H), 6.52 (t, J=6.0 Hz, 1H), 3.38 (dd, J=12.7, 6.3 Hz, 2H), 3.11 (dd, J=12.3, 6.3 Hz).

Step 14: 4-({2-[(Aminosulfonyl)amino]ethyl}amino)-N-(3-bromo-4-fluorophenyl)-N'-hydroxy-1,2,5-oxadiazole-3-carboximidamide

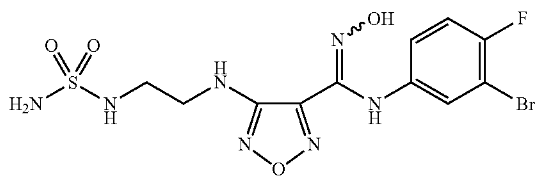 [SMILES: NS(=O)(=O)NCCNc1nonc1C(=NO)Nc1ccc(F)c(Br)c1]

To a crude mixture of N-[2-({4-[4-(3-bromo-4-fluorophenyl)-5-oxo-4,5-dihydro-1,2,4-oxadiazol-3-yl]-1,2,5-oxadiazol-3-yl}amino)ethyl]sulfamide (2.4 mol) containing residual amounts of trifluoroacetic acid stirring in a 22 L flask was added THE (5 L). The resulting solution was cooled to 0° C. using an ice bath and 2 N NaOH (4 L) was added at a rate so that the temperature did not exceed 10° C. After stirring at ambient temperature for 3 h (LCMS indicated no starting material remained), the pH was adjusted to 3-4 with concentrated HCl (~500 mL). The THF was removed in vacuo, and the resulting mixture was extracted with ethyl acetate (15 L). The organic layer was washed with water (5 L), brine (5 L), and the solvents removed in vacuo to afford a solid. The solid was triturated with MTBE (2×2 L), combined with three other reactions of the same size, and dried overnight in a convection oven to afford a white solid (3535 g). The solid was recrystallized (3×22 L flasks, 2:1 water:ethanol, 14.1 L each flask) and dried in a 50° C. convection oven to a constant weight to furnish the title compound as an off-white solid (3290 g, 78%). LCMS for $C_{11}H_{14}BrFN_7O_4S$ $(M+H)^+$: m/z=437.9, 439.9. $^1$H NMR (400 MHz, DMSO-$d_6$): δ 11.51 (s, 1H), 8.90 (s, 1H), 7.17 (t, J=8.8 Hz, 1H), 7.11 (dd, J=6.1, 2.7 Hz, 1H), 6.76 (m, 1H), 6.71 (t, J=6.0 Hz, 1H), 6.59 (s, 2H), 6.23 (t, J=6.1 Hz, 1H), 3.35 (dd, J=10.9, 7.0 Hz, 2H), 3.10 (dd, J=12.1, 6.2 Hz, 2H).

Example 2

N-(3-Bromo-4-fluorophenyl)-N'-hydroxy-4-({2-[(methylsulfonyl)amino]ethyl}amino)-1,2,5-oxadiazole-3-carboximidamide

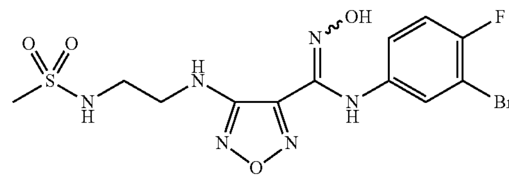 [SMILES: CS(=O)(=O)NCCNc1nonc1C(=NO)Nc1ccc(F)c(Br)c1]

The title compound was prepared according to the procedure of Example 21 step E, using N-hydroxy-4-({2-[(methylsulfonyl)amino]ethyl}amino)-1,2,5-oxadiazole-3-carboximidamide and 3-bromo-4-fluoroaniline [Oakwood Products, Inc., product #013091] as the starting materials. LCMS for $C_{12}H_{15}BrFN_6O_4S$ $(M+H)^+$: m/z=437.0, 439.0. $^1$H NMR (400 MHz, DMSO-$d_6$): δ 11.49 (s, 1H), 8.90 (s, 1H), 7.17 (m, 2H), 7.09 (dd, J=6.3, 2.5 Hz, 1H), 6.26 (t, J=6.1 Hz, 1H), 3.33 (m, 2H), 3.13 (q, J=6.0 Hz, 2H), 2.89 (s, 3H).

Example 3

4-({3-[(Aminosulfonyl)amino]propyl}amino)-N-(3-bromo-4-fluorophenyl)-N'-hydroxy-1,2,5-oxadiazole-3-carboximidamide

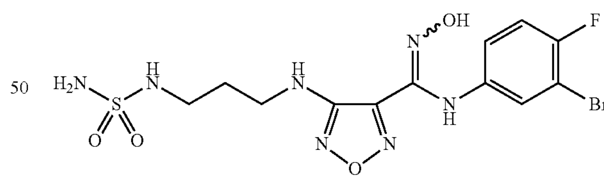

Step 1: 3-(4-Amino-1,2,5-oxadiazol-3-yl)-4-(3-bromo-4-fluorophenyl)-1,2,4-oxadiazol-5(4H)-one The desired compound was prepared according to the procedure of Example 9, step 1, using 4-amino-N-(3-bromo-4-fluorophenyl)-N'-hydroxy-1,2,5-oxadiazole-3-carboximidamide [see U. S. Pat. App. Pub. No. 2006/0258719] as the starting material in 98% yield. LCMS for $C_{10}H_6BrFN_5O_3$ $(M+H)^+$: m/z=342.0, 344.0. $^1$H NMR (400 MHz, DMSO-$d_6$): δ 8.06 (dd, J=6.2, 2.5 Hz, 1H), 7.72-7.67 (m, 1H), 7.58 (dd, J=8.7, 8.7 Hz, 1H), 6.60 (s, 2H).

Step 2: N-{4-[4-(3-Bromo-4-fluorophenyl)-5-oxo-4,5-dihydro-1,2,4-oxadiazol-3-yl]-1,2,5-oxadiazol-3-yl}-2,2,2-trifluoroacetamide The desired compound was prepared according to the procedure of Example 9, step 2, using 3-(4-amino-1,2,5-oxadiazol-3-yl)-4-(3-bromo-4-fluorophenyl)-1,2,4-oxadiazol-5(4H)-one as the starting material in 81% yield. LCMS for $C_{12}H_5BrF_4N_5O_4$ $(M+H)^+$: m/z=437.9, 439.9. $^1H$ NMR (400 MHz, DMSO-$d_6$): δ 7.92-7.89 (m, 1H), 7.54-7.52 (m, 2H).

Step 3: 4-(3-Bromo-4-fluorophenyl)-3-{4-[(3-methoxypropyl)amino]-1,2,5-oxadiazol-3-yl}-1,2,4-oxadiazol-5(4H)-one A solution of 3-methoxypropan-1-ol [Fluka product #38457] (3.1 mL, 32 mmol) and triphenylphosphine (8.4 g, 32 mmol) in tetrahydrofuran (93 mL) at 0° C. was treated with diisopropyl azodicarboxylate (6.7 mL, 34 mmol) dropwise. The reaction mixture was stirred at 0° C. for 15 min, treated with a solution of N-{4-[4-(3-bromo-4-fluorophenyl)-5-oxo-4,5-dihydro-1,2,4-oxadiazol-3-yl]-1,2,5-oxadiazol-3-yl}-2,2,2-trifluoroacetamide (10 g, 23 mmol) in tetrahydrofuran (47 mL), and stirred at 25° C. for 72 h. The reaction mixture was concentrated, diluted with ethyl acetate (200 mL), treated with trifluoroacetic acid (20 mL) and water (20 mL), and heated at 50° C. for 6 h. The reaction mixture was concentrated, rediluted with ethyl acetate (200 mL) and washed with water (3×80 mL), saturated sodium bicarbonate (2×80 mL) and brine (80 mL), dried over anhydrous sodium sulfate, filtered, and concentrated to a crude residue. This material was purified on silica gel to give the desired product (6.4 g, 54%) as a white solid. LCMS for $C_{14}H_{14}BrFN_5O_4(M+H)^+$: m/z=414.0, 416.0.

Step 4: 4-(3-Bromo-4-fluorophenyl)-3-{4-[(3-hydroxypropyl)amino]-1,2,5-oxadiazol-3-yl}-1,2,4-oxadiazol-5(4H)-one A solution of 4-(3-bromo-4-fluorophenyl)-3-{4-[(3-methoxypropyl)amino]-1,2,5-oxadiazol-3-yl}-1,2,4-oxadiazol-5(4H)-one (6.3 g, 14 mmol) in dichloromethane (60 mL) at −78° C. was treated with 1 M boron tribromide in dichloromethane (28 mL, 28 mmol) and stirred at 25° C. for 2 h. The reaction mixture was cooled to 0° C. and quenched with saturated sodium bicarbonate (100 mL). The aqueous layer was separated and extracted with dichloromethane (2×150 mL). The combined organic layers were washed with brine (100 mL), dried over anhydrous sodium sulfate, filtered, and concentrated to a crude off-white solid. This material was purified on silica gel to give the desired product (4.0 g, 73%) as a white solid. LCMS for $C_{13}H_{12}BrFN_5O_4$ $(M+H)^+$: m/z=400.0, 402.0. $^1H$ NMR (400 MHz, DMSO-$d_6$): δ 8.07 (dd, J=6.2, 2.5 Hz, 1H), 7.72-7.68 (m, 1H), 7.59 (dd, J=8.8, 8.6 Hz, 1H), 6.54 (t, J=5.7 Hz, 1H), 4.60 (t, J=5.1 Hz, 1H), 3.48-3.43 (m, 2H), 3.32-3.26 (m, 2H), 1.74-1.67 (m, 2H).

Step 5: 3-{4-[(3-Azidopropyl)amino]-1,2,5-oxadiazol-3-yl}-4-(3-bromo-4-fluorophenyl)-1,2,4-oxadiazol-5(4H)-one A solution of 4-(3-bromo-4-fluorophenyl)-3-{4-[(3-hydroxypropyl)amino]-1,2,5-oxadiazol-3-yl}-1,2,4-oxadiazol-5(4H)-one (3.0 g, 7.5 mmol) in dichloromethane (27 mL) was treated with methanesulfonyl chloride (0.75 mL, 9.7 mmol) and N,N-diisopropylethylamine (2.6 mL, 15 mmol) and stirred at 25° C. for 2 h. The reaction mixture was diluted with water (20 mL) and extracted with dichloromethane (20 mL). The organic layer was separated, dried over anhydrous sodium sulfate, filtered, and concentrated to give the mesylate which was used without further purification. A solution of the crude mesylate in N,N-dimethylformamide (24 mL) was treated with sodium azide (0.73 g, 11 mmol) and heated at 85° C. for 2 h. The reaction mixture was diluted with ethyl acetate (300 mL) and washed with water (100 mL), saturated sodium bicarbonate (100 mL), and brine (100 mL), dried over anhydrous sodium sulfate, filtered, and concentrated to give the desired product (3.2 g, 99%). This material was used without further purification. LCMS for $C_{13}H_{10}BrFN_8O_3Na$ $(M+Na)^+$: m/z=446.9, 448.9.

Step 6: 3-{4-[(3-Aminopropyl)amino]-1,2,5-oxadiazol-3-yl}-4-(3-bromo-4-fluorophenyl)-1,2,4-oxadiazol-5(4H)-one hydroiodide A solution of 3-{4-[(3-azidopropyl)amino]-1,2,5-oxadiazol-3-yl}-4-(3-bromo-4-fluorophenyl)-1,2,4-oxadiazol-5(4H)-one (2.0 g, 4.7 mmol) in methanol (36 mL) was treated with sodium iodide (4.2 g, 28 mmol) and stirred at 25° C. for 5 min. The reaction mixture was treated with a solution of chlorotrimethylsilane (3.6 mL, 28 mmol) in methanol (7 mL) dropwise and stirred at 25° C. for 40 min. The reaction mixture was slowly poured into a solution of sodium thiosulfate (5.0 g, 32 mmol) in water (200 mL) that was cooled at 0° C. The solid that precipitated was filtered, washed with water, and dried to give the desired product (2.3 g, 93%) as a solid. LCMS for $C_{13}H_{13}BrFN_6O_3(M+H)^+$: m/z=399.0, 401.0. $^1H$ NMR (400 MHz, DMSO-$d_6$): δ 8.08 (dd, J=6.1, 2.3 Hz, 1H), 7.74-7.70 (m, 1H), 7.60 (dd, J=8.8, 8.6 Hz, 1H), 7.22 (br s, 2H), 6.69 (br s, 1H), 2.81-2.77 (m, 2H), 1.86-1.79 (m, 2H).

Step 7: N-[3-({4-[4-(3-Bromo-4-fluorophenyl)-5-oxo-4,5-dihydro-1,2,4-oxadiazol-3-yl]-1,2,5-oxadiazol-3-yl}amino)propyl]sulfamide A solution of 3-{4-[(3-aminopropyl)amino]-1,2,5-oxadiazol-3-yl}-4-(3-bromo-4-fluorophenyl)-1,2,4-oxadiazol-5(4H)-one hydroiodide (150 mg, 0.28 mmol) and sulfamide (160 mg, 1.7 mmol) in pyridine (2.5 mL) was heated in a microwave at 130° C. for 10 min. The reaction mixture was concentrated to give a crude residue. This material was purified by preparative LCMS to give the desired product (96 mg, 71%) as a solid. LCMS for $C_{13}H_{14}BrFN_7O_5S$ $(M+H)^+$: m/z=478.0, 480.0. $^1H$ NMR (400 MHz, DMSO-$d_6$): δ 8.07 (dd, J=6.2, 2.5 Hz, 1H), 7.73-7.69 (m, 1H), 7.59 (dd, J=8.8, 8.6 Hz, 1H), 6.57-6.51 (m, 4H), 3.31-3.26 (m, 2H), 2.92-2.87 (m, 2H), 1.79-1.72 (m, 2H).

Step 8: 4-({3-[(Aminosulfonyl)amino]propyl}amino)-N-(3-bromo-4-fluorophenyl)-N'-hydroxy-1,2,5-oxadiazole-3-carboximidamide

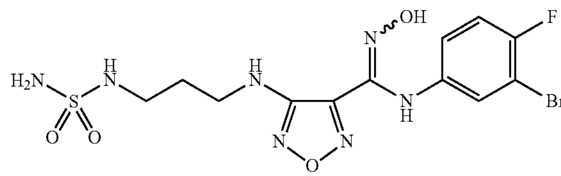 [SMILES: NS(=O)(=O)NCCCNc1nonc1C(=NO)Nc1ccc(F)c(Br)c1]

A solution of N-[3-({4-[4-(3-bromo-4-fluorophenyl)-5-oxo-4,5-dihydro-1,2,4-oxadiazol-3-yl]-1,2,5-oxadiazol-3-yl}amino)propyl]sulfamide (35 mg, 73 μmol) in methanol (1 mL) was treated with 2 M NaOH (0.3 mL, 0.6 mmol) and stirred at 25° C. for 30 min. The reaction mixture was treated with acetic acid (50 μL, 0.9 mmol), filtered, and purified by preparative LCMS to give the desired product (14 mg, 42%) as a solid. LCMS for $C_{12}H_{16}BrFN_7O_4S$ $(M+H)^+$: m/z=451.8, 453.9. $^1H$ NMR (400 MHz, DMSO-$d_6$): δ 11.5 (s, 1H), 8.89 (s, 1H), 7.17 (dd, J=8.8, 8.6 Hz, 1H), 7.09 (dd, J=6.1, 2.7 Hz, 1H), 6.76-6.72 (m, 1H), 6.56 (dd, J=6.1, 6.1 Hz, 1H), 6.51 (s, 2H), 6.17 (dd, J=5.9, 5.9 Hz, 1H), 3.27-3.21 (m, 2H), 2.94-2.88 (m, 2H), 1.78-1.71 (m, 2H).

Example 4

N-(3-Bromo-4-fluorophenyl)-N'-hydroxy-4-({3-[(methylsulfonyl)amino]propyl}amino)-1,2,5-oxadiazole-3-carboximidamide

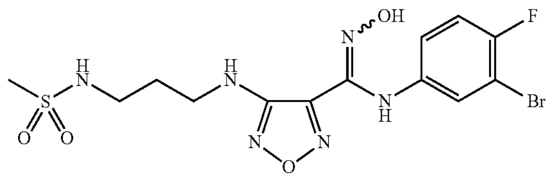 [SMILES: CS(=O)(=O)NCCCNc1nonc1C(=NO)Nc1ccc(F)c(Br)c1]

Step 1: tert-Butyl {3-[(methylsulfonyl)amino]propyl}carbamate

The desired compound was prepared according to the procedure of Example 21, step 1, using N-(3-aminopropyl)(tert-butoxy)carboxamide [Aldrich product #436992] as the starting material in 70% yield. LCMS for $C_4H_{13}N_2O_2S$ $([M-Boc+H]+H)^+$: m/z=153.1.

Step 2: N-(3-Aminopropyl)methanesulfonamide hydrochloride

The desired compound was prepared according to the procedure of Example 21, step 2, using tert-butyl {3-[(methylsulfonyl)amino]propyl}carbamate as the starting material. LCMS for $C_4H_{13}N_2O_2S$ $(M+H)^+$: m/z=153.1.

Step 3: 4-Amino-N'-hydroxy-N-{3-[(methylsulfonyl)amino]propyl}-1,2,5-oxadiazole-3-carboximidamide The desired compound was prepared according to the procedure of Example 21, step 3, using N-(3-aminopropyl)methanesulfonamide hydrochloride and 4-amino-N-hydroxy-1,2,5-oxadiazole-3-carboximidoyl chloride [made according to Example 9, steps 1 through 2] as the starting materials in 19% yield.

Step 4: N'-Hydroxy-4-({3-[(methylsulfonyl)amino]propyl}amino)-1,2,5-oxadiazole-3-carboximidamide The desired compound was prepared according to the procedure of Example 21, step 4, using 4-amino-N'-hydroxy-N-{3-[(methylsulfonyl)amino]propyl}-1,2,5-oxadiazole-3-carboximidamide as the starting material. LCMS for $C_7H_{15}N_6O_4S$ $(M+H)^+$: m/z=279.0.

Step 5: N-(3-Bromo-4-fluorophenyl)-N'-hydroxy-4-({3-[(methylsulfonyl)amino]propyl}amino)-1,2,5-oxadiazole-3-carboximidamide

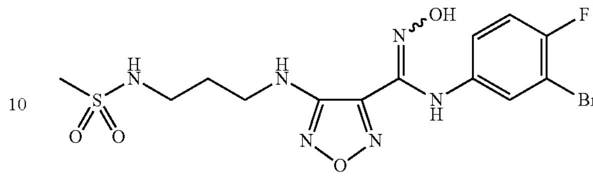

The title compound was prepared according to the procedure of Example 21, step 5, using N'-hydroxy-4-({3-[(methylsulfonyl)amino]propyl}amino)-1,2,5-oxadiazole-3-carboximidamide and 3-bromo-4-fluoroaniline [Oakwood Products, Inc., product #013091] as the starting materials in 12% yield. LCMS for $C_{13}H_{17}BrFN_6O_4S$ $(M+H)^+$: m/z=451.0, 453.0. $^1H$ NMR (400 MHz, $CD_3OD$): δ 7.12 (dd, J=5.9, 2.4 Hz, 1H), 7.05 (t, J=8.7 Hz, 1H), 6.83 (m, 1H), 3.39 (t, J=6.8 Hz, 2H), 3.14 (t, J=6.6 Hz, 2H), 2.94 (s, 3H), 1.87 (m, 2H).

Example 5

4-({2-[(Aminosulfonyl)amino]ethyl}amino)-N-(3-chloro-4-fluorophenyl)-N'-hydroxy-1,2,5-oxadiazole-3-carboximidamide

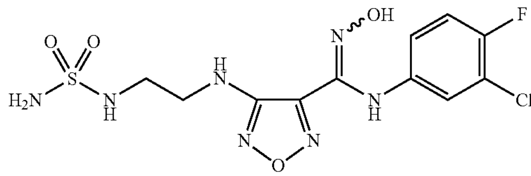 [SMILES: NS(=O)(=O)NCCNc1nonc1C(=NO)Nc1ccc(F)c(Cl)c1]

Step 1: 3-(4-Amino-1,2,5-oxadiazol-3-yl)-4-(3-chloro-4-fluorophenyl)-1,2,4-oxadiazol-5(4H)-one A solution of 4-amino-N-(3-chloro-4-fluorophenyl)-N'-hydroxy-1,2,5-oxadiazole-3-carboximidamide (80 g, 0.29 mol) [see US Pat. App. Pub. No. 2006/0258719] in tetrahydrofuran (500 mL) was treated with a solution of 1,1'-carbonyldiimidazole (53 g, 0.32 mol) in tetrahydrofuran (200 mL) and heated at reflux for 1 h. The reaction mixture was cooled to 25° C. and concentrated to the point where a large amount of solid precipitated. The heterogeneous mixture was diluted with ethyl acetate (1.5 L) and washed with 1 N HCl (2×300 mL), water (300 mL), and brine (200 mL). The organic layer was separated, dried over anhydrous sodium sulfate, filtered, and concentrated to give the desired product (88 g, quantitative) as an off-white solid. This material was used without further purification. LCMS for $C_{10}H_6ClFN_5O_3$ $(M+H)^+$: m/z=298.0. $^1H$ NMR (400 MHz, DMSO-$d_6$): δ 7.96 (dd, J=6.6, 2.3 Hz, 1H), 7.69-7.60 (m, 2H), 6.60 (s, 2H).

Step 2: N-{4-[4-(3-Chloro-4-fluorophenyl)-5-oxo-4,5-dihydro-1,2,4-oxadiazol-3-yl]-1,2,5-oxadiazol-3-yl}-2,2,2-trifluoroacetamide A solution of 3-(4-amino-1,2,5-oxadiazol-3-yl)-4-(3-chloro-4-fluorophenyl)-1,2,4-oxadiazol-5(4H)-one (15 g, 50 mmol) in dichloromethane (120 mL) was treated with trifluoroacetic anhydride (14 mL, 100 mmol), cooled to 0° C., and treated with pyridine (8.2 mL, 100 mmol). The reaction mixture was stirred at 25° C. for 10 min, cooled to 0° C., and quenched with water (10 mL). The reaction mixture was diluted with ethyl acetate (500 mL) and washed with 1 N HCl (300 mL), water (2×200 mL), and brine (200 mL). The organic layer was separated, dried over anhydrous sodium sulfate, filtered, and concentrated to −50 mL volume. This solution was warmed (~40-50° C.) and treated with hexanes (600 mL) under vigorous stirring, followed by petroleum ether (200 mL). The mixture was stirred at 0° C. for 30 min and the solid was collected by filtration, washed with hexanes, and dried to give the desired product (19.7 g, 99%) as a white solid. LCMS for $C_{12}H_5ClF_4N_5O_4$ $(M+H)^+$: m/z=394.0. $^1$H NMR (400 MHz, DMSO-$d_6$): δ 7.82 (dd, J=6.6, 2.5 Hz, 1H), 7.59 (dd, J=9.0, 9.0 Hz, 1H), 7.52-7.47 (m, 1H).

Step 3: 4-(3-Chloro-4-fluorophenyl)-3-(4-{[2-(tritylamino)ethyl]amino}-1,2,5-oxadiazol-3-yl)-1,2,4-oxadiazol-5(4H)-one A solution of 2-(tritylamino)ethanol (10 g, 33 mmol) [EP599220 and *J. Org. Chem.* (2001), 66, 7615] and triphenylphosphine (8.7 g, 33 mmol) in tetrahydrofuran (65 mL) at 0° C. was treated with diisopropyl azodicarboxylate (7.0 mL, 35 mmol) dropwise. The reaction mixture was stirred at 0° C. for 15 min, treated with a solution of N-{4-[4-(3-chloro-4-fluorophenyl)-5-oxo-4,5-dihydro-1,2,4-oxadiazol-3-yl]-1,2,5-oxadiazol-3-yl}-2,2,2-trifluoroacetamide (9.3 g, 24 mmol) in tetrahydrofuran (28 mL), and stirred at 25° C. for 16 h. The reaction mixture was concentrated, diluted with ethyl acetate (350 mL), cooled to 0° C., treated with 1 N HCl (200 mL), and stirred at 25° C. for 1 h. The reaction mixture was treated with additional 1 N HCl (150 mL) and stirred at 25° C. for 3 h. The organic layer was separated, washed with saturated sodium bicarbonate (200 mL) and brine (100 mL), dried over anhydrous sodium sulfate, filtered, and concentrated to a yellow foam which was reconcentrated from hexanes to give an oily solid. The oily solid was treated with methyl tert-butyl ether (50 mL) and stirred to give a heterogeneous mixture. The solid was filtered, washed with methyl tert-butyl ether (30 mL), and dried to give the desired product (10 g, 74%) as a white solid. LCMS for $C_{31}H_{24}ClFN_6O_3Na$ $(M+Na)^+$: m/z=605.2. $^1$H NMR (300 MHz, DMSO-$d_6$): δ 7.97 (dd, J=6.7, 2.6 Hz, 1H), 7.71-7.66 (m, 1H), 7.60 (dd, J=9.1, 8.8 Hz, 1H), 7.40-7.37 (m, 6H), 7.28-7.23 (m, 6H), 7.18-7.12 (m, 3H), 6.59 (dd, J=5.9, 5.6 Hz, 1H), 3.37-3.31 (m, 2H), 2.96 (dd, J=7.6, 7.6 Hz, 1H), 2.27-2.19 (m, 2H).

Step 4: 3-{4-[(2-Aminoethyl)amino]-1,2,5-oxadiazol-3-yl}-4-(3-chloro-4-fluorophenyl)-1,2,4-oxadiazol-5(4H)-one hydrochloride A premixed solution of triisopropylsilane (3.4 mL, 17 mmol) and trifluoroacetic acid (44 mL, 570 mmol) was added to 4-(3-chloro-4-fluorophenyl)-3-(4-{[2-(tritylamino)ethyl]amino}-1,2,5-oxadiazol-3-yl)-1,2,4-oxadiazol-5(4H)-one (6.5 g, 11 mmol) and the resulting suspension was stirred at 25° C. for 30 min. The reaction mixture was filtered and washed with trifluoroacetic acid. The filtrate was concentrated to an oil which was diluted with methanol (25 mL), cooled to 0° C., treated with 4 M HCl in 1,4-dioxane (14 mL), and stirred at 25° C. for 15 min. The mixture was concentrated to a solid that was treated with diethyl ether (50 mL) and filtered. The solid was washed with diethyl ether (50 mL) and dried to give the desired product (4.1 g, 98%) as a white solid. LCMS for $C_{12}H_{11}ClFN_6O_3(M+H)^+$: m/z=341.1. $^1$H NMR (300 MHz, DMSO-$d_6$): δ 8.05-8.00 (m, 4H), 7.75-7.69 (m, 1H), 7.64 (dd, J=9.1, 8.8 Hz, 1H), 6.77 (dd, J=5.9, 5.9 Hz, 1H), 3.54-3.47 (m, 2H), 3.04-2.99 (m, 2H).

Step 5: N-[2-({4-[4-(3-Chloro-4-fluorophenyl)-5-oxo-4,5-dihydro-1,2,4-oxadiazol-3-yl]-1,2,5-oxadiazol-3-yl}amino)ethyl]sulfamide A solution of chlorosulfonyl isocyanate (2.0 mL, 23 mmol) in dichloromethane (70 mL) was treated with t-butyl alcohol (2.2 mL, 23 mmol) at 0° C. and stirred at 25° C. for 1 h. This mixture was added to a suspension of 3-{4-[(2-aminoethyl)amino]-1,2,5-oxadiazol-3-yl}-4-(3-chloro-4-fluorophenyl)-1,2,4-oxadiazol-5(4H)-one hydrochloride (4.3 g, 11 mmol) in dichloromethane (70 mL). The reaction mixture was treated with a solution of triethylamine (6.3 mL, 45 mmol) in dichloromethane (20 mL) at 0° C. and stirred at 25° C. for 3 h. The reaction mixture was diluted with 0.1 N HCl and extracted with ethyl acetate (2×100 mL). The combined organic layers were washed with brine (100 mL), dried over anhydrous sodium sulfate, filtered, and concentrated to a white solid. The white solid was diluted with dichloromethane (100 mL), treated with trifluoroacetic acid (20 mL), and stirred at 25° C. for 3 h. The reaction mixture was concentrated to a crude residue that was purified by silica gel chromatography to give the desired product (3.7 g, 78%) as a white solid. LCMS for $C_{12}H_{12}ClFN_7O_5S$ $(M+H)^+$: m/z=420.0. $^1$H NMR (300 MHz, DMSO-$d_6$): δ 7.98 (dd, J=6.4, 2.1 Hz, 1H), 7.70-7.60 (m, 2H), 6.66 (t, J=5.9 Hz, 1H), 6.57 (s, 2H), 6.52 (t, J=5.9 Hz, 1H), 3.42-3.35 (m, 2H), 3.13-3.06 (m, 2H).

Step 6: 4-({2-[(Aminosulfonyl)amino]ethyl}amino)-N-(3-chloro-4-fluorophenyl)-N'-hydroxy-1,2,5-oxadiazole-3-carboximidamide

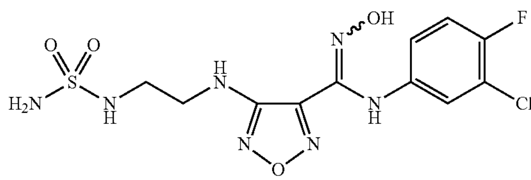 [SMILES: NS(=O)(=O)NCCNc1nonc1C(=NO)Nc1ccc(F)c(Cl)c1]

A solution of N-[2-({4-[4-(3-chloro-4-fluorophenyl)-5-oxo-4,5-dihydro-1,2,4-oxadiazol-3-yl]-1,2,5-oxadiazol-3-yl}amino)ethyl]sulfamide (3.7 g, 8.8 mmol) in methanol (70 mL) was treated with 2 M NaOH (18 mL, 35 mmol) and stirred at 25° C. for 2 h. The reaction mixture was quenched with 6 N HCl to pH-7 and the methanol was removed under reduced pressure. The solid that precipitated was filtered and washed with water to give the desired product (3.2 g, 92%) as a white solid. LCMS for $C_{11}H_{14}ClFN_7O_4S$ $(M+H)^+$: m/z=394.0. $^1$H NMR (400 MHz, DMSO-$d_6$): δ 7.96 (dd, J=6.8, 2.1 Hz, 0.05H), 7.32-7.29 (m, 0.1H), 7.18 (dd, J=9.1, 9.1 Hz, 0.95H), 6.93 (dd, J=6.4, 2.7 Hz, 0.95H), 6.71-6.66 (m, 0.95H), 6.33 (br s, 1H), 3.35-3.27 (m, 2H), 3.10-3.06 (m, 2H).

Example 6

N-(3-Chloro-4-fluorophenyl)-N'-hydroxy-4-({2-[(methylsulfonyl)amino]ethyl}amino)-1,2,5-oxadiazole-3-carboximidamide

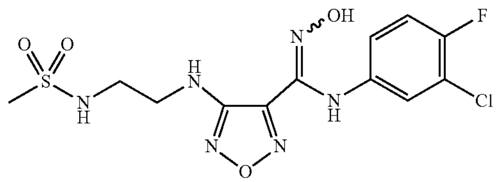 [SMILES: CS(=O)(=O)NCCNc1nonc1C(=NO)Nc1ccc(F)c(Cl)c1]

The title compound was prepared according to the procedure of Example 21 step E, using N-hydroxy-4-({2-[(methylsulfonyl)amino]ethyl}amino)-1,2,5-oxadiazole-3-carboximidamide and 3-chloro-4-fluoroaniline [Aldrich, product #228583] as the starting materials. LCMS for $C_{12}H_{15}ClFN_6O_4S$ $(M+H)^+$: m/z=393.0. $^1H$ NMR (400 MHz, DMSO-$d_6$): δ 11.50 (s, 1H), 8.91 (s, 1H), 7.19 (m, 2H), 6.96 (dd, J=6.7, 2.5 Hz, 1H), 6.71 (m, 1H), 6.26 (t, J=6.4 Hz, 1H), 3.32 (m, 2H), 3.13 (q, J=5.8 Hz, 2H), 2.89 (s, 3H).

Example 7

4-({3-[(Aminosulfonyl)amino]propyl}amino)-N-(3-chloro-4-fluorophenyl)-N'-hydroxy-1,2,5-oxadiazole-3-carboximidamide

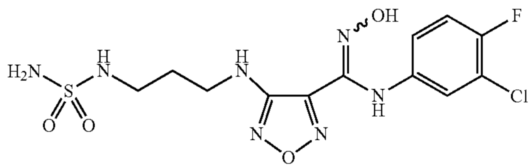 [SMILES: NS(=O)(=O)NCCCNc1nonc1C(=NO)Nc1ccc(F)c(Cl)c1]

Step 1: 3-[(Diphenylmethylene)amino]propan-1-ol

A solution of 3-amino-1-propanol [Aldrich product #A76400] (2.0 mL, 26 mmol) in dichloromethane (79 mL) was treated with benzophenone imine (4.4 mL, 26 mmol) and stirred at 25° C. for 16 h. The reaction mixture was filtered and the filtrate was concentrated to give the desired product (6.3 g, quantitative) as an oil. This material was used without further purification. LCMS for $C_{16}H_{18}NO$ $(M+H)^+$: m/z=240.2.

Step 2: 3-{4-[(3-Aminopropyl)amino]-1,2,5-oxadiazol-3-yl}-4-(3-chloro-4-fluorophenyl)-1,2,4-oxadiazol-5(4H)-one trifluoroacetate A solution of 3-[(diphenylmethylene)amino]propan-1-ol (80 mg, 0.33 mmol) and triphenylphosphine (93 mg, 0.36 mmol) in tetrahydrofuran (1 mL) at 0° C. was treated with diisopropyl azodicarboxylate (75 μL, 0.38 mmol) dropwise. The reaction mixture was stirred at 0° C. for 15 min, treated with a solution of N-{4-[4-(3-chloro-4-fluorophenyl)-5-oxo-4,5-dihydro-1,2,4-oxadiazol-3-yl]-1,2,5-oxadiazol-3-yl}-2,2,2-trifluoroacetamide (100 mg, 0.25 mmol) in tetrahydrofuran (0.5 mL), and stirred at 25° C. for 16 h. The reaction mixture was treated with trifluoroacetic acid (1 mL), stirred at 25° C. for 3 h, and concentrated to a crude residue. This material was purified by preparative LCMS to give the desired product (18 mg, 15%). LCMS for $C_{13}H_{13}ClFN_6O_3$ $(M+H)^+$: m/z=355.1

Step 3: 4-({3-[(Aminosulfonyl)amino]propyl}amino)-N-(3-chloro-4-fluorophenyl)-N'-hydroxy-1,2,5-oxadiazole-3-carboximidamide

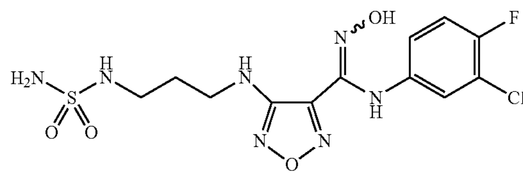 [SMILES: NS(=O)(=O)NCCCNc1nonc1C(=NO)Nc1ccc(F)c(Cl)c1]

The desired compound was prepared according to the procedure of Example 19, step 7, using 3-{4-[(3-aminopropyl)amino]-1,2,5-oxadiazol-3-yl}-4-(3-chloro-4-fluorophenyl)-1,2,4-oxadiazol-5(4H)-one trifluoroacetate as the starting material in 34% yield. LCMS for $C_{12}H_{16}ClFN_7O_4S$ $(M+H)^+$: m/z=408.1. $^1H$ NMR (400 MHz, DMSO-$d_6$): δ 8.90 (s, 1H), 7.20 (dd, J=9.2, 9.0 Hz, 1H), 6.96 (dd, J=6.4, 2.7 Hz, 1H), 6.72-6.69 (m, 1H), 6.55 (t, J=6.0 Hz, 1H), 6.51 (s, 2H), 6.16 (t, J=5.9 Hz, 1H), 3.28-3.21 (m, 2H), 2.93-2.87 (m, 2H), 1.76-1.72 (m, 2H).

Example 8

N-(3-Chloro-4-fluorophenyl)-N'-hydroxy-4-({3-[(methylsulfonyl)amino]propyl}amino)-1,2,5-oxadiazole-3-carboximidamide

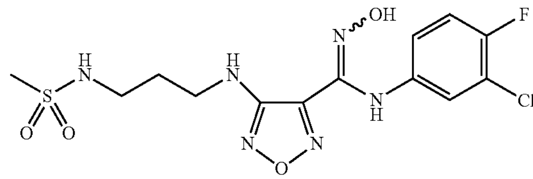 [SMILES: CS(=O)(=O)NCCCNc1nonc1C(=NO)Nc1ccc(F)c(Cl)c1]

The title compound was prepared according to the procedure of Example 8, step 5, using N'-hydroxy-4-({3-[(methylsulfonyl)amino]propyl}amino)-1,2,5-oxadiazole-3-carboximidamide [made according to Example 8, steps 1 through 4] and 3-chloro-4-fluoroaniline [Aldrich, product #228583] as the starting materials in 10% yield. LCMS for $C_{13}H_{17}ClFN_6O_4S$ $(M+H)^+$: m/z=407.1. $^1H$ NMR (400 MHz, $CD_3OD$): δ 7.06 (t, J=8.9 Hz, 1H), 6.98 (m, 1H), 6.80 (m, 1H), 3.73 (m, 2H), 3.28 (m, 2H), 2.94 (s, 3H), 1.28 (m, 2H).

Example 9

4-({2-[(Aminosulfonyl)amino]ethyl}amino)-N-[4-fluoro-3-(trifluoromethyl)phenyl]-N'-hydroxy-1,2,5-oxadiazole-3-carboximidamide

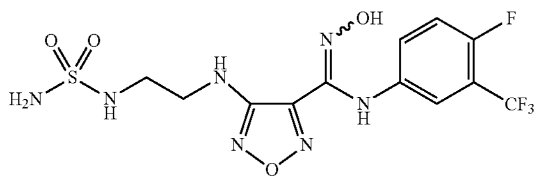 [SMILES: NS(=O)(=O)NCCNc1nonc1C(=NO)Nc1ccc(F)c(C(F)(F)F)c1]

Step 1: N-[4-Fluoro-3-(trifluoromethyl)phenyl]-N'-hydroxy-4-[(2-methoxyethyl)amino]-1,2,5-oxadiazole-3-carboximidamide The desired compound was prepared according to the procedure of Example 17, step 1, using N-hydroxy-4-[(2-methoxyethyl)amino]-1,2,5-oxadiazole-3-carboximidoyl chloride [made according to Example 5, steps 1 through 5] and 3-trifluoromethyl-4-fluoroaniline [Aldrich, product #217778] as the starting materials in quantitative yield. LCMS for $C_{13}H_{14}F_4N_5O_3$ $(M+H)^+$: m/z=364.0. $^1$H NMR (400 MHz, $CD_3OD$): δ 7.15 (m, 2H), 7.08 (m, 1H), 3.60 (t, J=5.3 Hz, 2H), 3.46 (t, J=5.3 Hz, 2H), 3.38 (s, 3H).

Step 2: 4-[4-Fluoro-3-(trifluoromethyl)phenyl]-3-{4-[(2-methoxyethyl)amino]-1,2,5-oxadiazol-3-yl}-1,2,4-oxadiazol-5(4H)-one The desired compound was prepared according to the procedure of Example 17, step 2, using N-[4-fluoro-3-(trifluoromethyl)phenyl]-N'-hydroxy-4-[(2-methoxyethyl)amino]-1,2,5-oxadiazole-3-carboximidamide as the starting material in 79% yield. LCMS for $C_{14}H_{12}F_4N_5O_4$ $(M+H)^+$: m/z=390.0. $^1$H NMR (400 MHz, DMSO-$d_6$): δ 8.20 (dd, J=6.3, 2.4 Hz, 1H), 8.03 (m, 1H), 7.76 (t, J=9.5 Hz, 1H), 6.41 (t, J=5.7 Hz, 1H), 3.49 (t, J=5.5 Hz, 2H), 3.39 (q, J=5.7 Hz, 2H), 3.25 (s, 3H).

Step 3: 4-[4-Fluoro-3-(trifluoromethyl)phenyl]-3-{4-[(2-hydroxyethyl)amino]-1,2,5-oxadiazol-3-yl}-1,2,4-oxadiazol-5(4H)-one The desired compound was prepared according to the procedure of Example 17, step 3, using 4-[4-fluoro-3-(trifluoromethyl)phenyl]-3-{4-[(2-methoxyethyl)amino]-1,2,5-oxadiazol-3-yl}-1,2,4-oxadiazol-5(4H)-one as the starting material in 99% yield. LCMS for $C_{13}H_{10}F_4N_5O_4$ $(M+H)^+$: m/z=376.0. $^1$H NMR (400 MHz, DMSO-$d_6$): δ 8.22 (m, 1H), 8.05 (m, 1H), 7.76 (t, J=9.9 Hz, 1H), 6.34 (t, J=5.7 Hz, 1H), 4.87 (t, J=5.2 Hz, 1H), 3.56 (q, J=5.5 Hz, 2H), 3.29 (q, J=5.7 Hz, 2H).

Step 4: 2-[(4-{4-[4-Fluoro-3-(trifluoromethyl)phenyl]-5-oxo-4,5-dihydro-1,2,4-oxadiazol-3-yl}-1,2,5-oxadiazol-3-yl)amino]ethyl methanesulfonate The desired compound was prepared according to the procedure of Example 17, step 4, using 4-[4-fluoro-3-(trifluoromethyl)phenyl]-3-{4-[(2-hydroxyethyl)amino]-1,2,5-oxadiazol-3-yl}-1,2,4-oxadiazol-5(4H)-one as the starting material in 95% yield. LCMS for $C_{14}H_{12}F_4N_5O_6S$ $(M+H)^+$: m/z=454.0. $^1$H NMR (400 MHz, DMSO-$d_6$): δ 8.23 (dd, J=6.5, 2.5 Hz, 1H), 8.06 (m, 1H), 7.76 (t, J=9.6 Hz, 1H), 6.76 (t, J=5.8 Hz, 1H), 4.37 (t, J=5.4 Hz, 2H), 3.60 (q, J=5.5 Hz, 2H), 3.17 (s, 3H).

Step 5: 3-{4-[(2-Azidoethyl)amino]-1,2,5-oxadiazol-3-yl}-4-[4-fluoro-3-(trifluoromethyl)phenyl]-1,2,4-oxadiazol-5(4H)-one The desired compound was prepared according to the procedure of Example 17, step 5, using 2-[(4-{4-[4-fluoro-3-(trifluoromethyl)phenyl]-5-oxo-4,5-dihydro-1,2,4-oxadiazol-3-yl}-1,2,5-oxadiazol-3-yl)amino]ethyl methanesulfonate as the starting material in 100% yield. LCMS for $C_{13}H_9F_4N_6O_3$ $(M-N_2+H)^+$: m/z=372.8. $^1$H NMR (400 MHz, DMSO-$d_6$): δ 8.22 (dd, J=6.2, 2.4 Hz, 1H), 8.05 (m, 1H), 7.76 (t, J=9.6 Hz, 1H), 6.75 (t, J=5.9 Hz, 1H), 3.53 (t, J=5.9 Hz, 2H), 3.45 (q, J=5.6 Hz, 2H).

Step 6: 3-{4-[(2-Aminoethyl)amino]-1,2,5-oxadiazol-3-yl}-4-[4-fluoro-3-(trifluoromethyl)phenyl]-1,2,4-oxadiazol-5(4H)-one hydroiodide The desired compound was prepared according to the procedure of Example 17, step 6, using 3-{4-[(2-azidoethyl)amino]-1,2,5-oxadiazol-3-yl}-4-[4-fluoro-3-(trifluoromethyl)phenyl]-1,2,4-oxadiazol-5(4H)-one as the starting material in 80% yield. LCMS for $C_{13}H_{11}F_4N_6O_3$ $(M+H)^+$: m/z=375.0. $^1$H NMR (400 MHz, DMSO-$d_6$): δ 8.20 (dd, J=6.2, 2.4 Hz, 1H), 8.03 (m, 1H), 7.74 (t, J=9.8 Hz, 1H), 7.10 (br s, 0.4H), 6.68 (t, J=5.5 Hz, 1H), 3.42 (q, J=5.8 Hz, 2H), 2.95 (t, J=6.5 Hz, 2H).

Step 7: 4-({2-[(Aminosulfonyl)amino]ethyl}amino)-N-[4-fluoro-3-(trifluoromethyl)phenyl]-N'-hydroxy-1,2,5-oxadiazole-3-carboximidamide

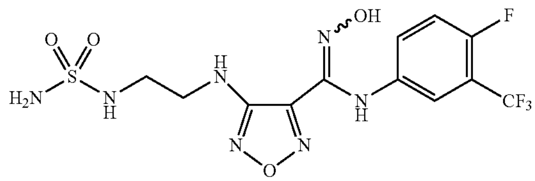 [SMILES: NS(=O)(=O)NCCNc1nonc1C(=NO)Nc1ccc(F)c(C(F)(F)F)c1]

The title compound was prepared according to the procedure of Example 17, step 7, using 3-{4-[(2-aminoethyl)amino]-1,2,5-oxadiazol-3-yl}-4-[4-fluoro-3-(trifluoromethyl)phenyl]-1,2,4-oxadiazol-5(4H)-one hydroiodide as the starting material in 55% yield. LCMS for $C_{12}H_{14}F_4N_7O_4S$ $(M+H)^+$: m/z=428.0. $^1$H NMR (400 MHz, DMSO-$d_6$): δ 11.60 (s, 1H), 9.06 (s, 1H), 7.30 (t, J=10.1 Hz, 1H), 7.14 (dd, J=6.1, 2.7 Hz, 1H), 7.03 (m, 1H), 6.71 (t, J=5.3 Hz, 1H), 6.58 (s, 2H), 6.23 (t, J=6.2 Hz, 1H), 3.36 (q, J=6.5 Hz, 2H), 3.08 (m, 2H).

Example 10

N-[4-Fluoro-3-(trifluoromethyl)phenyl]-N'-hydroxy-4-({2-[(methylsulfonyl)amino]ethyl}amino)-1,2,5-oxadiazole-3-carboximidamide

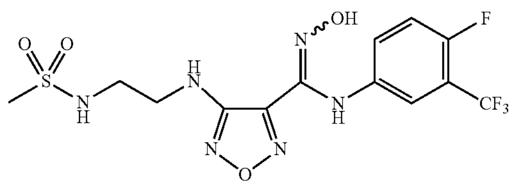 [SMILES: CS(=O)(=O)NCCNc1nonc1C(=NO)Nc1ccc(F)c(C(F)(F)F)c1]

The title compound was prepared according to the procedure of Example 21 step E, using N-hydroxy-4-({2-[(methylsulfonyl)amino]ethyl}amino)-1,2,5-oxadiazole-3-carboximidamide and 3-trifluoromethyl-4-fluoroaniline [Aldrich, product #217778] as the starting materials. LCMS for $C_{13}H_{15}F_4N_6O_4S$ $(M+H)^+$: m/z=427.0. $^1$H NMR (400 MHz, DMSO-$d_6$): δ 11.60 (s, 1H), 9.07 (s, 1H), 7.30 (t, J=10.1 Hz, 1H), 7.18 (t, J=6.0 Hz, 1H), 7.13 (dd, J=6.0, 2.7 Hz, 1H), 7.03 (m, 1H), 6.27 (t, J=6.3 Hz, 1H), 3.32 (m, 2H), 3.13 (q, J=6.0 Hz, 2H), 2.89 (s, 3H).

Example 11

4-({3-[(Aminosulfonyl)amino]propyl}amino)-N-[4-fluoro-3-(trifluoromethyl)phenyl]-N'-hydroxy-1,2,5-oxadiazole-3-carboximidamide

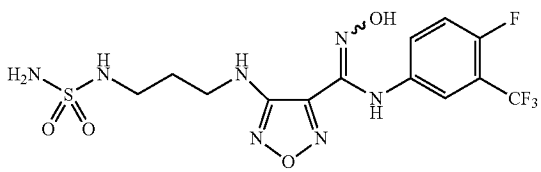 [SMILES: NS(=O)(=O)NCCCNc1nonc1C(=NO)Nc1ccc(F)c(C(F)(F)F)c1]

Step 1: 4-Amino-N'-hydroxy-N-(3-methoxypropyl)-1,2,5-oxadiazole-3-carboximidamide The desired compound was prepared according to the procedure of Example 5, step 3, using 3-methoxy-1-propanamine as the starting material in 93% yield. LCMS for $C_7H_{14}N_5O_3$ $(M+H)^+$: m/z=216.1.

Step 2: N'-Hydroxy-4-[(3-methoxypropyl)amino]-1,2,5-oxadiazole-3-carboximidamide The desired compound was prepared according to the procedure of Example 5, step 4, using 4-amino-N'-hydroxy-N-(3-methoxypropyl)-1,2,5-oxadiazole-3-carboximidamide as the starting material in 72% yield. LCMS for $C_7H_{14}N_5O_3$ $(M+H)^+$: m/z=216.1. $^1$H NMR (300 MHz, DMSO-$d_6$): δ 10.4 (s, 1H), 6.21-6.13 (m, 3H), 3.37 (t, J=6.1 Hz, 2H), 3.28-3.21 (m, 5H), 1.82-1.74 (m, 2H).

Step 3: N-Hydroxy-4-[(3-methoxypropyl)amino]-1,2,5-oxadiazole-3-carboximidoyl chloride The desired compound was prepared according to the procedure of Example 5, step 5, using N'-Hydroxy-4-[(3-methoxypropyl)amino]-1,2,5-oxadiazole-3-carboximidamide as the starting material in quantitative yield. LCMS for $C_7H_{12}C_1N_4O_3(M+H)^+$: m/z=235.1.

Step 4: N-[4-Fluoro-3-(trifluoromethyl)phenyl]-N'-hydroxy-4-[(3-methoxypropyl)amino]-1,2,5-oxadiazole-3-carboximidamide The desired compound was prepared according to the procedure of Example 5, step 6, using N-hydroxy-4-[(3-methoxypropyl)amino]-1,2,5-oxadiazole-3-carboximidoyl chloride and 4-fluoro-3-(trifluoromethyl)benzeneamine as the starting materials in 87% yield. LCMS for $C_{14}H_{16}F_4N_5O_3(M+H)^+$: m/z=378.1. $^1$H NMR (400 MHz, DMSO-$d_6$): δ 11.5 (s, 1H), 9.05 (s, 1H), 7.30 (dd, J=10.0, 9.6 Hz, 1H), 7.13-7.11 (m, 1H), 7.05-7.00 (m, 1H), 6.22 (t, J=5.7 Hz, 1H), 3.35-3.32 (m, 2H), 3.25-3.19 (m, 5H), 1.79-1.72 (m, 2H).

Step 5: 4-[4-Fluoro-3-(trifluoromethyl)phenyl]-3-{4-[(3-methoxypropyl)amino]-1,2,5-oxadiazol-3-yl}-1,2,4-oxadiazol-5(4H)-one The desired compound was prepared according to the procedure of Example 5, step 7, using N-[4-fluoro-3-(trifluoromethyl)phenyl]-N'-hydroxy-4-[(3-methoxypropyl)amino]-1,2,5-oxadiazole-3-carboximidamide as the starting material in quantitative yield. LCMS for $C_{15}H_{14}F_4N_5O_4(M+H)^+$: m/z=404.0.

Step 6: 4-[4-Fluoro-3-(trifluoromethyl)phenyl]-3-{4-[(3-hydroxypropyl)amino]-1,2,5-oxadiazol-3-yl}-1,2,4-oxadiazol-5(4H)-one The desired compound was prepared according to the procedure of Example 7, step 4, using 4-[4-fluoro-3-(trifluoromethyl)phenyl]-3-{4-[(3-methoxypropyl)amino]-1,2,5-oxadiazol-3-yl}-1,2,4-oxadiazol-5(4H)-one as the starting material in 97% yield. LCMS for $C_{14}H_{12}F_4N_5O_4(M+H)^+$: m/z=390.0. $^1$H NMR (300 MHz, DMSO-$d_6$): δ 8.20 (dd, J=6.4, 2.6 Hz, 1H), 8.06-8.01 (m, 1H), 7.75 (dd, J=10.0, 9.4 Hz, 1H), 6.53 (t, J=5.7 Hz, 1H), 4.59 (t, J=5.0 Hz, 1H), 3.51-3.42 (m, 2H), 3.32-3.26 (m, 2H), 1.73-1.68 (m, 2H).

Step 7: 3-{4-[(3-Azidopropyl)amino]-1,2,5-oxadiazol-3-yl}-4-[4-fluoro-3-(trifluoromethyl)phenyl]-1,2,4-oxadiazol-5(4H)-one The desired compound was prepared according to the procedure of Example 7, step 5, using 4-[4-fluoro-3-(trifluoromethyl)phenyl]-3-{4-[(3-hydroxypropyl)amino]-1,2,5-oxadiazol-3-yl}-1,2,4-oxadiazol-5(4H)-one as the starting material in quantitative yield. LCMS for $C_{14}H_{10}F_4N_8O_3Na$ $(M+Na)^+$: m/z=437.0.

Step 8: 3-{4-[(3-Aminopropyl)amino]-1,2,5-oxadiazol-3-yl}-4-[4-fluoro-3-(trifluoromethyl)phenyl]-1,2,4-oxadiazol-5(4H)-one hydroiodide The desired compound was prepared according to the procedure of Example 7, step 6, using 3-{4-[(3-azidopropyl)amino]-1,2,5-oxadiazol-3-yl}-4-[4-fluoro-3-(trifluoromethyl)phenyl]-1,2,4-oxadiazol-5(4H)-one as the starting material in 81% yield. LCMS for $C_{14}H_{13}F_4N_6O_3(M+H)^+$: m/z=389.1. $^1$H NMR (300 MHz, DMSO-$d_6$): δ 8.18 (dd, J=6.4, 2.3 Hz, 1H), 8.06-8.01 (m, 1H), 7.72 (dd, J=9.7, 9.4 Hz, 1H), 7.34 (br s, 2H), 6.71 (br s, 1H), 2.78-2.73 (m, 2H), 1.85-1.75 (m, 2H).

Step 9: 4-({3-[(Aminosulfonyl)amino]propyl}amino)-N-[4-fluoro-3-(trifluoromethyl)phenyl]-N'-hydroxy-1,2,5-oxadiazole-3-carboximidamide

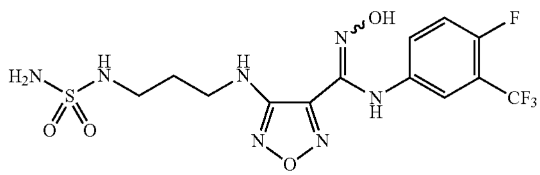 [SMILES: NS(=O)(=O)NCCCNc1nonc1C(=NO)Nc1ccc(F)c(C(F)(F)F)c1]

The desired compound was prepared according to the procedure of Example 19, step 7, using 3-{4-[(3-aminopropyl)amino]-1,2,5-oxadiazol-3-yl}-4-[4-fluoro-3-(trifluoromethyl)phenyl]-1,2,4-oxadiazol-5(4H)-one hydroiodide as the starting material in 60% yield. LCMS for $C_{13}H_{16}F_4N_7O_4S$ $(M+H)^+$: m/z=442.0. $^1H$ NMR (300 MHz, DMSO-$d_6$): δ 11.6 (s, 1H), 9.08 (s, 1H), 7.31 (dd, J=10.0, 9.4 Hz, 1H), 7.13 (dd, J=6.4, 2.9 Hz, 1H), 7.05-6.99 (m, 1H), 6.58 (t, J=6.0 Hz, 1H), 6.52 (s, 2H), 6.17 (t, J=5.9 Hz, 1H), 3.28-3.21 (m, 2H), 2.94-2.87 (m, 2H), 1.79-1.72 (m, 2H).

Example 12

N-[4-Fluoro-3-(trifluoromethyl)phenyl]-N'-hydroxy-4-({3-[(methylsulfonyl)amino]propyl}amino)-1,2,5-oxadiazole-3-carboximidamide

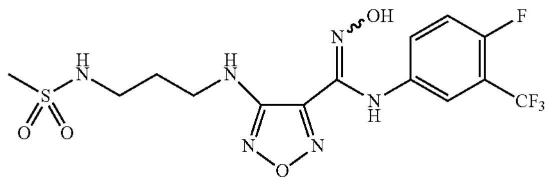 [SMILES: CS(=O)(=O)NCCCNc1nonc1C(=NO)Nc1ccc(F)c(C(F)(F)F)c1]

The desired compound was prepared according to the procedure of Example 20 using 3-{4-[(3-aminopropyl)amino]-1,2,5-oxadiazol-3-yl}-4-[4-fluoro-3-(trifluoromethyl) phenyl]-1,2,4-oxadiazol-5(4H)-one hydroiodide as the starting material in 70% yield. LCMS for $C_{14}H_{17}F_4N_6O_4S$ $(M+H)^+$: m/z=441.1. $^1H$ NMR (400 MHz, DMSO-$d_6$): δ 11.6 (s, 1H), 9.07 (s, 1H), 7.30 (dd, J=10.0, 9.6 Hz, 1H), 7.13 (dd, J=6.2, 2.5 Hz, 1H), 7.05-7.02 (m, 2H), 6.19 (t, J=5.8 Hz, 1H), 3.27-3.21 (m, 2H), 2.99-2.94 (m, 2H), 2.87 (s, 3H), 1.76-1.72 (m, 2H).

Example 13

4-({2-[(Aminosulfonyl)amino]ethyl}amino)-N'-hydroxy-N-[3-(trifluoromethyl)phenyl]-1,2,5-oxadiazole-3-carboximidamide

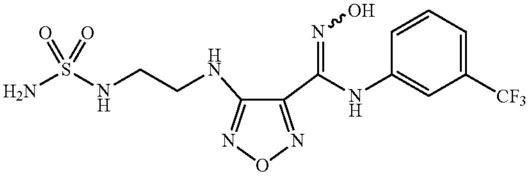 [SMILES: NS(=O)(=O)NCCNc1nonc1C(=NO)Nc1cccc(C(F)(F)F)c1]

Step 1: N'-hydroxy-4-[(2-methoxyethyl)amino]-N-[3-(trifluoromethyl)phenyl]-1,2,5-oxadiazole-3-carboximidamide N-Hydroxy-4-[(2-methoxyethyl)amino]-1,2,5-oxadiazole-3-carboximidoyl chloride (1.3 g, 5.0 mmol) [made according to Example 5, steps 1 through 5] was stirred in water (10 mL) and warmed to 60° C. for 5 minutes. 3-(trifluoromethyl)aniline [Aldrich, product #A41801] (880 mg, 5.5 mmol) was added in one portion and the reaction stirred for 15 minutes. While remaining at 60° C., a solution of sodium bicarbonate (630 mg, 7.5 mmol) in water (10 mL) was added dropwise over 5 minutes. The reaction was stirred at 60° C. for an additional 50 minutes, and then allowed to cool to room temperature. Ethyl acetate (20 mL) and brine (30 mL) were added to the flask and the organic layer was collected. The aqueous layer was extracted with ethyl acetate (2×20 mL) and the combined organics were dried over sodium sulfate. The solvent was removed in vacuo to give the desired product as an orange solid (1.4 g, 80%). LCMS calculated for $C_{13}H_{15}F_3N_5O_3$ $(M+H)^+$: m/z=346.1. $^1H$ NMR (400 MHz, $CD_3OD$): δ 7.36 (t, J=8.2 Hz, 1H), 7.23 (d, J=7.6 Hz, 1H), 7.09 (s, 1H), 7.02 (d, J=8.2 Hz, 1H), 3.60 (t, J=5.2 Hz, 2H), 3.46 (t, J=5.2 Hz, 2H), 3.38 (s, 3H).

Step 2: 3-{4-[(2-Methoxyethyl)amino]-1,2,5-oxadiazol-3-yl}-4-[3-(trifluoromethyl)phenyl]-1,2,4-oxadiazol-5(4H)-one N'-Hydroxy-4-[(2-methoxyethyl)amino]-N-[3-(trifluoromethyl)phenyl]-1,2,5-oxadiazole-3-carboximidamide (1.4 g, 3.80 mmol) and 1,1'-carbonyldiimidazole (1.16 g, 7.16 mmol) were dissolved in ethyl acetate (20 mL). The reaction mixture was heated at 70° C. for 40 minutes. Additional 1,1'-carbonyldiimidazole (0.26 g, 1.16 mmol) was added. After stirring at 70° C. for another 50 minutes, the reaction was allowed to cool to room temperature. Ethyl acetate (20 mL) was added and the crude reaction was washed with 1 N HCl in water (2×20 mL). Brine was added to aid in the separation of the first wash. The organic layer was dried over sodium sulfate and concentrated in vacuo. Purification by flash chromatography on silica gel with an eluent of ethyl acetate in hexanes gave the desired product (1.3 g, 90%). LCMS calculated for $C_{14}H_{13}F_3N_5O_4$ $(M+H)^+$: m/z=372.0. $^1H$ NMR (400 MHz, DMSO-$d_6$): δ 8.07 (s, 1H), 7.92 (m, 2H), 7.79 (t, J=8.1 Hz, 1H), 6.42 (t, J=6.0 Hz, 1H), 3.47 (t, J=5.8 Hz, 2H), 3.38 (q, J=5.0 Hz, 2H), 3.24 (s, 3H).

Step 3: 3-{4-[(2-Hydroxyethyl)amino]-1,2,5-oxadiazol-3-yl}-4-[3-(trifluoromethyl)phenyl]-1,2,4-oxadiazol-5(4H)-one In a round bottom flask under nitrogen atmosphere, 3-{4-[(2-methoxyethyl)amino]-1,2,5-oxadiazol-3-yl}-4-[3-(trifluoromethyl)phenyl]-1,2,4-oxadiazol-5(4H)-one (1.3 g, 3.6 mmol) was stirred in dichloromethane (11 mL). The temperature was brought to −78° C. and a solution of 1.0 M boron tribromide in dichloromethane (7.9 mL, 7.9 mmol) was added dropwise over 15 minutes. The reaction was warmed to room temperature over 45 minutes and continued to stir at room temperature for an additional 45 minutes. The reaction was cooled to 0° C. and a saturated solution of sodium bicarbonate in water (25 mL) was added dropwise over 15 minutes. After warming to room temperature, ethyl acetate (10 mL) and water (10 mL) were added to the flask. The organic layer was collected and the aqueous layer was extracted with ethyl acetate (2×20 mL). After drying the combined organic layers over sodium sulfate, the solvent was removed in vacuo to give the desired product (1.0 g, 81%). LCMS calculated for $C_{13}H_{11}F_3N_5O_4$ $(M+H)^+$: m/z=358.0. $^1$H NMR (400 MHz, DMSO-$d_6$): δ 8.08 (s, 1H), 7.93 (t, J=8.2 Hz, 2H), 7.79 (t, J=8.2 Hz, 1H), 6.35 (t, J=5.7 Hz, 1H), 4.86 (br s, 1H), 3.55 (t, J=6.0 Hz, 2H), 3.28 (m, 2H).

Step 4: 2-[(4-{5-Oxo-4-[3-(trifluoromethyl)phenyl]-4,5-dihydro-1,2,4-oxadiazol-3-yl}-1,2,5-oxadiazol-3-yl)amino]ethyl methanesulfonate To a solution of 3-{4-[(2-hydroxyethyl)amino]-1,2,5-oxadiazol-3-yl}-4-[3-(trifluoromethyl)phenyl]-1,2,4-oxadiazol-5(4H)-one (1.0 g, 2.9 mmol) in ethyl acetate (8.5 mL) was added methanesulfonyl chloride (0.29 mL, 3.7 mmol) in one portion. The reaction was stirred for 5 minutes and triethylamine (0.52 mL, 3.7 mmol) was added, also in one portion. After stirring for an additional 10 minutes, the reaction was quenched with the addition of water (5 mL). The product was extracted with ethyl acetate (2×5 mL), dried over sodium sulfate and concentrated in vacuo to give the desired product (1.2 g, 99%). LCMS calculated for $C_{14}H_{13}F_3N_5O_6S$ $(M+H)^+$: m/z=436.0. $^1$H NMR (400 MHz, DMSO-$d_6$): δ 8.10 (s, 1H), 7.92 (m, 2H), 7.80 (t, J=8.2 Hz, 1H), 6.77 (t, J=5.9 Hz, 1H), 4.36 (t, J=5.5 Hz, 2H), 3.58 (m, 2H), 3.17 (s, 3H).

Step 5: 3-{4-[(2-Azidoethyl)amino]-1,2,5-oxadiazol-3-yl}-4-[3-(trifluoromethyl)phenyl]-1,2,4-oxadiazol-5(4H)-one 2-[(4-{5-Oxo-4-[3-(trifluoromethyl)phenyl]-4,5-dihydro-1,2,4-oxadiazol-3-yl}-1,2,5-oxadiazol-3-yl)amino]ethyl methanesulfonate (1.2 g, 2.9 mmol) was dissolved in N,N-dimethylformamide (2.7 mL). After sodium azide (280 mg, 4.3 mmol) was added in one portion, the temperature was brought to 65° C. and the reaction stirred for 6 hours. After cooling back to room temperature, water (10 mL) was added to quench the reaction. The product was extracted with ethyl acetate (3×10 mL) and the combined organic layers were dried over sodium sulfate. The solvent was removed in vacuo to give the desired product (1.05 g, 96%). LCMS calculated for $C_{13}H_{10}F_3N_6O_3$ $(M-N_2+H)^+$: m/z=355.0. $^1$H NMR (400 MHz, DMSO-$d_6$): δ 8.09 (s, 1H), 7.93 (m, 2H), 7.79 (t, J=8.2 Hz, 1H), 6.75 (t, J=5.8 Hz, 1H), 3.52 (t, J=5.7 Hz, 2H), 3.44 (q, J=5.5 Hz, 2H).

Step 6: 3-{4-[(2-Aminoethyl)amino]-1,2,5-oxadiazol-3-yl}-4-[3-(trifluoromethyl)phenyl]-1,2,4-oxadiazol-5(4H)-one hydroiodide To a solution of 3-{4-[(2-azidoethyl)amino]-1,2,5-oxadiazol-3-yl}-4-[3-(trifluoromethyl)phenyl]-1,2,4-oxadiazol-5(4H)-one (1.05 g, 2.8 mmol) in methanol (12 mL) was added sodium iodide (2.5 g, 17 mmol). After stirring for 10 minutes, a solution of chlorotrimethylsilane (2.1 mL, 17 mmol) in methanol (1.41 mL) was added dropwise over 15 minutes. The reaction continued to stir for 40 minutes and then a solution of sodium thiosulfate (2.7 g, 17 mmol) in water (12.5 mL) was added in one portion. A beige solid precipitated upon addition of the sodium thiosulfate solution and it was collected by vacuum filtration. The solid was rinsed with water (2×10 mL) and was dried under vacuum overnight to give the desired product. A solid had also precipitated from the filtrate and it was collected by vacuum filtration. After washing with water (3×10 mL) in the funnel, the product was dried overnight under vacuum. The solid was slurry washed with ethyl acetate (3.8 mL) for 1 hour and recollected by filtration. After rinsing with ethyl acetate (2×2 mL) and drying overnight, additional product was obtained. In total, 760 mg of desired product (57%) was obtained as the hydroiodide salt. LCMS calculated for $C_{13}H_{12}F_3N_6O_3$ $(M+H)^+$: m/z=357.1. $^1$H NMR (400 MHz, DMSO-$d_6$): δ 8.10 (s, 1H), 7.95 (m, 2H), 7.81 (t, J=8.1 Hz, 1H), 7.68 (br s, 2H), 6.74 (t, J=6.7 Hz, 1H), 3.49 (m, 2H), 3.03 (t, J=6.7 Hz, 2H).

Step 7: 4-({2-[(Aminosulfonyl)amino]ethyl}amino)-N'-hydroxy-N-[3-(trifluoromethyl)phenyl]-1,2,5-oxadiazole-3-carboximidamide

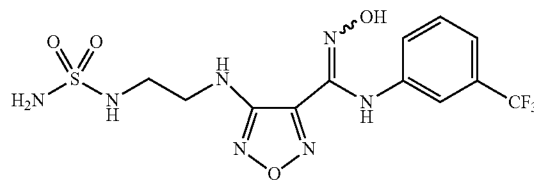 [SMILES: NS(=O)(=O)NCCNc1nonc1C(=NO)Nc1cccc(C(F)(F)F)c1]

To a solution of chlorosulfonyl isocyanate (9.2 μL, 0.11 mmol) in dichloromethane (0.24 mL), at 0° C. and under a nitrogen atmosphere, was added tert-butyl alcohol (10 μL, 0.11 mmol) in a dropwise fashion. The solution was allowed to stir at room temperature for 1 hour to obtain a solution of tert-butyl [chlorosulfonyl]carbamate.

In a separate flask, 3-{4-[(2-aminoethyl)amino]-1,2,5-oxadiazol-3-yl}-4-[3-(trifluoromethyl)phenyl]-1,2,4-oxadiazol-5(4H)-one hydroiodide (26 mg, 0.053 mmol) was suspended in dichloromethane (0.5 mL). A nitrogen atmosphere was established and the temperature brought to 0° C. The tert-butyl [chlorosulfonyl]carbamate solution (prepared as above) was added over 5 minutes to the stirred suspension of the amine salt. After 10 minutes, triethylamine (37 μL, 0.27 mmol) was added dropwise. The reaction mixture was stirred at room temperature for 1.5 hours. After concentrating in vacuo, the residue was treated with trifluoroacetic acid (0.5 mL, 6 mmol). This was stirred for 1 hour and the mixture was again concentrated to dryness in vacuo. The dried solids were suspended in methanol (0.5 mL) and a 2.0 N NaOH in water (0.53 mL, 1.1 mmol) was added in one portion. The reaction was heated to 45° C. and stirred for 30 minutes. After neutralization with acetic acid (60 μL, 1.1 mmol), the product was purified by preparative LCMS to give the desired product (8.5 mg, 39%). LCMS calculated for $C_{12}H_{15}F_3N_7O_4S$ $(M+H)^+$: m/z=410.0. $^1$H NMR (400 MHz, $CD_3OD$): δ 7.36 (t, J=7.8 Hz, 1H), 7.23 (d, J=7.8 Hz, 1H), 7.10 (s, 1H), 7.03 (d, J=7.8 Hz, 1H), 3.48 (m, 2H), 3.29 (m, 2H).

Example 14

N'-Hydroxy-4-({2-[(methylsulfonyl)amino]ethyl}amino)-N-[3-(trifluoromethyl)phenyl]-1,2,5-oxadiazole-3-carboximidamide

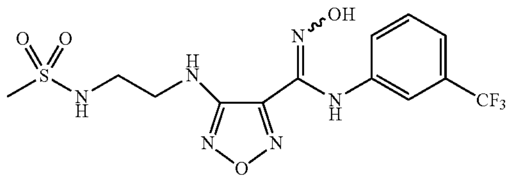 [SMILES: CS(=O)(=O)NCCNc1nonc1C(=NO)Nc1cccc(C(F)(F)F)c1]

The title compound was prepared according to the procedure of Example 32, step 5, using N-hydroxy-4-({2-[(methylsulfonyl)amino]ethyl}amino)-1,2,5-oxadiazole-3-carboximidamide and 3-trifluoromethylaniline [Aldrich, product #A41801] as the starting materials. LCMS for $C_{13}H_{16}F_3N_6O_4S$ $(M+H)^+$: m/z=409.1. $^1$H NMR (500 MHz, DMSO-$d_6$): δ 11.63 (s, 1H), 9.08 (s, 1H), 7.39 (t, J=7.6 Hz, 1H), 7.21 (m, 2H), 7.10 (s, 1H), 6.99 (d, J=8.1 Hz, 1H), 6.28 (t, J=5.4 Hz, 1H), 3.36 (q, J=5.8 Hz, 2H), 3.17 (q, J=5.8 Hz, 2H), 2.91 (s, 3H).

Example 15

4-({3-[(Aminosulfonyl)amino]propyl}amino)-N'-hydroxy-N-[3-(trifluoromethyl)phenyl]-1,2,5-oxadiazole-3-carboximidamide

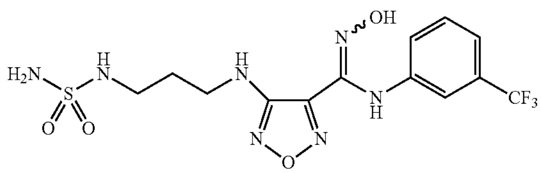 [SMILES: NS(=O)(=O)NCCCNc1nonc1C(=NO)Nc1cccc(C(F)(F)F)c1]

Step 1: 3-(4-Amino-1,2,5-oxadiazol-3-yl)-4-[3-(trifluoromethyl)phenyl]-1,2,4-oxadiazol-5(4H)-one The desired compound was prepared according to the procedure of Example 9, step 1, using 4-amino-N'-hydroxy-N-[3-(trifluoromethyl)phenyl]-1,2,5-oxadiazole-3-carboximidamide [see US Pat. App. Pub. No. 2006/0258719] as the starting material in 97% yield. LCMS for $C_{11}H_7F_3N_5O_3$ $(M+H)^+$: m/z=314.1.

Step 2: 2,2,2-Trifluoro-N-(4-{5-oxo-4-[3-(trifluoromethyl)phenyl]-4,5-dihydro-1,2,4-oxadiazol-3-yl}-1,2,5-oxadiazol-3-yl)acetamide The desired compound was prepared according to the procedure of Example 9, step 2, using 3-(4-amino-1,2,5-oxadiazol-3-yl)-4-[3-(trifluoromethyl)phenyl]-1,2,4-oxadiazol-5(4H)-one as the starting material in 90% yield. LCMS for $C_{13}H_6F_6N_5O_4$ $(M+H)^+$: m/z=410.0. $^1$H NMR (400 MHz, DMSO-$d_6$): δ 7.91-7.88 (m, 2H), 7.76-7.69 (m, 2H).

Step 3: 3-{4-[(3-Methoxypropyl)amino]-1,2,5-oxadiazol-3-yl}-4-[3-(trifluoromethyl)phenyl]-1,2,4-oxadiazol-5(4H)-one The desired compound was prepared according to the procedure of Example 7, step 3, using 2,2,2-trifluoro-N-(4-{5-oxo-4-[3-(trifluoromethyl)phenyl]-4,5-dihydro-1,2,4-oxadiazol-3-yl}-1,2,5-oxadiazol-3-yl)acetamide as the starting material in 49% yield. LCMS for $C_{15}H_{15}F_3N_5O_4$$(M+H)^+$: m/z=386.1. $^1$H NMR (300 MHz, $CDCl_3$): δ 7.83 (d, J=8.1 Hz, 1H), 7.72-7.67 (m, 2H), 7.59 (d, J=7.5 Hz, 1H), 6.08-6.04 (m, 1H), 3.57 (t, J=5.6 Hz, 2H), 3.54-3.47 (m, 2H), 3.40 (s, 3H), 2.01-1.93 (m, 2H).

Step 4: 3-{4-[(3-Hydroxypropyl)amino]-1,2,5-oxadiazol-3-yl}-4-[3-(trifluoromethyl)phenyl]-1,2,4-oxadiazol-5(4H)-one The desired compound was prepared according to the procedure of Example 7, step 4, using 3-{4-[(3-methoxypropyl)amino]-1,2,5-oxadiazol-3-yl}-4-[3-(trifluoromethyl)phenyl]-1,2,4-oxadiazol-5(4H)-one as the starting material in 69% yield. LCMS for $C_{14}H_{13}F_3N_5O_4$$(M+H)^+$: m/z=372.1. $^1$H NMR (400 MHz, DMSO-$d_6$): δ 8.07 (s, 1H), 7.95-7.90 (m, 2H), 7.79 (dd, J=7.9, 7.9 Hz, 1H), 6.55 (t, J=5.6 Hz, 1H), 4.59 (t, J=5.1 Hz, 1H), 3.47-3.42 (m, 2H), 3.30-3.25 (m, 2H), 1.72-1.65 (m, 2H).

Step 5: 3-{4-[(3-Azidopropyl)amino]-1,2,5-oxadiazol-3-yl}-4-[3-(trifluoromethyl)phenyl]-1,2,4-oxadiazol-5(4H)-one The desired compound was prepared according to the procedure of Example 7, step 5, using 3-{4-[(3-hydroxypropyl)amino]-1,2,5-oxadiazol-3-yl}-4-[3-(trifluoromethyl)phenyl]-1,2,4-oxadiazol-5(4H)-one as the starting material in 92% yield. LCMS for $C_{14}H_{11}F_3N_8O_3Na$ $(M+Na)^+$: m/z=419.0.

Step 6: 3-{4-[(3-Aminopropyl)amino]-1,2,5-oxadiazol-3-yl}-4-[3-(trifluoromethyl)phenyl]-1,2,4-oxadiazol-5(4H)-one hydroiodide The desired compound was prepared according to the procedure of Example 7, step 6, using 3-{4-[(3-azidopropyl)amino]-1,2,5-oxadiazol-3-yl}-4-[3-(trifluoromethyl)phenyl]-1,2,4-oxadiazol-5(4H)-one as the starting material in 92% yield. LCMS for $C_{14}H_{14}F_3N_6O_3$ $(M+H)^+$: m/z=371.1. $^1$H NMR (400 MHz, DMSO-$d_6$): δ 8.09 (s, 1H), 7.96-7.92 (m, 2H), 7.80 (dd, J=8.0, 7.8 Hz, 1H), 7.53 (br s, 2H), 6.70-6.65 (m, 1H), 4.10 (br s, 1H), 3.32-3.31 (m, 2H), 2.81-2.78 (m, 2H), 1.85-1.82 (m, 2H).

Step 7: 4-({3-[(Aminosulfonyl)amino]propyl}amino)-N'-hydroxy-N-[3-(trifluoromethyl)phenyl]-1,2,5-oxadiazole-3-carboximidamide

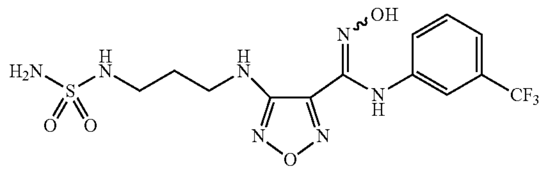 [SMILES: NS(=O)(=O)NCCCNc1nonc1C(=NO)Nc1cccc(C(F)(F)F)c1]

A solution of 3-{4-[(3-aminopropyl)amino]-1,2,5-oxadiazol-3-yl}-4-[3-(trifluoromethyl)phenyl]-1,2,4-oxadiazol-5 (4H)-one hydroiodide (1.5 g, 3.0 mmol) and sulfamide (1.7 g, 18 mmol) in pyridine (60 mL) was heated in a microwave at 130° C. for 10 min. The reaction mixture was concentrated to give the crude intermediate N-{3-[(4-{5-oxo-4-[3-(trifluoromethyl)phenyl]-4,5-dihydro-1,2,4-oxadiazol-3-yl}-1,2,5-oxadiazol-3-yl)amino]propyl}sulfamide. A solution of the crude intermediate in methanol (90 mL) was treated with 2 N NaOH (12 mL, 24 mmol) and stirred at 25° C. for 30 min. The reaction mixture was treated with 6 M HCl until the solution was acidic and extracted with ethyl acetate (250 mL). The organic layer was washed with water (100 mL) and brine (100 mL), dried over anhydrous sodium sulfate, filtered, and concentrated to give a crude residue. This material was purified by preparative LCMS to give the desired product (1.1 g, 82%) as a gummy solid. LCMS for $C_{13}H_{17}F_3N_7O_4S$ $(M+H)^+$: m/z=424.0. $^1H$ NMR (400 MHz, DMSO-$d_6$): δ 11.6 (s, 1H), 9.12 (s, 1H), 7.37 (dd, J=8.0, 8.0 Hz, 1H), 7.21-7.18 (m, 1H), 7.07 (s, 1H), 6.95 (d, J=10.0 Hz, 1H), 6.52 (br s, 3H), 6.17 (t, J=6.0 Hz, 1H), 3.28-3.22 (m, 2H), 2.93-2.89 (m, 2H), 1.77-1.73 (m, 2H).

Example 16

N'-Hydroxy-4-({3-[(methylsulfonyl)amino]propyl}amino)-N-[3-(trifluoromethyl)phenyl]-1,2,5-oxadiazole-3-carboximidamide

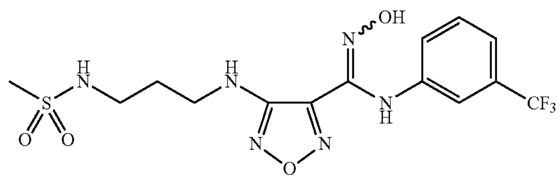 [SMILES: CS(=O)(=O)NCCCNc1nonc1C(=NO)Nc1cccc(C(F)(F)F)c1]

A solution of 3-{4-[(3-aminopropyl)amino]-1,2,5-oxadiazol-3-yl}-4-[3-(trifluoromethyl)phenyl]-1,2,4-oxadiazol-5 (4H)-one hydroiodide (from Example 19, step 6; 25 mg, 50 μmol) in dichloromethane (1 mL) was treated with triethylamine (17 μL, 0.12 mmol) and methanesulfonyl chloride (6 μL, 70 μmol) and stirred at 25° C. for 2 h. The reaction mixture was concentrated to give the intermediate, N-{3-[(4-{5-oxo-4-[3-(trifluoromethyl)phenyl]-4,5-dihydro-1,2,4-oxadiazol-3-yl}-1,2,5-oxadiazol-3-yl)amino]propyl}methanesulfonamide, as a crude residue which was used without further purification. A solution of the crude intermediate in methanol (1 mL) was treated with 2 N NaOH (0.25 mL, 0.5 mmol) and stirred at 25° C. for 30 min. The reaction mixture was treated with acetic acid (50 μL, 0.9 mmol), filtered and purified by preparative LCMS to give the desired product (13 mg, 65%) as a solid. LCMS for $C_{14}H_{18}F_3N_6O_4S$ $(M+H)^+$: m/z=423.1. $^1H$ NMR (400 MHz, DMSO-$d_6$): δ 11.6 (s, 1H), 9.11 (s, 1H), 7.37 (dd, J=8.0, 8.0 Hz, 1H), 7.20 (d, J=7.8 Hz, 1H), 7.07-7.01 (m, 2H), 6.96 (d, J=8.0 Hz, 1H), 6.20 (t, J=5.9 Hz, 1H), 3.27-3.22 (m, 2H), 2.99-2.94 (m, 2H), 2.87 (s, 3H), 1.78-1.71 (m, 2H).

Example 17

N-(4-Fluoro-3-methylphenyl)-N'-hydroxy-4-({2-[(methylsulfonyl)amino]ethyl}amino)-1,2,5-oxadiazole-3-carboximidamide

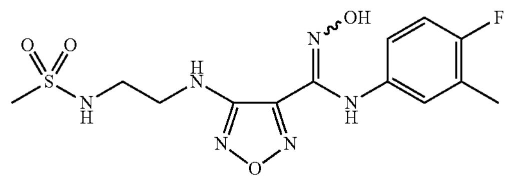

Step 1: tert-Butyl {2-[(methylsulfonyl)amino]ethyl}carbamate

N-(2-Aminoethyl)(tert-butoxy)carboxamide (17.5 mL, 0.11 mol) [Alfa #L19947] was stirred in dichloromethane (320 mL) and triethylamine (33 mL, 0.24 mol) was added. A solution of methanesulfonyl chloride (8.5 mL, 0.11 mol) in dichloromethane (10 mL) was added. The resulting mixture was stirred for 1 hour and water (30 mL) was added. The product was extracted with dichloromethane (3×30 mL), dried over sodium sulfate and concentrated in vacuo to give the desired product (21 g, 81%). LCMS calculated for $C_3H_{11}N_2O_2S$ $(M-Boc+H)^+$: m/z=139.1.

Step 2: N-(2-Aminoethyl)methanesulfonamide dihydrochloride tert-Butyl {2-[(methylsulfonyl)amino]ethyl}carbamate (21 g, 88 mmol) was stirred in a solution of 4 N hydrogen chloride in 1,4-dioxane (97 mL, 388 mmol) for 30 minutes. Trituration with ethyl acetate and hexanes followed by diethyl ether and hexanes gave the desired compound as a gum (19 g, 100%). LCMS calculated for $C_3H_{11}N_2O_2S$ $(M+H)^+$: m/z=139.0.

Step 3: 4-Amino-N'-hydroxy-N-{2-[(methylsulfonyl)amino]ethyl}-1,2,5-oxadiazole-3-carboximidamide 4-Amino-N-hydroxy-1,2,5-oxadiazole-3-carboximidoyl chloride (9.7 g, 60 mmol) was stirred in ethanol (460 mL) and N-(2-aminoethyl)methanesulfonamide dihydrochloride (19 g, 109 mmol) was added slowly in portions and the temperature rose to 25° C. After cooling back to 0° C., triethylamine (53 mL, 380 mmol) was added dropwise over 15 minutes and the reaction was stirred for an additional 15 minutes. The solution was washed with water (300 mL) and brine (300 mL). The organic layer was dried over sodium sulfate and concentrated in vacuo to give the desired product (16 g, 100%). LCMS calculated for $C_6H_{13}N_6O_4S$ $(M+H)^+$: m/z=265.1. $^1H$ NMR (400 MHz, DMSO-$d_6$): δ 10.16 (s, 1H), 9.07 (m, 1H), 7.18 (m, 1H), 6.37 (s, 2H), 3.36 (m, 2H), 3.15 (m, 2H), 2.87 (s, 3H).

Step 4: N'-Hydroxy-4-({2-[(methylsulfonyl)amino]ethyl}amino)-1,2,5-oxadiazole-3-carboximidamide 4-Amino-N'-hydroxy-N-{2-[(methylsulfonyl)amino]ethyl}-1,2,5-oxadiazole-3-carboximidamide (0.47 g, 1.8 mmol) was stirred in 1,2-ethanediol (38 mL). Potassium hydroxide (600 g, 11 mmol) was added in one portion. The reaction was heated at 130° C. for 4 hours and allowed to cool to room temperature. 1 N HCl solution (60 mL) was added and the product was extracted with ethyl acetate (4×40 mL). The combined organics were dried over sodium sulfate and concentrated in vacuo to give the desired product (0.45 g, 96%). LCMS calculated for $C_6H_{12}N_6O_4S$ $(M+H)^+$: m/z=265.1. $^1H$ NMR (400 MHz, DMSO-$d_6$): δ 10.49 (s, 1H), 7.18 (m, 1H), 6.20 (m, 3H), 3.36 (m, 2H), 3.15 (m, 2H), 2.87 (s, 3H).

Step 5: N-(4-Fluoro-3-methylphenyl)-N'-hydroxy-4-({2-[(methylsulfonyl)amino]ethyl}amino)-1,2,5-oxadiazole-3-carboximidamide

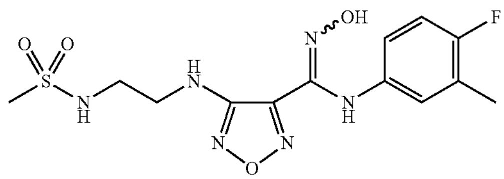 [SMILES: Cc1cc(NC(=NO)c2nonc2NCCNS(C)(=O)=O)ccc1F]

N-Hydroxy-4-({2-[(methylsulfonyl)amino]ethyl}amino)-1,2,5-oxadiazole-3-carboximidamide (35 mg, 0.13 mmol) was stirred in 1,4-dioxane (2 mL) and 6 N hydrogen chloride solution (4 mL) was added. The solution was cooled to 0° C. and a solution of sodium nitrite (11 mg, 0.16 mmol) in water (3 mL) was slowly added. The mixture was stirred for 1 hour at 0° C. and evaporated. Dry 1,4-dioxane (2 mL) was added and the mixture evaporated two more times. A solution of 4-fluoro-3-methylaniline [Aldrich, product #559415] (25 mg, 0.20 mmol) in ethanol (2 mL) was added and the mixture was stirred for 1 hour. Purification by preparative LCMS (pH 2) gave the desired compound (17 mg, 27%). LCMS calculated for $C_{13}H_{18}FN_6O_4S$ $(M+H)^+$: m/z=373.1. $^1H$ NMR (400 MHz, DMSO-$d_6$): δ 11.25 (s, 1H), 8.61 (s, 1H), 7.18 (m, 1H), 6.91 (m, 1H), 6.72 (m, 1H), 6.58 (m, 1H), 6.24 (s, 1H), 3.32 (m, 2H), 3.11 (m, 2H), 2.89 (s, 3H), 2.05 (s, 3H).

Example 18

4-({2-[(Aminosulfonyl)amino]ethyl}amino)-N-(3-cyano-4-fluorophenyl)-N'-hydroxy-1,2,5-oxadiazole-3-carboximidamide

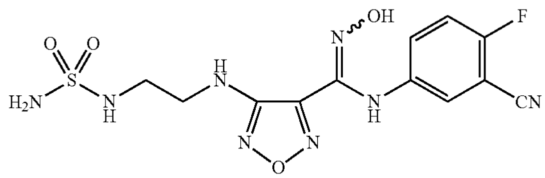 [SMILES: N#Cc1cc(NC(=NO)c2nonc2NCCNS(N)(=O)=O)ccc1F]

Step 1: N-(3-Cyano-4-fluorophenyl)-N'-hydroxy-4-[(2-methoxyethyl)amino]-1,2,5-oxadiazole-3-carboximidamide The desired compound was prepared according to the procedure of Example 17, step 1, using N-hydroxy-4-[(2-methoxyethyl)amino]-1,2,5-oxadiazole-3-carboximidoyl chloride [made according to Example 5, steps 1 through 5] and 5-amino-2-fluorobenzonitrile [Aldrich, product #639877] as the starting materials in 100% yield. LCMS for $C_{13}H_{14}FN_6O_3$ $(M+H)^+$: m/z=321.0.

Step 2: 2-Fluoro-5-[3-{4-[(2-methoxyethyl)amino]-1,2,5-oxadiazol-3-yl}-5-oxo-1,2,4-oxadiazol-4(5H)-yl]benzonitrile The desired compound was prepared according to the procedure of Example 17, step 2, using N-(3-cyano-4-fluorophenyl)-N'-hydroxy-4-[(2-methoxyethyl)amino]-1,2,5-oxadiazole-3-carboximidamide as the starting material in 91% yield. LCMS for $C_{14}H_{12}FN_6O_4$ $(M+H)^+$: m/z=347.0. $^1H$ NMR (400 MHz, DMSO-$d_6$): δ 8.25 (dd, J=5.7, 2.6 Hz, 1H), 8.06 (m, 1H), 7.77 (t, J=9.2 Hz, 1H), 6.41 (t, J=5.7 Hz, 1H), 3.48 (m, 2H), 3.40 (q, J=5.4 Hz, 2H), 3.25 (s, 3H).

Step 3: 2-Fluoro-5-[3-{4-[(2-hydroxyethyl)amino]-1,2,5-oxadiazol-3-yl}-5-oxo-1,2,4-oxadiazol-4(5H)-yl]benzonitrile The desired compound was prepared according to the procedure of Example 17, step 3, using 2-fluoro-5-[3-{4-[(2-methoxyethyl)amino]-1,2,5-oxadiazol-3-yl}-5-oxo-1,2,4-oxadiazol-4(5H)-yl]benzonitrile as the starting material in quantitative yield. LCMS for $C_{13}H_{10}FN_6O_4$ $(M+H)^+$: m/z=333.0.

Step 4: 2-({4-[4-(3-Cyano-4-fluorophenyl)-5-oxo-4,5-dihydro-1,2,4-oxadiazol-3-yl]-1,2,5-oxadiazol-3-yl}amino)ethyl methanesulfonate The desired compound was prepared according to the procedure of Example 17, step 4, using 2-fluoro-5-[3-{4-[(2-hydroxyethyl)amino]-1,2,5-oxadiazol-3-yl}-5-oxo-1,2,4-oxadiazol-4(5H)-yl]benzonitrile as the starting material in 88% yield. LCMS for $C_{14}H_{12}FN_6O_6S$ $(M+H)^+$: m/z=411.0.

Step 5: 5-[3-{4-[(2-Azidoethyl)amino]-1,2,5-oxadiazol-3-yl}-5-oxo-1,2,4-oxadiazol-4(5H)-yl]-2-fluorobenzonitrile The desired compound was prepared according to the procedure of Example 17, step 5, using 2-({4-[4-(3-cyano-4-fluorophenyl)-5-oxo-4,5-dihydro-1,2,4-oxadiazol-3-yl]-1,2,5-oxadiazol-3-yl}amino)ethyl methanesulfonate as the starting material in 95% yield.

Step 6: 5-[3-{4-[(2-Aminoethyl)amino]-1,2,5-oxadiazol-3-yl}-5-oxo-1,2,4-oxadiazol-4(5H)-yl]-2-fluorobenzonitrile hydroiodide The desired compound was prepared according to the procedure of Example 17, step 6, using 5-[3-{4-[(2-azidoethyl)amino]-1,2,5-oxadiazol-3-yl}-5-oxo-1,2,4-oxadiazol-4(5H)-yl]-2-fluorobenzonitrile as the starting material in 57% yield. LCMS for $C_{13}H_{11}FN_7O_3$ $(M+H)^+$: m/z=332.0. $^1H$ NMR (400 MHz, DMSO-$d_6$): δ 8.29 (dd, J=5.8, 2.7 Hz, 1H), 8.09 (m, 1H), 7.83 (br s, 3H), 7.79 (t, J=9.0 Hz, 1H), 6.77 (t, J=5.9 Hz, 1H), 3.50 (q, J=6.4 Hz, 2H), 3.04 (m, 2H).

Step 7: 4-({2-[(Aminosulfonyl)amino]ethyl}amino)-N-(3-cyano-4-fluorophenyl)-N'-hydroxy-1,2,5-oxadiazole-3-carboximidamide

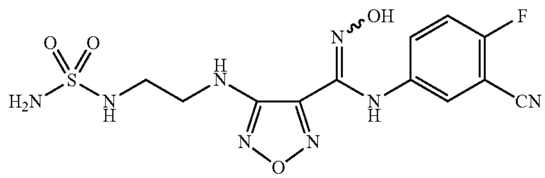 [SMILES: N#Cc1cc(NC(=NO)c2nonc2NCCNS(N)(=O)=O)ccc1F]

In a microwave vial, 5-[3-{4-[(2-aminoethyl)amino]-1,2,5-oxadiazol-3-yl}-5-oxo-1,2,4-oxadiazol-4(5H)-yl]-2-fluorobenzonitrile hydroiodide (20.0 mg, 0.044 mmol) and sulfamide (25 mg, 0.26 mmol) were suspended in pyridine (0.5 mL). The reaction was heated to 120° C. for 10 minutes in a microwave reactor. The solvent was removed and the residue dissolved in methanol (0.17 mL). A solution of 2.0 N NaOH in water (0.22 mL, 0.44 mmol) was added in one portion. The reaction was stirred at room temperature overnight. After neutralization with acetic acid (50 μL), the product was purified using preparative LCMS to give the title compound (4.9 mg, 29%). LCMS for $C_{12}H_{14}FN_8O_4S$ $(M+H)^+$: m/z=385.0. $^1H$ NMR (400 MHz, DMSO-$d_6$): δ 11.65 (s, 1H), 9.08 (s, 1H), 7.34 (t, J=9.1 Hz, 1H), 7.22 (dd, J=5.4, 2.8 Hz, 1H), 7.13 (m, 1H), 6.70 (t, J=5.9 Hz, 1H), 6.59 (s, 2H), 6.20 (t, J=6.1 Hz, 1H), 3.34 (m, 2H), 3.09 (m, 2H).

Example 19

N-(3-Cyano-4-fluorophenyl)-N'-hydroxy-4-({2-[(methylsulfonyl)amino]ethyl}amino)-1,2,5-oxadiazole-3-carboximidamide

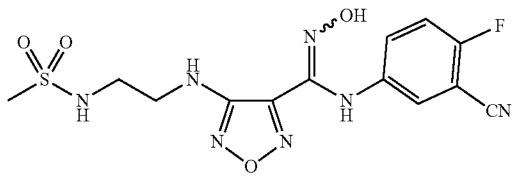 [SMILES: CS(=O)(=O)NCCNc1nonc1C(=NO)Nc1ccc(F)c(C#N)c1]

The title compound was prepared according to the procedure of Example 21, step 5, using N-hydroxy-4-({2-[(methylsulfonyl)amino]ethyl}amino)-1,2,5-oxadiazole-3-carboximidamide and 3-cyano-4-fluoroaniline [Aldrich, product #639877] as the starting materials. LCMS for $C_{13}H_{14}FN_7NaO_4S$ $(M+Na)^+$: m/z=406.0. $^1H$ NMR (400 MHz, DMSO-$d_6$): δ 11.65 (s, 1H), 9.08 (s, 1H), 7.35 (m, 1H), 7.18 (m, 3H), 6.56 (m, 1H), 6.23 (m, 1H), 6.24 (s, 2H), 3.32 (m, 2H), 3.14 (m, 2H), 2.89 (s, 3H).

Example 20

4-({2-[(Aminosulfonyl)amino]ethyl}amino)-N-[(4-bromo-2-furyl)methyl]-N'-hydroxy-1,2,5-oxadiazole-3-carboximidamide

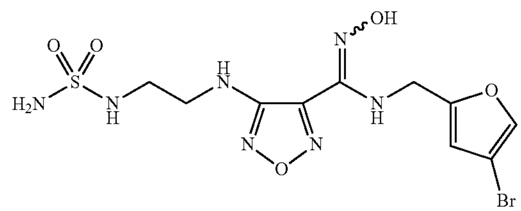 [SMILES: NS(=O)(=O)NCCNc1nonc1C(=NO)NCc1cc(Br)co1]

Step 1: tert-Butyl [(4-bromo-2-furyl)methyl]carbamate

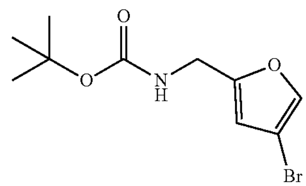

4-Bromo-2-furaldehyde [Aldrich, product #666599] (10.0 g, 57.1 mmol) was dissolved in ethanol (50 mL) and water (50 mL). N-Hydroxyamine hydrochloride (7.15 g, 103 mmol) and sodium acetate (8.44 g, 103 mmol) were added sequentially and the reaction mixture was brought to reflux at 100° C. for 1 hour. The solution was partially concentrated and the precipitate was collected and washed with cold water (2×10 mL). The filtrate was extracted with ethyl acetate (3×25 mL) and the combined organic layers were washed with brine (50 mL). After drying over sodium sulfate, the solution was concentrated in vacuo. The residue was combined with the precipitate and dissolved in acetic acid (70 mL). After placing in an ice-bath, zinc (14.7 g, 225 mmol) was added portion-wise over 25 minutes. The reaction warmed to room temperature over 1.5 hours and was filtered through Celite. The solvent was removed in vacuo.

The residue was stirred in tetrahydrofuran (72 mL). A solution of 2.0 N NaOH in water (179 mL, 358 mmol) was added dropwise over 45 minutes. After 5 minutes, di-tert-butyldicarbonate (16.9 g, 77.4 mmol) was added dropwise. The reaction was stirred for 2 hours and the tetrahydrofuran was removed in vacuo. Ethyl acetate (100 mL) was added and the suspension was filtered. The organic layer was collected and the product extracted with ethyl acetate (2×50 mL). The combined organic layers were washed with brine (100 mL) and water (100 mL), dried over sodium sulfate and concentrated in vacuo to give the desired product (15.3 g, 79%). LCMS calculated for $C_{10}H_{14}BrNNaO_3$ $(M+Na)^+$: m/z=298.0. $^1H$ NMR (400 MHz, DMSO-$d_6$): δ 7.79 (s, 1H), 7.37 (t, J 5.8 Hz, 1H), 6.33 (s, 1H), 4.06 (d, J=6.1 Hz, 2H), 1.36 (s, 9H).

Step 2: 1-(4-Bromo-2-furyl)methanamine trifluoroacetate

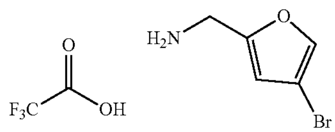 [SMILES: O=C(O)C(F)(F)F ; NCc1cc(Br)co1]

Under a nitrogen atmosphere, a solution of tert-butyl [(4-bromo-2-furyl)methyl]carbamate (15.3 g, 55.4 mmol) in dichloromethane (86 mL) at 0° C. was treated with trifluoroacetic acid (43 mL) over 15 minutes. The reaction mixture warmed to room temperature over 30 minutes. The solvent was removed in vacuo and chased with toluene (3×50 mL). The product was lyophilized for 18 hours to give the desired product as a brown solid (13.0 g, 81%). LCMS calculated for $C_5H_4BrO$ (M-$NH_2$)$^+$: m/z=158.9, 160.9. $^1H$ NMR (400 MHz, DMSO-$d_6$): δ 8.34 (br s, 3H), 8.01 (s, 1H), 6.70 (s, 1H), 4.08 (s, 1H).

Step 3: N-[(4-Bromo-2-furyl)methyl]-N'-hydroxy-4-[(2-methoxyethyl)amino]-1,2,5-oxadiazole-3-carboximidamide

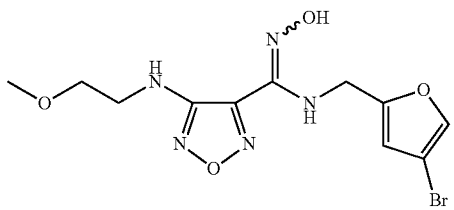 [SMILES: COCCNc1nonc1C(=NO)NCc1cc(Br)co1]

N-Hydroxy-4-(2-methoxyethylamino)-1,2,5-oxadiazole-3-carbimidoyl chloride [prepared according to the procedure of Example 5, steps 1 through 5] (4.5 g, 20.3 mmol) was stirred in ethanol (20 mL) at room temperature. To this, a solution of 1-(4-bromo-2-furyl)methanamine trifluoroacetate (6.5 g, 22.4 mmol) in ethanol (24 mL) was added and the mixture was stirred for 15 minutes. Triethylamine (6.3 mL, 44.8 mmol) was added dropwise over 10 minutes and the reaction was stirred for an additional 15 minutes. The solvent was removed in vacuo and after adding water (50 mL), the product was extracted with ethyl acetate (3×50 mL). The combined organic layers were washed with brine (50 mL), dried over sodium sulfate and concentrated to give the desired product (7.5 g, 100%). LCMS calculated for $C_{11}H_{15}BrN_5O_4$ (M+H)$^+$: m/z=359.9, 361.9.

Step 4: 4-[(4-Bromo-2-furyl)methyl]-3-{4-[(2-methoxyethyl)amino]-1,2,5-oxadiazol-3-yl}-1,2,4-oxadiazol-5(4H)-one

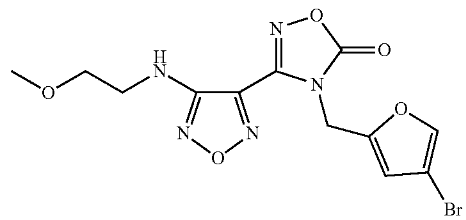 [SMILES: COCCNc1nonc1-c1noc(=O)n1Cc1cc(Br)co1]

N-[(4-Bromo-2-furyl)methyl]-N'-hydroxy-4-[(2-methoxyethyl)amino]-1,2,5-oxadiazole-3-carboximidamide (7.3 g, 20.4 mmol) and 1,1'-carbonyldiimidazole (5.0 g, 30.5 mmol) were dissolved in ethyl acetate (72 mL). The reaction mixture was heated at 65° C. for 15 minutes. Ethyl acetate (70 mL) was added and the crude reaction was washed with 0.1 N hydrogen chloride in water (2×70 mL). The organic layer was dried over sodium sulfate and concentrated in vacuo. Purification by flash chromatography on silica gel with an eluent of ethyl acetate in hexanes gave the desired product (4.1 g, 90%). LCMS calculated for $C_{12}H_{13}BrN_5O_5$ (M+H)$^+$: m/z=386.0, 388.0. $^1H$ NMR (400 MHz, $CD_3OD$): δ 7.88 (s, 1H), 6.67 (s, 1H), 6.39 (t, J=5.7 Hz, 1H), 5.07 (s, 2H), 3.50 (m, 2H), 3.41 (q, J=5.7 Hz, 2H), 3.25 (s, 3H).

Step 5: 4-[(4-Bromo-2-furyl)methyl]-3-{4-[(2-hydroxyethyl)amino]-1,2,5-oxadiazol-3-yl}-1,2,4-oxadiazol-5(4H)-one

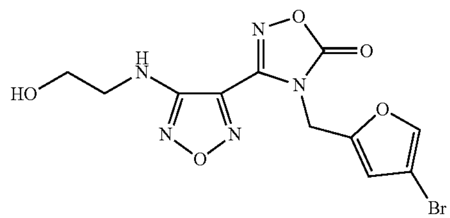 [SMILES: O=c1onc(-c2nonc2NCCO)n1Cc1cc(Br)co1]

In a round bottom flask under nitrogen atmosphere, 4-[(4-bromo-2-furyl)methyl]-3-{4-[(2-methoxyethyl)amino]-1,2,5-oxadiazol-3-yl}-1,2,4-oxadiazol-5(4H)-one (8.2 g, 21 mmol) was stirred in dichloromethane (68 mL). The temperature was brought to −78° C. and a solution of 1.0 M boron tribromide in dichloromethane (43 mL, 43 mmol) was added dropwise over 45 minutes. The reaction stirred at −78° C. for 45 minutes and continued to stir at 0° C. for an additional 30 minutes. While remaining at 0° C., a saturated solution of sodium bicarbonate in water (120 mL) was added dropwise over 25 minutes. After warming to room temperature, the organic layer was collected and the aqueous layer was extracted with ethyl acetate (2×50 mL). The combined organic layers were washed with brine (100 mL), dried over sodium sulfate and concentrated in vacuo to give the desired product (7.7 g, 97%) along with a small amount of 3-{4-[(2-bromoethyl)amino]-1,2,5-oxadiazol-3-yl}-4-[(4-bromo-2-furyl)methyl]-1,2,4-oxadiazol-5(4H)-one. LCMS calculated for $C_{11}H_{11}BrN_5O_5$ (M+H)$^+$: m/z=371.7, 374.0. $^1H$ NMR (400 MHz, DMSO-$d_6$): δ 7.89 (s, 1H), 6.68 (s, 1H), 6.31 (t, J=5.8 Hz, 1H), 5.08 (s, 2H), 4.85 (br s, 1H), 3.56 (m, 2H), 3.30 (q, J=5.6 Hz, 2H).

Step 6: 2-[(4-{4-[(4-Bromo-2-furyl)methyl]-5-oxo-4,5-dihydro-1,2,4-oxadiazol-3-yl}-1,2,5-oxadiazol-3-yl)amino]ethyl methanesulfonate

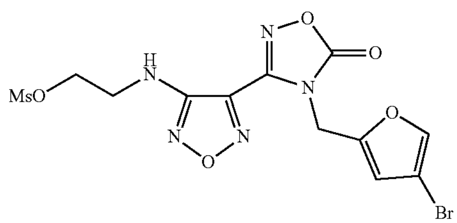 [SMILES: CS(=O)(=O)OCCNc1nonc1-c1noc(=O)n1Cc1cc(Br)co1]

To a solution of 4-[(4-bromo-2-furyl)methyl]-3-{4-[(2-hydroxyethyl)amino]-1,2,5-oxadiazol-3-yl}-1,2,4-oxadiazol-5(4H)-one (7.7 g, 21 mmol, containing also some of the corresponding bromo-compound) in ethyl acetate (100 mL) was added methanesulfonyl chloride (0.96 mL, 12 mmol) in one portion. The reaction was stirred for 5 minutes and triethylamine (1.6 mL, 11 mmol) was added, also in one portion. After stirring for 30 minutes, additional methanesulfonyl chloride (0.4 mL, 5 mmol) was added, followed 5 minutes later by triethylamine (0.58 mL, 4.2 mmol). After 15 minutes, the reaction was quenched with the addition of water (100 mL). The product was extracted with ethyl acetate (3×50 mL) and the combined organic layers washed with brine (100 mL). After drying over sodium sulfate, the solvent was removed in vacuo to give the desired product (9.3 g, 100%). LCMS calculated for $C_{12}H_{13}BrN_5O_7S$ $(M+H)^+$: m/z=449.8, 451.8. $^1H$ NMR (300 MHz, DMSO-$d_6$): δ 7.88 (s, 1H), 6.73 (t, J=6.2 Hz, 1H), 6.68 (s, 1H), 5.08 (s, 2H), 4.37 (m, 2H), 3.59 (q, J=5.8 Hz, 2H), 3.16 (s, 3H).

Step 7: 3-{4-[(2-Azidoethyl)amino]-1,2,5-oxadiazol-3-yl}-4-[(4-bromo-2-furyl)methyl]-1,2,4-oxadiazol-5(4H)-one

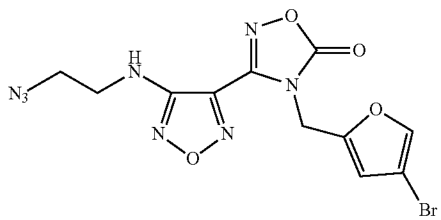 [SMILES: [N-]=[N+]=NCCNc1nonc1-c1noc(=O)n1Cc1cc(Br)co1]

2-[(4-{4-[(4-Bromo-2-furyl)methyl]-5-oxo-4,5-dihydro-1,2,4-oxadiazol-3-yl}-1,2,5-oxadiazol-3-yl)amino]ethyl methanesulfonate (9.1 g, 20 mmol, containing also some of the corresponding bromo-compound) was dissolved in dimethylformamide (90 mL). Sodium azide (1.97 g, 30.3 mmol) was added in one portion and after 5 minutes, the temperature was brought to 65° C. The reaction stirred for 2 hours and was allowed to cool back to room temperature. Water (200 mL) was added to quench the reaction. The product was extracted with ethyl acetate (3×100 mL) and the combined organic layers were washed with brine (2×150 mL) and water (150 mL). After drying over sodium sulfate, the solvent was removed in vacuo to give the desired product (7.7 g, 96%). LCMS calculated for $C_{11}H_9BrN_8NaO_4$ $(M+Na)^+$: m/z=418.7, 421.0. $^1H$ NMR (400 MHz, DMSO-$d_6$): δ 7.88 (s, 1H), 6.71 (t, J=5.7 Hz, 1H), 6.68 (s, 1H), 5.08 (s, 2H), 3.54 (t, J 5.7 Hz, 2H), 3.47 (q, J=5.7 Hz, 2H).

Step 8: 3-{4-[(2-Aminoethyl)amino]-1,2,5-oxadiazol-3-yl}-4-[(4-bromo-2-furyl)methyl]-1,2,4-oxadiazol-5(4H)-one hydroiodide

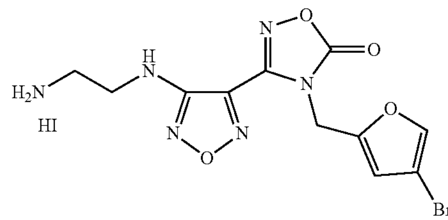

To a solution of 3-{4-[(2-azidoethyl)amino]-1,2,5-oxadiazol-3-yl}-4-[(4-bromo-2-furyl)methyl]-1,2,4-oxadiazol-5(4H)-one (7.7 g, 19 mmol) in methanol (80 mL) was added sodium iodide (17.4 g, 116 mmol). After stirring for 10 minutes, a solution of chlorotrimethylsilane (14.8 mL, 116 mmol) was added dropwise over 5 minutes. The reaction continued to stir for 1 hour, at which time it was slowly added to a solution of sodium thiosulfate (23.0 g, 145 mmol) in water (800 mL) at 0° C., resulting in a precipitate. The flask was rinsed with methanol (10 mL) and the precipitate was collected through vacuum filtration. The solid was rinsed with cold water (2×25 mL) and was dried under vacuum to give the desired product (5.8 g, 60%) as the hydroiodide salt. LCMS calculated for $C_{11}H_{12}BrN_6O_4$ $(M+H)^+$: m/z=370.9, 372.8. $^1H$ NMR (400 MHz, DMSO-$d_6$): δ 7.86 (s, 1H), 7.36 (br s, 3H), 6.68 (t, J=5.8 Hz, 1H), 6.65 (s, 1H), 5.07 (s, 2H), 3.45 (q, J=5.8 Hz, 2H), 2.98 (t, J=5.8 Hz, 2H).

Step 9: 4-({2-[(Aminosulfonyl)amino]ethyl}amino)-N-[(4-bromo-2-furyl)methyl]-N'-hydroxy-1,2,5-oxadiazole-3-carboximidamide

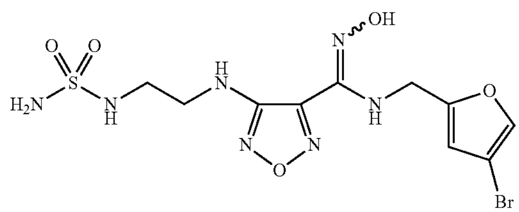 [SMILES: NS(=O)(=O)NCCNc1nonc1C(=NO)NCc1cc(Br)co1]

In a microwave vial, 3-{4-[(2-aminoethyl)amino]-1,2,5-oxadiazol-3-yl}-4-[(4-bromo-2-furyl)methyl]-1,2,4-oxadiazol-5(4H)-one hydroiodide (30 mg, 0.060 mmol) and sulfamide (29 mg, 0.30 mmol) were suspended in pyridine (1 mL). The reaction mixture was flushed with nitrogen and heated at 130° C. for 3 minutes in a microwave reactor. The solvent was removed and the crude intermediate was suspended in methanol (1 mL). A 2.0 N solution of NaOH in water (0.30 mL, 0.60 mmol) was added in one portion and the reaction was heated to 45° C. for 30 minutes. After neutralization with acetic acid (68 μL, 1.2 mmol), the product was purified by preparative LCMS to give the desired product (10.4 mg, 41%). LCMS calculated for $C_{10}H_{15}BrN_7O_5S$ $(M+H)^+$: m/z=423.9, 426.0. $^1H$ NMR (400 MHz, DMSO-$d_6$): δ 10.87 (s, 1H), 7.75 (s, 1H), 6.83 (t, J=7.3 Hz, 1H), 6.68 (t, J=6.0 Hz, 1H), 6.56 (s, 2H), 6.30 (t, J=6.0 Hz, 1H), 6.23 (s, 1H), 4.56 (d, J=7.0 Hz, 2H), 3.32 (q, J=6.3 Hz, 2H), 3.07 (q, J 6.3 Hz, 2H).

Example 21

4-({2-[(Aminosulfonyl)amino]ethyl}amino)-N-[(4-chloro-2-furyl)methyl]-N'-hydroxy-1,2,5-oxadiazole-3-carboximidamide

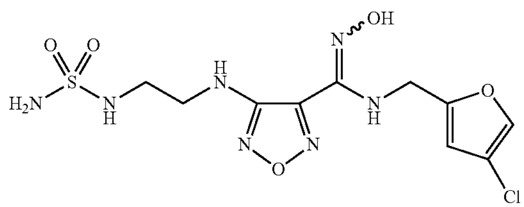 [SMILES: NS(=O)(=O)NCCNc1nonc1C(=NO)NCc1cc(Cl)co1]

Step 1: 4-Chloro-2-furaldehyde

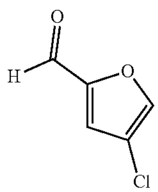

To a stirred suspension of aluminum trichloride (29.8 g, 0.223 mol) in dichloromethane (200 mL) under nitrogen atmosphere was added 2-furancarboxaldehyde (8.44 mL, 0.102 mol) over 15 minutes. After stirring for 30 minutes, chlorine was bubbled into the suspension using a pipette over a time period of 50 minutes. The flask was sealed and left to stir at room temperature for 90 hours. The reaction mixture was slowly added to a mixture of ice (500 mL) in a solution of 1.0 N hydrogen chloride in water (300 mL). The mixture was left to warm to room temperature over the next hour. The layers were separated and the organic layer collected. Additional product was extracted with dichloromethane (2×200 mL). The combined organic layers were washed with water (250 mL) and dried over sodium sulfate. The solvent was removed in vacuo to give a crude mixture containing the desired product (14.0 g, 100%, 60% purity). $^1H$ NMR (400 MHz, DMSO-$d_6$): δ 9.56 (s, 1H), 8.36 (s, 1H), 7.71 (s, 1H).

Step 2: tert-Butyl [(4-chloro-2-furyl)methyl]carbamate

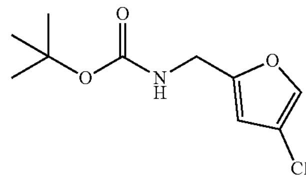

4-Chloro-2-furaldehyde (14.0 g, 60% purity, 64 mmol) was dissolved in ethanol (50 mL) and water (50 mL). N-Hydroxyamine hydrochloride (12.6 g, 182 mmol) and sodium acetate (14.9 g, 182 mmol) were added sequentially and the reaction mixture was brought to reflux at 100° C. for 1 hour. The solution was partially concentrated then water (25 mL) and ethyl acetate (50 mL) were added. The organic layer was collected and the aqueous was extracted with ethyl acetate (2×25 mL). The combined organic layers were washed with brine (50 mL) and water (50 mL). After drying over sodium sulfate, the solution was concentrated in vacuo. The intermediate was suspended in acetic acid (115 mL). The solution was cooled in an ice-bath and zinc (33.1 g, 506 mmol) was added portion-wise over 20 minutes. The reaction warmed to room temperature over 2 hours and was filtered through Celite. The solvent was removed in vacuo.

The residue was stirred in tetrahydrofuran (100 mL). A solution of 2.0 M NaOH in water (152 mL, 304 mmol) was added dropwise over 30 minutes. The reaction mixture was placed in an ice-bath and after 5 minutes, di-tert-butyldicarbonate (24.3 g, 111 mmol) was added dropwise over 15 minutes. The reaction was allowed to warm to room temperature over the next 2 hours and the tetrahydrofuran was then removed in vacuo. Ethyl acetate (100 mL) was added and the suspension was filtered. The organic layer was collected and the aqueous layer extracted with ethyl acetate (2×100 mL). The combined organic layers were washed with a 1:1 mixture of water/brine (100 mL), dried over sodium sulfate and concentrated in vacuo. Purification by flash chromatography on silica gel with an eluent of ethyl acetate in hexanes gave the desired product (3.05 g, 22%). LCMS calculated for $C_{10}H_{14}ClNNaO_3$ $(M+Na)^+$: m/z=253.9. $^1H$ NMR (400 MHz, DMSO-$d_6$): δ 7.81 (s, 1H), 7.37 (t, J=5.3 Hz, 1H), 6.32 (s, 1H), 4.05 (d, J=6.0 Hz, 2H), 1.36 (s, 9H).

Step 3: 1-(4-Chloro-2-furyl)methanamine trifluoroacetate

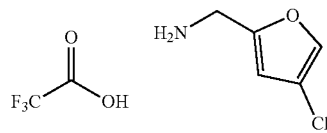 [SMILES: O=C(O)C(F)(F)F ; NCc1cc(Cl)co1]

The desired compound was prepared according to the procedure of Example 24, step 2, using tert-butyl [(4-chloro-2-furyl)methyl]carbamate as the starting material in quantitative yield. LCMS calculated for $C_5H_4C_{10}$ $(M-NH_2)^+$: m/z=115.0. $^1H$ NMR (400 MHz, DMSO-$d_6$): δ 8.29 (br s, 3H), 8.04 (s, 1H), 6.69 (s, 1H), 4.07 (s, 2H).

Step 4: N-[(4-Chloro-2-furyl)methyl]-N'-hydroxy-4-[(2-methoxyethyl)amino]-1,2,5-oxadiazole-3-carboximidamide

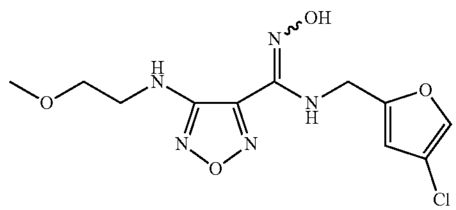 [SMILES: COCCNc1nonc1C(=NO)NCc1cc(Cl)co1]

The desired compound was prepared according to the procedure of Example 24, step 3, using N-hydroxy-4-(2-methoxyethylamino)-1,2,5-oxadiazole-3-carbimidoyl chloride and 1-(4-chloro-2-furyl)methanamine trifluoroacetate as the starting material in quantitative yield. LCMS calculated for $C_{11}H_{15}ClN_5O_4$ $(M+H)^+$: m/z=316.0.

Step 5: 4-[(4-Chloro-2-furyl)methyl]-3-{4-[(2-methoxyethyl)amino]-1,2,5-oxadiazol-3-yl}-1,2,4-oxadiazol-5(4H)-one

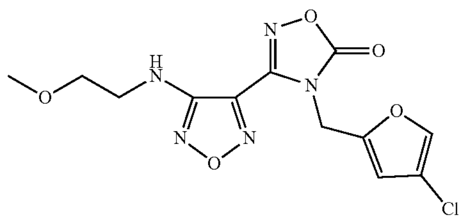 [SMILES: COCCNc1nonc1-c1noc(=O)n1Cc1cc(Cl)co1]

The desired compound was prepared according to the procedure of Example 24, step 4, using N-[(4-chloro-2-furyl)methyl]-N'-hydroxy-4-[(2-methoxyethyl)amino]-1,2,5-oxadiazole-3-carboximidamide as the starting material in 51% yield. LCMS calculated for $C_{12}H_{13}C_1N_5O_5$ $(M+H)^+$: m/z=342.0.

Step 6: 4-[(4-Chloro-2-furyl)methyl]-3-{4-[(2-hydroxyethyl)amino]-1,2,5-oxadiazol-3-yl}-1,2,4-oxadiazol-5(4H)-one

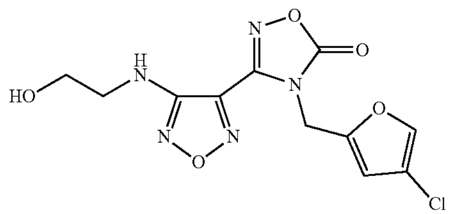 [SMILES: O=c1onc(-c2nonc2NCCO)n1Cc1cc(Cl)co1]

The desired compound was prepared according to the procedure of Example 24, step 5, using 4-[(4-chloro-2-furyl)methyl]-3-{4-[(2-methoxyethyl)amino]-1,2,5-oxadiazol-3-yl}-1,2,4-oxadiazol-5(4H)-one as the starting material in quantitative yield. LCMS calculated for $C_{11}H_{10}ClN_5NaO_5$ $(M+Na)^+$: m/z=349.9.

Step 7: 2-[(4-{4-[(4-Chloro-2-furyl)methyl]-5-oxo-4,5-dihydro-1,2,4-oxadiazol-3-yl}-1,2,5-oxadiazol-3-yl)amino]ethyl methanesulfonate

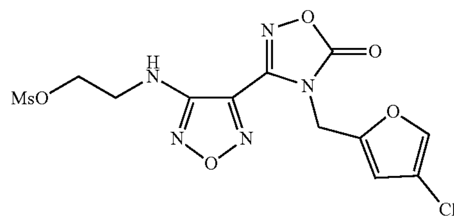 [SMILES: CS(=O)(=O)OCCNc1nonc1-c1noc(=O)n1Cc1cc(Cl)co1]

The desired compound was prepared according to the procedure of Example 24, step 6, using 4-[(4-chloro-2-furyl)methyl]-3-{4-[(2-hydroxyethyl)amino]-1,2,5-oxadiazol-3-yl}-1,2,4-oxadiazol-5(4H)-one as the starting material in 69% yield. LCMS calculated for $C_{12}H_{13}ClN_5O_7S$ $(M+H)^+$: m/z=405.8.

Step 8: 3-{4-[(2-Azidoethyl)amino]-1,2,5-oxadiazol-3-yl}-4-[(4-chloro-2-furyl)methyl]-1,2,4-oxadiazol-5(4H)-one

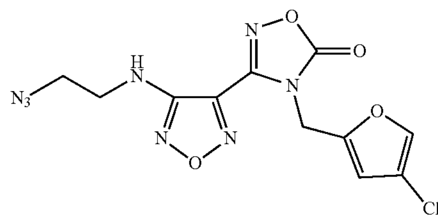 [SMILES: [N-]=[N+]=NCCNc1nonc1-c1noc(=O)n1Cc1cc(Cl)co1]

The desired compound was prepared according to the procedure of Example 24, step 7, using 2-[(4-{4-[(4-chloro-2-furyl)methyl]-5-oxo-4,5-dihydro-1,2,4-oxadiazol-3-yl}-1,2,5-oxadiazol-3-yl)amino]ethyl methanesulfonate as the starting material in quantitative yield. LCMS calculated for $C_{11}H_9ClN_8NaO_4$ $(M+Na)^+$: m/z=374.9.

Step 9: 3-{4-[(2-Aminoethyl)amino]-1,2,5-oxadiazol-3-yl}-4-[(4-chloro-2-furyl)methyl]-1,2,4-oxadiazol-5(4H)-one hydroiodide

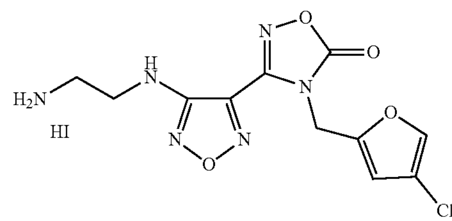

The desired compound was prepared according to the procedure of Example 24, step 8, using 3-{4-[(2-azidoethyl)amino]-1,2,5-oxadiazol-3-yl}-4-[(4-chloro-2-furyl)methyl]-1,2,4-oxadiazol-5(4H)-one as the starting material in 57% yield. LCMS calculated for $C_{11}H_{12}ClN_6O_4$ $(M+H)^+$: m/z=326.9.

Step 10: 4-({2-[(Aminosulfonyl)amino] ethyl}amino)-N-[(4-chloro-2-furyl)methyl]-N'-hydroxy-1,2,5-oxadiazole-3-carboximidamide

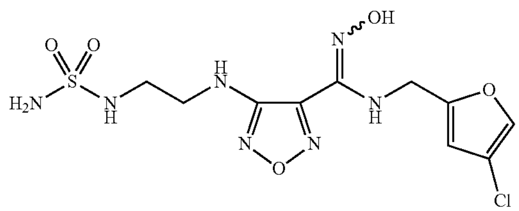 [SMILES: NS(=O)(=O)NCCNc1nonc1C(=NO)NCc1cc(Cl)co1]

The desired compound was prepared according to the procedure of Example 24, step 9, using 3-{4-[(2-aminoethyl)amino]-1,2,5-oxadiazol-3-yl}-4-[(4-chloro-2-furyl)methyl]-1,2,4-oxadiazol-5(4H)-one hydroiodide as the starting material in 53% yield. LCMS calculated for $C_{10}H_{15}ClN_7O_5S$ $(M+H)^+$: m/z=379.9. $^1H$ NMR (400 MHz, DMSO-$d_6$): δ 10.88 (s, 1H), 7.77 (s, 1H), 6.83 (t, J 6.8 Hz, 1H), 6.68 (t, J=5.9 Hz, 1H), 6.56 (s, 2H), 6.30 (t, J=5.9 Hz, 1H), 6.22 (s, 1H), 4.55 (d, 2H), 3.32 (q, J=6.3 Hz, 2H), 3.06 (q, J=6.3 Hz, 2H).

Example 22

Alternate Preparation of the Intermediate 3-(4-(2-aminoethylamino)-1,2,5-oxadiazol-3-yl)-4-(3-bromo-4-fluorophenyl)-1,2,4-oxadiazol-5(4H)-one hydroiodide

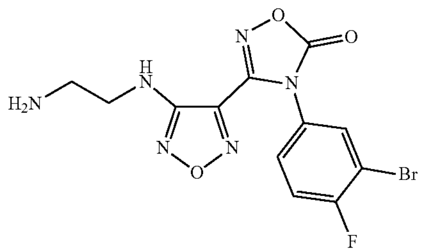 [SMILES: NCCNc1nonc1-c1noc(=O)n1-c1ccc(F)c(Br)c1]

Step 1: 4-Amino-N'-hydroxy-N-(2-methoxyethyl)-1,2,5-oxadiazole-3-carboximidamide

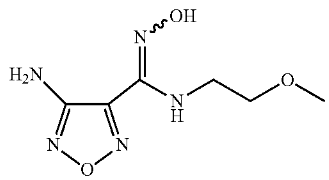

4-Amino-N-hydroxy-1,2,5-oxadiazole-3-carboximidoyl chloride (can be prepared according to Example 5, steps 1-2, 200.0 g, 1.23 mol) was mixed with ethyl acetate (1.2 L). At 0-5° C. 2-methoxyethylamine [Aldrich, product #143693] (119.0 mL, 1.35 mol) was added in one portion while stirring. The reaction temperature rose to 41° C. The reaction was cooled to 0-5° C. Triethylamine (258 mL, 1.84 mol) was added. After stirring 5 min, LCMS indicated reaction completion. The reaction solution was washed with water (500 mL) and brine (500 mL), dried over sodium sulfate, and concentrated to give the desired product (294 g, 119%) as a crude dark oil. LCMS for $C_6H_{12}N_5O_3$ $(M+H)^+$: m/z=202.3. $^1H$ NMR (400 MHz, DMSO-$d_6$): δ 10.65 (s, 1H), 6.27 (s, 2H), 6.10 (t, J=6.5 Hz, 1H), 3.50 (m, 2H), 3.35 (d, J=5.8 Hz, 2H), 3.08 (s, 3H).

Step 2: N'-Hydroxy-4-[(2-methoxyethyl)amino]-1,2,5-oxadiazole-3-carboximidamide

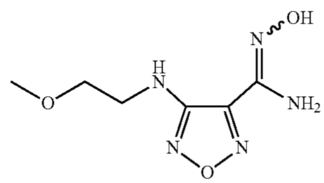

4-Amino-N'-hydroxy-N-(2-methoxyethyl)-1,2,5-oxadiazole-3-carboximidamide (248.0 g, 1.23 mol) was mixed with water (1 L). Potassium hydroxide (210 g, 3.7 mol) was added. The reaction was refluxed at 100° C. overnight (15 hours). TLC with 50% ethyl acetate (containing 1% ammonium hydroxide) in hexane indicated reaction completed (product Rf=0.6, starting material Rf=0.5). LCMS also indicated reaction completion. The reaction was cooled to room temperature and extracted with ethyl acetate (3×1 L). The combined ethyl acetate solution was dried over sodium sulfate and concentrated to give the desired product (201 g, 81%) as a crude off-white solid. LCMS for $C_6H_{12}N_5O_3$ $(M+H)^+$: m/z=202.3 $^1H$ NMR (400 MHz, DMSO-$d_6$): δ 10.54 (s, 1H), 6.22 (s, 2H), 6.15 (t, J=5.8 Hz, 1H), 3.45 (t, J=5.3 Hz, 2H), 3.35 (m, 2H), 3.22 (s, 3H).

Step 3: N-Hydroxy-4-[(2-methoxyethyl)amino]-1,2,5-oxadiazole-3-carboximidoyl chloride

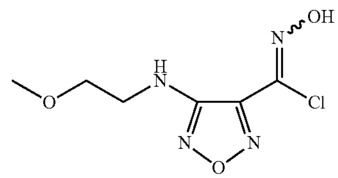

At room temperature N'-hydroxy-4-[(2-methoxyethyl)amino]-1,2,5-oxadiazole-3-carboximidamide (50.0 g, 0.226 mol) was dissolved in 6.0 M hydrochloric acid aqueous solution (250 mL, 1.5 mol). Sodium chloride (39.5 g, 0.676 mol) was added followed by water (250 mL) and ethyl acetate (250 mL). At 3-5° C. a previously prepared aqueous solution (100 mL) of sodium nitrite (15.0 g, 0.217 mol) was added slowly over 1 hr. The reaction was stirred at 3-8° C. for 2 hours and then room temperature over the weekend. LCMS indicated reaction completed. The reaction solution was extracted with ethyl acetate (2×200 mL). The combined ethyl acetate solution was dried over sodium sulfate and concentrated to give the desired product (49.9 g, 126%) as a crude white solid. LCMS for $C_6H_{10}ClN_4O_3$ $(M+H)^+$: m/z=221.0. $^1H$ NMR (400 MHz, DMSO-$d_6$): δ 13.43 (s, 1H), 5.85 (t, J=5.6 Hz, 1H), 3.50 (t, J=5.6 Hz, 2H), 3.37 (dd, J=10.8, 5.6 Hz, 2H), 3.25 (s, 3H).

Step 4: N-(3-Bromo-4-fluorophenyl)-N'-hydroxy-4-[(2-methoxyethyl)amino]-1,2,5-oxadiazole-3-carboximidamide

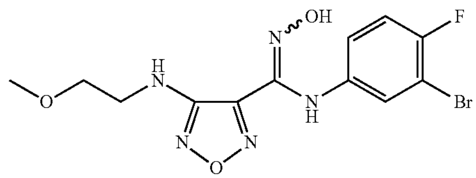 [SMILES: COCCNc1nonc1C(=NO)Nc1ccc(F)c(Br)c1]

N-Hydroxy-4-[(2-methoxyethyl)amino]-1,2,5-oxadiazole-3-carboximidoyl chloride (46.0 g, 0.208 mol) was mixed with water (300 mL). The mixture was heated to 60° C. 3-Bromo-4-fluoroaniline [Oakwood products, product #013091] (43.6 g, 0.229 mol) was added and stirred for 10 min. A warm sodium bicarbonate (26.3 g, 0.313 mol) solution (300 mL water) was added over 15 min. The reaction was stirred at 60° C. for 20 min. LCMS indicated reaction completion. The reaction solution was cooled to room temperature and extracted with ethyl acetate (2×300 mL). The combined ethyl acetate solution was dried over sodium sulfate and concentrated to give the desired product (76.7 g, 98%) as a crude brown solid. LCMS for $C_{12}H_{14}BrFN_5O_3$ $(M+H)^+$: m/z=374.0, 376.0. $^1$H NMR (400 MHz, DMSO-$d_6$): δ 11.55 (s, 1H), 8.85 (s, 1H), 7.16 (t, J=8.8 Hz, 1H), 7.08 (dd, J=6.1, 2.7 Hz, 1H), 6.75 (m, 1H), 6.14 (t, J=5.8 Hz, 1H), 3.48 (t, J=5.2 Hz, 2H), 3.35 (dd, J=10.8, 5.6 Hz, 2H), 3.22 (s, 3H).

Step 5: 4-(3-Bromo-4-fluorophenyl)-3-{4-[(2-methoxyethyl)amino]-1,2,5-oxadiazol-3-yl}-1,2,4-oxadiazol-5(4H)-one

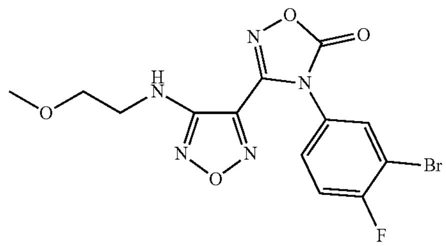 [SMILES: COCCNc1nonc1-c1noc(=O)n1-c1ccc(F)c(Br)c1]

A mixture of N-(3-bromo-4-fluorophenyl)-N'-hydroxy-4-[(2-methoxyethyl)amino]-1,2,5-oxadiazole-3-carboximidamide (76.5 g, 0.204 mol), 1,1'-carbonyldiimidazole (49.7 g, 0.307 mol), and ethyl acetate (720 mL) was heated to 60° C. and stirred for 20 min. LCMS indicated reaction completed. The reaction was cooled to room temperature, washed with 1 N HCl (2×750 mL), dried over sodium sulfate, and concentrated to give the desired product (80.4 g, 98%) as a crude brown solid. LCMS for $C_{13}H_{12}BrFN_5O_4$ $(M+H)^+$: m/z=400.0, 402.0. $^1$H NMR (400 MHz, DMSO-$d_6$): δ 7.94 (t, J=8.2 Hz, 1H), 7.72 (dd, J=9.1, 2.3 Hz, 1H), 7.42 (m, 1H), 6.42 (t, J=5.7 Hz, 1H), 3.46 (t, J=5.4 Hz, 2H), 3.36 (t, J=5.8 Hz, 2H), 3.26 (s, 3H).

Step 6: 4-(3-Bromo-4-fluorophenyl)-3-{4-[(2-hydroxyethyl)amino]-1,2,5-oxadiazol-3-yl}-1,2,4-oxadiazol-5(4H)-one

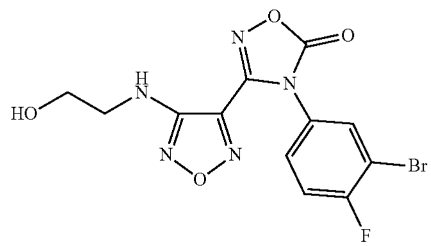 [SMILES: O=c1onc(-c2nonc2NCCO)n1-c1ccc(F)c(Br)c1]

4-(3-Bromo-4-fluorophenyl)-3-{4-[(2-methoxyethyl)amino]-1,2,5-oxadiazol-3-yl}-1,2,4-oxadiazol-5(4H)-one (78.4 g, 0.196 mol) was dissolved in dichloromethane (600 mL). At −67° C. boron tribromide (37 mL, 0.392 mol) was added over 15 min. The reaction was warmed up to −10° C. in 30 min. LCMS indicated reaction completed. The reaction was stirred at room temperature for 1 hour. At 0-5° C. the reaction was slowly quenched with saturated sodium bicarbonate solution (1.5 L) over 30 min. The reaction temperature rose to 25° C. The reaction was extracted with ethyl acetate (2×500 mL, first extraction organic layer is on the bottom and second extraction organic lager is on the top). The combined organic layers were dried over sodium sulfate and concentrated to give the desired product (75 g, 99%) as a crude brown solid. LCMS for $C_{12}H_{10}BrFN_5O_4$ $(M+H)^+$: m/z=386.0, 388.0. $^1$H NMR (400 MHz, DMSO-$d_6$): δ 8.08 (dd, J=6.2, 2.5 Hz, 1H), 7.70 (m, 1H), 7.68 (t, J=8.7 Hz, 1H), 6.33 (t, J=5.6 Hz, 1H), 4.85 (t, J=5.0 Hz, 1H), 3.56 (dd, J=10.6, 5.6 Hz, 2H), 3.29 (dd, J=11.5, 5.9 Hz, 2H).

Step 7: 2-({4-[4-(3-Bromo-4-fluorophenyl)-5-oxo-4,5-dihydro-1,2,4-oxadiazol-3-yl]-1,2,5-oxadiazol-3-yl}amino)ethyl methanesulfonate

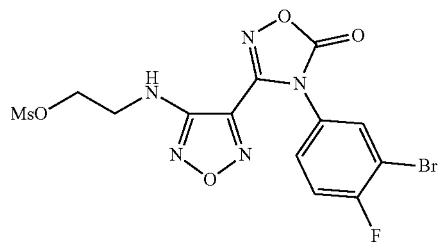 [SMILES: CS(=O)(=O)OCCNc1nonc1-c1noc(=O)n1-c1ccc(F)c(Br)c1]

4-(3-bromo-4-fluorophenyl)-3-(4-(2-hydroxyethylamino)-1,2,5-oxadiazol-3-yl)-1,2,4-oxadiazol-5(4H)-one (72.2 g, 0.188 mol) was mixed with ethyl acetate (600 mL). Methanesulfonyl chloride (19.2 mL, 0.248 mol) was added followed by triethylamine (34.9 mL, 0.250 mol). The reaction was stirred at room temperature for 5 min. When LCMS indicated completion of reaction (M+H=442), 500 mL of water was added into reaction. The reaction was extracted with ethyl acetate (2×500 mL). The combined ethyl acetate solution was washed with brine (500 mL), dried over sodium sulfate and concentrated to give 85.1 g crude brown solid. $^1$H NMR verified the structure. Crude yield was 97%. LCMS for $C_{13}H_{11}BrFN_5O_6SNa$ $(M+Na)^+$: m/z=485.9, 487.9. $^1$H NMR (400 MHz, DMSO-$d_6$): δ 8.08 (dd, J=6.2, 2.5 Hz, 1H), 7.72 (m, 1H), 7.58 (t, J=8.7 Hz, 1H), 6.75 (t, J=5.9 Hz, 1H), 4.36 (t, J=5.3 Hz, 2H), 3.58 (dd, J=11.2, 5.6 Hz, 2H), 3.18 (s, 3H).

Step 8: 3-{4-[(2-Azidoethyl)amino]-1,2,5-oxadiazol-3-yl}-4-(3-bromo-4-fluorophenyl)-1,2,4-oxadiazol-5(4H)-one

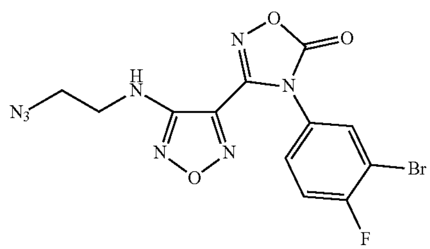 [SMILES: [N-]=[N+]=NCCNc1nonc1-c1noc(=O)n1-c1ccc(F)c(Br)c1]

2-(4-(4-(3-bromo-4-fluorophenyl)-5-oxo-4,5-dihydro-1,2,4-oxadiazol-3-yl)-1,2,5-oxadiazol-3-ylamino)ethyl methanesulfonate (50.0 g, 0.108 mol) was dissolved in N, N-dimethylformamide (83 mL). Sodium azide (10.5 g, 0.162 mol) was added. The reaction was stirred at 65° C. for 5-6 hours. LCMS indicated reaction completed (M+Na=435). The reaction was quenched with water (250 mL) and extracted with ethyl acetate (2×250 mL). The combined ethyl acetate solution was washed with water (250 mL, layer separation was slow, 100 mL of brine was added to improve the separation), dried over sodium sulfate, and concentrated to give 49.7 g crude brown solid. Crude yield is 112%. LCMS for $C_{12}H_8BrFN_8O_3Na$ $(M+Na)^+$: m/z=433.0, 435.0. $^1H$ NMR (400 MHz, DMSO-$d_6$): δ 8.08 (dd, J=6.2, 2.5 Hz, 1H), 7.72 (m, 1H), 7.58 (t, J=8.7 Hz, 1H), 6.75 (t, J=5.7 Hz, 1H), 3.54 (t, J=5.3 Hz, 2H), 3.45 (dd, J=11.1, 5.2 Hz, 2H).

Step 9: 3-(4-(2-aminoethylamino)-1,2,5-oxadiazol-3-yl)-4-(3-bromo-4-fluorophenyl)-1,2,4-oxadiazol-5(4H)-one hydroiodide

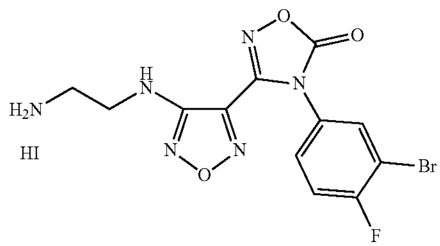

3-(4-(2-azidoethylamino)-1,2,5-oxadiazol-3-yl)-4-(3-bromo-4-fluorophenyl)-1,2,4-oxadiazol-5(4H)-one (80.0 g, 0.194 mol) was mixed with methanol (800 mL). Sodium iodide (175.0 g, 1.17 mol) was added. The reaction was stirred at room temperature for 10 min. Chlorotrimethylsilane (148 mL, 1.17 mol) was dissolved in methanol (100 mL) and added to the reaction over 30 min. The reaction temperature rose 42° C. The reaction was stirred at room temperature for 30 min. LCMS indicated reaction completed (M+H=386). The reaction was quenched with sodium thiosulfate (190.0 g, 1.20 mol) in water (900 mL). A large amount of solid precipitated. The product was collected by filtration (filtration speed was slow), rinsed with water (200 mL), and dried on vacuum overnight. The filter cake was slurried in ethyl acetate (500 mL) for 30 min. The product was filtered (filtration speed is slow) and dried under vacuum over weekend to give 95 g of an off-white solid. LCMS for $C_{12}H_{11}BrFN_6O_3$ $(M+H)^+$: m/z=384.9, 386.9. $^1H$ NMR (400 MHz, DMSO-$d_6$): δ 8.12 (m, 4H), 7.76 (m, 1H), 7.58 (t, J=8.7 Hz, 1H), 6.78 (t, J=6.1 Hz, 1H), 3.51 (dd, J=11.8, 6.1 Hz, 2H), 3.02 (m, 2H).

Example 23

Alternate preparation of 4-({2-[(Aminosulfonyl)amino]ethyl}amino)-N-(3-bromo-4-fluorophenyl)-N'-hydroxy-1,2,5-oxadiazole-3-carboximidamide

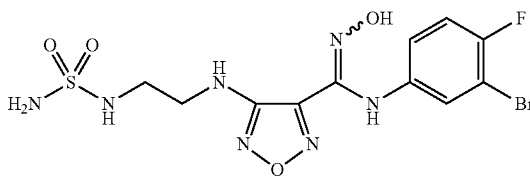

Step 1: 4-(3-bromo-4-fluorophenyl)-3-(4-(2-hydroxyethylamino)-1,2,5-oxadiazol-3-yl)-1,2,4-oxadiazol-5(4H)-one

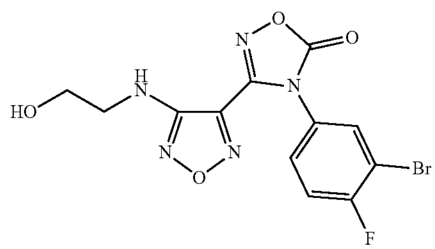 [SMILES: O=c1onc(-c2nonc2NCCO)n1-c1ccc(F)c(Br)c1]

To a solution of 4-(3-bromo-4-fluorophenyl)-3-(4-(2-methoxyethylamino)-1,2,5-oxadiazol-3-yl)-1,2,4-oxadiazol-5(4H)-one (can be prepared according to Example 5, steps 1-7; 1232 g, 3.08 mol) in dichloromethane (12 L) stirring in a 22 L flask at 0° C. was added boron tribromide (354 mL, 3.67 mL) dropwise at a rate so that the temperature did not exceed 10° C. After stirring on ice for 1 h, a solution of saturated aqueous sodium bicarbonate (2 L) was carefully added at a rate so that the temperature did not exceed 20° C. (addition time 10 min). The resulting mixture was transferred to a 50 L separatory funnel, diluted with water (10 L), and the pH of the aqueous layer adjusted from 1 to 8 using solid sodium bicarbonate. The layers were separated, and the organic layer was washed with water (10 L), and the solvents removed in vacuo to afford a tan solid (24 mol processed in multiple runs, 9.54 kg, quant. yield). The material was slurried in 4 volumes of 7:1 heptane:ethyl acetate (4×22 L flasks), filtered, and dried to furnish the title compound as a tan solid (8679 g, 94%). The product was a mixture of the hydroxy- and the corresponding bromo-species.

Step 2: 2-(4-(4-(3-bromo-4-fluorophenyl)-5-oxo-4,5-dihydro-1,2,4-oxadiazol-3-yl)-1,2,5-oxadiazol-3-ylamino)ethyl methanesulfonate

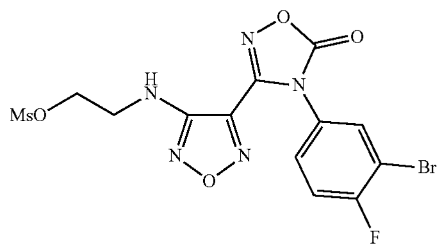 [SMILES: CS(=O)(=O)OCCNc1nonc1-c1noc(=O)n1-c1ccc(F)c(Br)c1]

To a solution of 4-(3-bromo-4-fluorophenyl)-3-{4-[(2-hydroxyethyl)amino]-1,2,5-oxadiazol-3-yl}-1,2,4-oxadiazol-5(4H)-one (1.5 kg, 3.9 mol, containing also some of the corresponding bromo-compound) in ethyl acetate (12 L) was added methanesulfonyl chloride (185 mL, 2.4 mol) dropwise over 1 h at room temperature. Triethylamine (325 mL, 2.3 mol) was added dropwise over 45 min, during which time the reaction temperature increased to 35° C. After 2 h, the reaction mixture was washed with water (5 L), brine (1 L), dried over sodium sulfate, combined with 3 more reactions of the same size, and the solvents removed in vacuo to afford the desired product (7600 g, quantitative yield, containing also some of the corresponding bromo-compound, Caution: irritating dust!) as a tan solid. LCMS for $C_{13}H_{11}BrFN_5O_6SNa$ $(M+Na)^+$: m/z=485.9, 487.9. $^1H$ NMR (400 MHz, DMSO-$d_6$): δ 8.08 (dd, J=6.2, 2.5 Hz, 1H), 7.72 (m, 1H), 7.58 (t, J=8.7 Hz, 1H), 6.75 (t, J=5.9 Hz, 1H), 4.36 (t, J=5.3 Hz, 2H), 3.58 (dd, J=11.2, 5.6 Hz, 2H), 3.18 (s, 3H).

Step 3: 3-(4-(2-azidoethylamino)-1,2,5-oxadiazol-3-yl)-4-(3-bromo-4-fluorophenyl)-1,2,4-oxadiazol-5(4H)-one

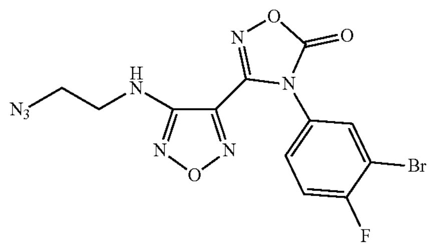 [SMILES: [N-]=[N+]=NCCNc1nonc1-c1noc(=O)n1-c1ccc(F)c(Br)c1]

To a solution of 2-({4-[4-(3-bromo-4-fluorophenyl)-5-oxo-4,5-dihydro-1,2,4-oxadiazol-3-yl]-1,2,5-oxadiazol-3-yl}amino)ethyl methanesulfonate (2.13 kg, 4.6 mol, containing also some of the corresponding bromo-compound) in dimethylformamide (4 L) stirring in a 22 L flask was added sodium azide (380 g, 5.84 mol). The reaction was heated at 50° C. for 6 h, poured into ice/water (8 L), and extracted with 1:1 ethyl acetate:heptane (20 L). The organic layer was washed with water (5 L) and brine (5 L), and the solvents removed in vacuo to afford the desired product (1464 g, 77%) as a tan solid. LCMS for $C_{12}H_8BrFN_8O_3Na$ $(M+Na)^+$: m/z=433.0, 435.0. $^1H$ NMR (DMSO-$d_6$, 400 MHz): δ 8.08 (dd, J=6.2, 2.5 Hz, 1H), 7.72 (m, 1H), 7.58 (t, J=8.7 Hz, 1H), 6.75 (t, J=5.7 Hz, 1H), 3.54 (t, J=5.3 Hz, 2H), 3.45 (dd, J=11.1, 5.2 Hz, 2H).

Step 4: 3-{4-[(2-Aminoethyl)amino]-1,2,5-oxadiazol-3-yl}-4-(3-bromo-4-fluorophenyl)-1,2,4-oxadiazol-5(4H)-one hydrochloride

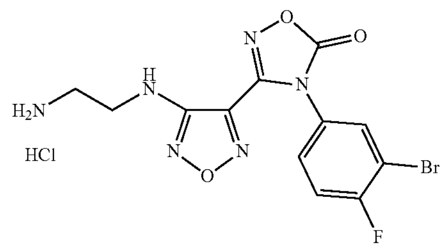 [SMILES: NCCNc1nonc1-c1noc(=O)n1-c1ccc(F)c(Br)c1 ; Cl]

Step 4, Part 1: tert-Butyl 2-(4-(4-(3-bromo-4-fluorophenyl)-5-oxo-4,5-dihydro-1,2,4-oxadiazol-3-yl)-1,2,5-oxadiazol-3-ylamino)ethylcarbamate

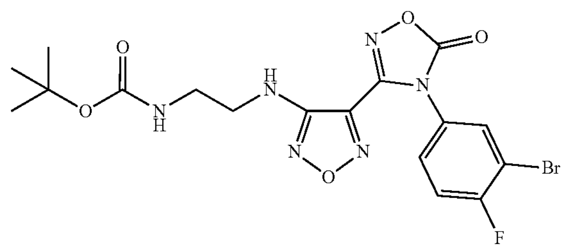 [SMILES: CC(C)(C)OC(=O)NCCNc1nonc1-c1noc(=O)n1-c1ccc(F)c(Br)c1]

Sodium iodide (1080 g, 7.2 mol) was added to 3-{4-[(2-azidoethyl)amino]-1,2,5-oxadiazol-3-yl}-4-(3-bromo-4-fluorophenyl)-1,2,4-oxadiazol-5(4H)-one (500 g, 1.22 mol) in methanol (6 L). The mixture was allowed to stir for 30 min during which time a mild exotherm was observed. Chlorotrimethylsilane (930 mL, 7.33 mol) was added as a solution in methanol (1 L) dropwise at a rate so that the temperature did not exceed 35° C., and the reaction was allowed to stir for 3.5 h at ambient temperature. The reaction was neutralized with 33 wt % solution of sodium thiosulfate pentahydrate in water (~1.5 L), diluted with water (4 L), and the pH adjusted to 9 carefully with solid potassium carbonate (250 g—added in small portions: watch foaming). Di-tert-butyl dicarbonate (318 g, 1.45 mol) was added and the reaction was allowed to stir at room temperature. Additional potassium carbonate (200 g) was added in 50 g portions over 4 h to ensure that the pH was still at or above 9. After stirring at room temperature overnight, the solid was filtered, triturated with water (2 L), and then MTBE (1.5 L). A total of 11 runs were performed (5.5 kg, 13.38 mol). The combined solids were triturated with 1:1 THF:dichloromethane (24 L, 4 runs in a 20 L rotary evaporator flask, 50° C., 1 h), filtered, and washed with dichloromethane (3 L each run) to afford an off-white solid. The crude material was dissolved at 55° C. tetrahydrofuran (5 mL/g), treated with decolorizing carbon (2 wt %) and silica gel (2 wt %), and filtered hot through celite to afford the product as an off-white solid (5122 g). The combined MTBE, THF, and dichloromethane filtrates were concentrated in vacuo and chromatographed (2 kg silica gel, heptane with a 0-100% ethyl acetate gradient, 30 L) to afford more product (262 g). The combined solids of tert-butyl 2-(4-(4-(3-bromo-4-fluorophenyl)-5-oxo-4,5-dihydro-1,2,4-oxadiazol-3-yl)-1,2,5-oxadiazol-3-ylamino) ethylcarbamate were dried to a constant weight in a convection oven (5385 g, 83%).

Step 5, Part 2: 3-{4-[(2-Aminoethyl)amino]-1,2,5-oxadiazol-3-yl}-4-(3-bromo-4-fluorophenyl)-1,2,4-oxadiazol-5(4H)-one hydrochloride

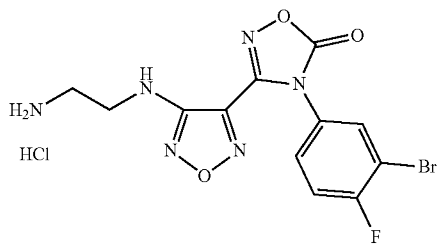 [SMILES: NCCNc1nonc1-c1noc(=O)n1-c1ccc(F)c(Br)c1 ; Cl]

Method A:

In a 22 L flask was charged hydrogen chloride (4 N solution in 1,4-dioxane, 4 L, 16 mol). tert-Butyl [2-({4-[4-(3-bromo-4-fluorophenyl)-5-oxo-4,5-dihydro-1,2,4-oxadiazol-3-yl]-1,2,5-oxadiazol-3-yl}amino)ethyl]carbamate (2315 g, 4.77 mol) was added as a solid in portions over 10 min. The slurry was stirred at room temperature and gradually became a thick paste that could not be stirred. After sitting overnight at room temperature, the paste was slurried in ethyl acetate (10 L), filtered, re-slurried in ethyl acetate (5 L), filtered, and dried to a constant weight to afford the desired product as a white solid (combined with other runs, 5 kg starting material charged, 4113 g, 95%). LCMS for $C_{12}H_{11}BrFN_6O_3$ $(M+H)^+$: m/z=384.9, 386.9. $^1$H NMR (400 MHz, DMSO-$d_6$): δ 8.12 (m, 4H), 7.76 (m, 1H), 7.58 (t, J=8.7 Hz, 1H), 6.78 (t, J=6.1 Hz, 1H), 3.51 (dd, J=11.8, 6.1 Hz, 2H), 3.02 (m, 2H).

Method B:

tert-Butyl [2-({4-[4-(3-bromo-4-fluorophenyl)-5-oxo-4,5-dihydro-1,2,4-oxadiazol-3-yl]-1,2,5-oxadiazol-3-yl}amino)ethyl]carbamate (5000 g) was added to a mixture of isopropanol (20 L) and 4 N HCl in 1,4-dioxane (10 L) at room temperature. The batch was heated to 40-45° C. and held for 1 h. Ethyl acetate was added to the batch at 40-45° C. and held for 2.5 h. Upon reaction completion, as indicated by HPLC, heptane (10 L) was added to the batch. The batch was cooled to 25° C. The product was isolated by filtration and the wet cake was washed with ethyl acetate (3×5.0 L). The product was dried in a vacuum, oven at 20° C. to give 4344 g (93.4% yield) of the title compound. LC-MS, $^1$H and $^{13}$C NMR, and HPLC data of this lot were identical to those of the product prepared by Method A.

Step 5: tert-Butyl ({[2-({4-[4-(3-bromo-4-fluorophenyl)-5-oxo-4,5-dihydro-1,2,4-oxadiazol-3-yl]-1,2,5-oxadiazol-3-yl}amino)ethyl]amino}sulfonyl) carbamate

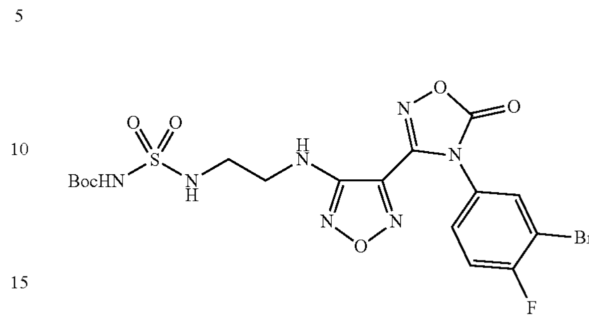

A 5 L round bottom flask was charged with chlorosulfonyl isocyanate [Aldrich, product #142662] (149 mL, 1.72 mol) and dichloromethane (1.5 L) and cooled using an ice bath to 2° C. tert-Butanol (162 mL, 1.73 mol) in dichloromethane (200 mL) was added dropwise at a rate so that the temperature did not exceed 10° C. The resulting solution was stirred at room temperature for 30-60 min to provide tert-butyl [chlorosulfonyl]carbamate.

A 22 L flask was charged with 3-{4-[(2-aminoethyl) amino]-1,2,5-oxadiazol-3-yl}-4-(3-bromo-4-fluorophenyl)-1,2,4-oxadiazol-5(4H)-one hydrochloride (661 g, 1.57 mol) and 8.5 L dichloromethane. After cooling to −15° C. with an ice/salt bath, the solution of tert-butyl [chlorosulfonyl]carbamate (prepared as above) was added at a rate so that the temperature did not exceed −10° C. (addition time 7 min). After stirring for 10 min, triethylamine (1085 mL, 7.78 mol) was added at a rate so that the temperature did not exceed −5° C. (addition time 10 min). The cold bath was removed, the reaction was allowed to warm to 10° C., split into two portions, and neutralized with 10% conc HCl (4.5 L each portion). Each portion was transferred to a 50 L separatory funnel and diluted with ethyl acetate to completely dissolve the white solid (~25 L). The layers were separated, and the organic layer was washed with water (5 L), brine (5 L), and the solvents removed in vacuo to afford an off-white solid. The solid was triturated with MTBE (2×1.5 L) and dried to a constant weight to afford a white solid. A total of 4113 g starting material was processed in this manner (5409 g, 98%). $^1$H NMR (400 MHz, DMSO-$d_6$): δ 10.90 (s, 1H), 8.08 (dd, J=6.2, 2.5 Hz, 1H), 7.72 (m, 1H), 7.59 (t, J=8.6 Hz, 1H), 6.58 (t, J=5.7 Hz, 1H), 3.38 (dd, J=12.7, 6.2 Hz, 2H), 3.10 (dd, J=12.1, 5.9 Hz, 2H), 1.41 (s, 9H).

Step 6: N-[2-({4-[4-(3-Bromo-4-fluorophenyl)-5-oxo-4,5-dihydro-1,2,4-oxadiazol-3-yl]-1,2,5-oxadiazol-3-yl}amino)ethyl]sulfamide

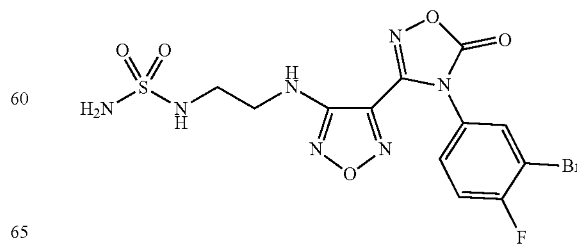

Method A: Using Trifluoroacetic Acid

To a 22 L flask containing 98:2 trifluoroacetic acid:water (8.9 L) was added tert-butyl ({[2-({4-[4-(3-bromo-4-fluorophenyl)-5-oxo-4,5-dihydro-1,2,4-oxadiazol-3-yl]-1,2,5-oxadiazol-3-yl}amino)ethyl]amino}sulfonyl)carbamate (1931 g, 3.42 mol) in portions over 10 minutes. The resulting mixture was stirred at room temperature for 1.5 h, the solvents removed in vacuo, and chased with dichloromethane (2 L). The resulting solid was treated a second time with fresh 98:2 trifluoroacetic acid:water (8.9 L), heated for 1 h at 40-50° C., the solvents removed in vacuo, and chased with dichloromethane (3×2 L). The resulting white solid was dried in a vacuum drying oven at 50° C. overnight. A total of 5409 g was processed in this manner (4990 g, quant. yield). LCMS for $C_{12}H_{12}BrFN_7O_5S$ $(M+H)^+$: m/z=463.9, 465.9. $^1H$ NMR (400 MHz, DMSO-$d_6$): δ 8.08 (dd, J=6.2, 2.5 Hz, 1H), 7.72 (m, 1H), 7.59 (t, J=8.7 Hz, 1H), 6.67 (t, J=5.9 Hz, 1H), 6.52 (t, J=6.0 Hz, 1H), 3.38 (dd, J=12.7, 6.3 Hz, 2H), 3.11 (dd, J=12.3, 6.3 Hz).

Method B: Using Hydrochloric Acid

To solution of tert-butyl ({[2-({4-[4-(3-bromo-4-fluorophenyl)-5-oxo-4,5-dihydro-1,2,4-oxadiazol-3-yl]-1,2,5-oxadiazol-3-yl}amino)ethyl]amino}sulfonyl)carbamate (4500 g) in isopropanol (9 L) was added 4 N HCl in dioxane (8.0 L). The reaction mixture was heated to 40-45° C. and was held at this temperature for about 5 h. Upon completion of reaction (as indicated by HPLC analysis), heptane (72 L) was added to the reaction mixture. The resultant mixture was heated to 68° C. and held at this temperature for 1 h. The batch was allowed to cool to about 23° C. The solid product was collected by filtration. The wet cake was washed with a mixture of heptane (16 L) and isopropanol (1.2 L) and dried under suction on a filter funnel. The crude product was dissolved in ethyl acetate (10.8 L) at about 43° C. Heptane (32.4 L) was added to the ethyl acetate solution over 15 min. The batch was heated to 70° C. and held at this temperature for 1 h. The batch was cooled to 21° C. and solid product was collected by filtration. The wet cake was washed with heptane (14.4 L) and dried under suction on the filter funnel. Yield of product was 3034 g. LC-MS, $^1H$ and $^{13}C$ NMR, and HPLC data of this lot were identical to those of the product prepared by Method A.

Step 7: (Z)-4-({2-[(Aminosulfonyl)amino]ethyl}amino)-N-(3-bromo-4-fluorophenyl)-N'-hydroxy-1,2,5-oxadiazole-3-carboximidamide

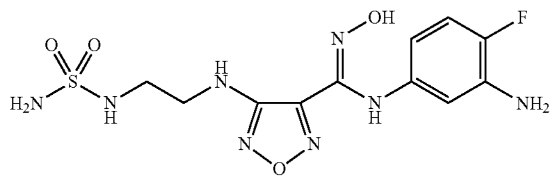 [SMILES: Nc1cc(N/C(=N\O)c2nonc2NCCNS(N)(=O)=O)ccc1F]

Method A:

To a crude mixture of N-[2-({4-[4-(3-bromo-4-fluorophenyl)-5-oxo-4,5-dihydro-1,2,4-oxadiazol-3-yl]-1,2,5-oxadiazol-3-yl}amino)ethyl]sulfamide (2.4 mol) containing residual amounts of trifluoroacetic acid stirring in a 22 L flask was added THE (5 L). The resulting solution was cooled to 0° C. using an ice bath and 2 N NaOH (4 L) was added at a rate so that the temperature did not exceed 10° C. After stirring at ambient temperature for 3 h (LCMS indicated no starting material remained), the pH was adjusted to 3-4 with concentrated HCl (~500 mL). The THF was removed in vacuo, and the resulting mixture was extracted with ethyl acetate (15 L). The organic layer was washed with water (5 L), brine (5 L), and the solvents removed in vacuo to afford a solid. The solid was triturated with MTBE (2×2 L), combined with three other reactions of the same size, and dried overnight in a convection oven to afford a white solid (3535 g). The solid was recrystallized (3×22 L flasks, 2:1 deionized ultra-filtered water:ethanol, 14.1 L each flask) and dried in a 50° C. convection oven to a constant weight to furnish the title compound as an off-white solid (3290 g, 78%). LCMS for $C_{11}H_{14}BrFN_7O_4S$ $(M+H)^+$: m/z=437.9, 439.9. $^1H$ NMR (400 MHz, DMSO-$d_6$): δ 11.51 (s, 1H), 8.90 (s, 1H), 7.17 (t, J=8.8 Hz, 1H), 7.11 (dd, J=6.1, 2.7 Hz, 1H), 6.76 (m, 1H), 6.71 (t, J=6.0 Hz, 1H), 6.59 (s, 2H), 6.23 (t, J=6.1 Hz, 1H), 3.35 (dd, J=10.9, 7.0 Hz, 2H), 3.10 (dd, J=12.1, 6.2 Hz, 2H). X-ray crystallographic analysis determined that the title compound adopts a Z-configuration (Z-isomer) with respect to the carbon-nitrogen double bond (C═N) of oxime functionality.

Method B:

N-[2-({4-[4-(3-bromo-4-fluorophenyl)-5-oxo-4,5-dihydro-1,2,4-oxadiazol-3-yl]-1,2,5-oxadiazol-3-yl}amino)ethyl]sulfamide (1500 g) was added to THF (6.0 L) and the batch was cooled to 2° C. Trifluoroacetic acid (0.006 L) was added to the batch at 2° C. followed by addition of aqueous sodium hydroxide solution (384 g of solid NaOH in 4.8 L of water) at 0-2° C. The batch was warmed up to about 16° C. and held for 5 h. Upon completion of reaction, as indicated by HPLC, concentrated hydrochloric acid (0.7 L) was added to adjust the pH of the batch to 3-4. About 4 L of solvent was removed from the batch by distillation under reduced pressure. The batch was added to ethyl acetate (18.0 L) and the biphasic mixture was stirred for 15 min. The organic layer was washed with water (6.0 L) and brine (6.0 L) sequentially. The organic solution was dried over anhydrous magnesium sulfate. Magnesium sulfate was filtered and the filtrate was evaporated to dryness under reduced pressure. To the resultant solid, MTBE (3.0 L) was added and the slurry was stirred for 15 min. The solid product was isolated by filtration. The filter cake was washed with MTBE (1.2 L) and heptane (1.2 L) sequentially. The solid was dried on the filter funnel under suction to give 1416 g (87.9%) of the product. The product (2440 g, obtained in two batches) was further purified by re-slurrying in MTBE (9.6 L) at 17° C. for 2 h. The batch was cooled to 6° C. for 30 min. The solid product was collected by filtration and the wet cake was washed with MTBE (3.6 L) and heptane (1.2 L) sequentially. The product was dried in a vacuum oven at 20° C. to give 1962 g of the title compound in 81.7% yield. LC-MS, $^1H$ and $^{13}C$ NMR, and HPLC data of this lot were identical to those of the product prepared by Method A.

Example 24

4-(2-[(Aminosulfonyl)(methyl)amino]ethylamino)-N-(3-chloro-4-fluorophenyl)-N'-hydroxy-1,2,5-oxadiazole-3-carboximidamide

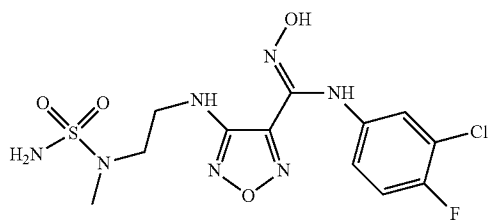 [SMILES: CN(CCNc1nonc1/C(=N/O)Nc1ccc(F)c(Cl)c1)S(N)(=O)=O]

Step 1. (4-Methoxybenzyl)methylamine

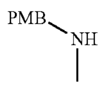

40% Aqueous methylamine (160 mL, 2.40 mol) was added to a solution of 4-methoxybenzaldehyde (164 g, 1.20 mol) in MeOH (600 mL). The mixture was diluted with additional MeOH (600 mL) and placed in a water bath. $NaBH_4$ (24.0 g, 0.63 mol) was added in 1 g portions over 2 h. Ice was added periodically to the water bath to maintain the reaction temperature at 15-20° C. throughout the addition of $NaBH_4$. The reaction mixture was stirred 0.5. The mixture was cooled to 5° C. and adjusted to pH 1 by the cautious addition of 6N HCl (680 mL). MeOH was removed under reduced pressure and the aqueous residue was extracted with EtOAc (500 mL). The EtOAc phase was back extracted with 1N HCl (200 mL). The combined acidic solution was cooled in an ice-bath and made basic (pH 11-12) with 24% w/v NaOH until all solids that initially form dissolved. The aqueous mixture was extracted with EtOAc (4×400 mL). The combined EtOAc extracts were dried over $Na_2SO_4$, filtered and the solution concentrated under reduced pressure. The residual liquid was distilled to give 150 g of (4-methoxybenzyl)methylamine (bp 79-88°, 1.0 Torr).

Step 2. [(4-Methoxybenzyl)methylamino]acetonitrile

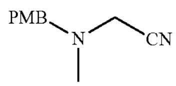

A solution of (4-methoxybenzyl)methylamine (125 g, 0.828 mol), chloroacetonitrile (75 g, 0.993 mol, 1.20 equiv) and N,N-diisopropylethylamine (134 g, 1.035 mol) in toluene (600 mL) was refluxed for 1 h. The mixture was cooled to room temperature and diluted with EtOAc (1.5 L). The solution was washed with $H_2O$ (3×750 mL), brine, dried over $Na_2SO_4$, filtered and the solution concentrated under reduced pressure. The residual liquid was distilled to give 152 g (97%) of [(4-methoxybenzyl)methylamino]acetonitrile (bp 128-135°, 2.0 Torr).

Step 3. $N^1$-4-methoxybenzyl-$N^1$-methylethanediamine

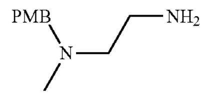

1M $LiAlH_4$ in THE (1.10 L, 1.10 mol) was added to THE (1 L) and the solution cooled to −20° C. A solution of [(4-methoxybenzyl)methylamino]acetonitrile (140 g, 0.737 mol) in THF (500 mL) was added over 1 h while maintaining the reaction temperature at <−10° C. The mixture was allowed to warm to room temperature and stirred 1 h. The mixture was cooled to −10° C. and a solution of sodium potassium tartrate (37% w/v, 200 mL) was added dropwise cautiously while maintaining reaction temperature at <0° C. Celite (50 g) was added and the mixture filtered through a pad of Celite, washing the solids with THE (300 mL) followed by MTBE (300 mL). The filtrate was dried over $Na_2SO_4$, filtered and the solution concentrated under reduced pressure. The residual liquid was Kugelrohr distilled to give 114 g (80%) of $N^1$-4-methoxybenzyl-$N^1$-methylethanediamine (oven temperature 128-135°, 1.0 Torr).

Step 4. 4-Amino-N'-hydroxy-N-{2-[(4-methoxybenzyl)methyl)amino]ethyl}-1,2-5-oxadiazole-3-carboximidamide

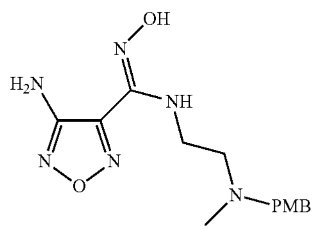

A solution of $N^1$-4-methoxybenzyl-$N^1$-methylethanediamine (17.7 g, 0.109 mol) in THE (50 mL) and EtOAc (200 mL) was added over 0.5 h at >25° C. (mild cooling required) to a solution of 5 (21.2 g, 0.109 mol) and $Et_3N$ (12.7 g, 17.5 ml, 0.126 mol) in EtOAc (500 mL). The pale yellow suspension was stirred at room temperature for 1 hr. The mixture was filtered and the solids were washed with EtOAc (200 mL). The filtrate was washed with $H_2O$ (3×400 mL), brine (400 mL), dried over $Na_2SO_4$, filtered and the solution concentrated under reduced pressure to ~300 mL volume. Heptane (300 mL) was added and the solution concentrated under reduced pressure until a slight turbidity developed. The mixture was stirred until crystallization was complete (~1 h) and then concentrated to near dryness. The solid was triturated with heptane, filtered and dried to give 32.6 g (93%) of 4-amino-N'-hydroxy-N-{2-[(4-methoxybenzyl) methyl)amino]ethyl}-1,2-5-oxadiazole-3-carboximidamide as an off-white solid.

Step 5. N'-hydroxy-4-({2-[(4-methoxybenzyl)(methyl)amino]ethyl}amino)-1,2-5-oxadiazole-3-carboximidamide

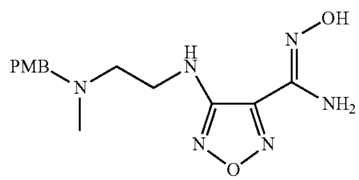

KOH (34.0 g, 0.607 mol) was added to a suspension of 4-amino-N'-hydroxy-N-{2-[(4-methoxybenzyl)methyl)amino]ethyl}-1,2-5-oxadiazole-3-carboximidamide (77.7 g, 0.243 mol) in ethylene glycol (500 mL) and the mixture heated to −135° C. After 2 h at −135° C. the mixture was cooled to room temperature and stirred overnight. The mixture was diluted with $H_2O$ (1.5 L) and extracted with MTBE (3×750 mL, 2×500 mL). The combined organic solution was washed with $H_2O$ (4×750 mL), brine (750 mL), dried over $Na_2SO_4$, filtered and the solution concentrated under reduced pressure to near dryness. The red-maroon viscous oil was dissolved in 50% MTBE/heptane (500 mL) with slight warming, seeded and the mixture stirred ~0.5 h. The suspension was concentrated to ~2 volume, filtered and the solids washed with 10% MTBE/heptane (350 mL) and dried to give 68.1 g (88%) of N'-hydroxy-4-({2-[(4-methoxybenzyl)(methyl)amino]ethyl}amino)-1,2-5-oxadiazole-3-carboximidamide as a light pinkish-white solid.

Step 6. N-Hydroxy-4-(2-[(4-methoxybenzyl)(methyl)amino]ethylamino)-1,2-5-oxadiazole-3-carboximidoyl chloride hydrochloride

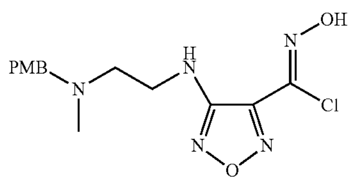

A mixture of N'-hydroxy-4-({2-[(4-methoxybenzyl)(methyl)amino]ethyl}amino)-1,2-5-oxadiazole-3-carboximidamide (32.4 g, 0.101 mol), NaCl (17.6 g, 0.304 mol), HOAc (175 mL) and 6 N HCl (86 mL) was stirred at room temperature until all solids (except some NaCl) had dissolved and then cooled in an ice/brine bath. A solution of $NaNO_2$ (7.7 g, 0.111 mol) in $H_2O$ (40 mL) was added dropwise maintaining the reaction temperature at −2 to 2° C. When addition was complete the mixture was stirred at 0-3° with an extremely thick suspension forming after ~0.75 h. After 2 h the mixture was allowed to warm to room temperature and then it was concentrated under reduced pressure to give a pale yellow solid. Residual HOAc and $H_2O$ were co-evaporated with toluene (3×400 mL) and the solid was dried under high vacuum overnight. The crude mixture of N-hydroxy-4-(2-[(4-methoxybenzyl)(methyl)amino]ethylamino)-1,2-5-oxadiazole-3-carboximidoyl chloride hydrochloride and NaCl was used in the next reaction without further purification.

Step 7. N-(3-Chloro-4-fluorophenyl)-N'-hydroxy-4-(2-[(4-methoxybenzyl)-(methyl)amino]ethylamino)-1,2-5-oxadiazole-3-carboximidamide

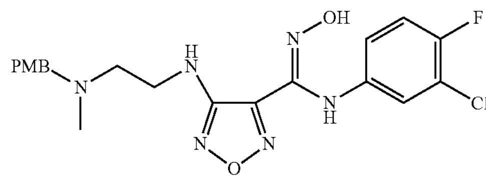

Crude N-Hydroxy-4-(2-[(4-methoxybenzyl)(methyl)amino]ethylamino)-1,2-5-oxadiazole-3-carboximidoyl chloride hydrochloride was suspended in EtOH (650 mL) and 3-chloro-4-fluoroaniline (12) (36.7 g, 0.253 mol) was added. The mixture was refluxed for 5 h and then cooled to room temperature. The mixture was concentrated under reduced pressure to remove EtOH. The residual oily solid was partitioned between EtOAc (1 L) and 12 saturated aqueous $NaHCO_3$ solution (300 mL). The organic phase was washed with brine (300 mL), dried over $Na_2SO_4$, filtered and the solution concentrated under reduced pressure. The resulting oily solid was triturated with 30% MTBE/heptane (700 mL), filtered, washed with 30% MTBE/heptane (300 mL) and dried to give 37.9 g (83% from N'-hydroxy-4-({2-[(4-methoxybenzyl)(methyl)amino]ethyl}amino)-1,2-5-oxadiazole-3-carboximidamide) of N-(3-chloro-4-fluorophenyl)-N'-hydroxy-4-(2-[(4-methoxybenzyl)-(methyl)amino]ethylamino)-1,2-5-oxadiazole-3-carboximidamide as a grayish-tan solid.

Step 8. 4-(3-Chloro-4-fluorophenyl)-3-[4-(2-[(4-methoxybenzyl)-(methyl)amino]-ethylamino)-1,2-5-oxadiazol-3-yl]-1,2,4-oxadiazol-5(4H)-one

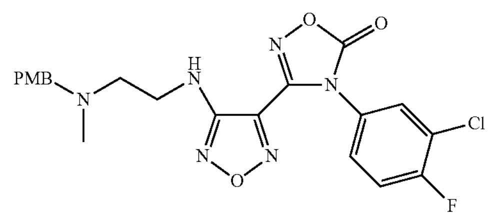

N,N-Carbonyldiimidazole (16.4 g, 101 mmol) was added to a solution of N-(3-chloro-4-fluorophenyl)-N'-hydroxy-4-(2-[(4-methoxybenzyl)-(methyl)amino]ethylamino)-1,2-5-oxadiazole-3-carboximidamide (37.9 g, 84.4 mmol) in THF (550 mL) and the mixture refluxed 1.75 h. The reaction mixture was cooled to room temperature and concentrated under reduced pressure. The resulting brown solid was dissolved in EtOAc (1 L) and the solution washed with $H_2O$ (3×500 mL), brine (300 mL), dried over $Na_2SO_4$, filtered and the solution concentrated under reduced pressure to ~300 mL. Heptane (400 mL) was added and the mixture was concentrated to a thick slurry. The slurry was diluted with heptane (400 mL) and concentrated to near dryness. The solid was slurried in heptane, filtered and dried to give 39.5 g (99%) of 4-(3-chloro-4-fluorophenyl)-3-[4-(2-[(4-methoxybenzyl)-(methyl)amino]-ethylamino)-1,2-5-oxadiazol-3-yl]-1,2,4-oxadiazol-5(4H)-one as a tan solid.

Step 9. 4-(3-Chloro-4-fluorophenyl)-3-[4-(2-(methyl)amino]ethylamino)-1,2-5-oxadiazol-3-yl]-1,2,4-oxadiazol-5(4H)-one hydrochloride

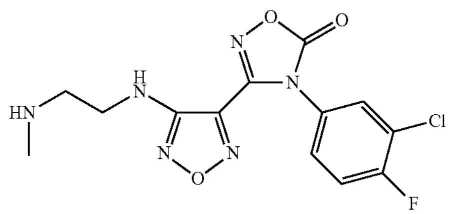 [SMILES: CNCCNc1nonc1-c1noc(=O)n1-c1ccc(F)c(Cl)c1]

A suspension of 4-(3-chloro-4-fluorophenyl)-3-[4-(2-[(4-methoxybenzyl)-(methyl)amino]-ethylamino)-1,2-5-oxadiazol-3-yl]-1,2,4-oxadiazol-5(4H)-one (39.3 g, 82.7 mmol) and $NaHCO_3$ (69.5 g, 827 mmol) in 1,2-dichloroethane (400 mL) was cooled to 0° C. and 1-chloroethyl chloroformate (26.6 g, 20.3 mL) was added dropwise at 0-2° C. The mixture was allowed to warm to room temperature, stirred 1.25 h then heated at 40-45° C. for 2.75 h. The mixture was cooled to room temperature, filtered, and the solids washed with DCM (500 mL). The filtrate was concentrated under reduced pressure giving a viscous brown oil. The oil was dissolved in MeOH (300 mL) and stirred overnight at room temperature. To ensure complete formation of amine hydrochloride salt, 4M HCl in dioxane (20 mL) was added and the mixture was concentrated under reduced pressure to give a viscous brown oil. The oil was dissolved in EtOAc (150 ml). After standing several minutes a precipitate began forming. When precipitation was complete the mixture was diluted with toluene (150 ml) and the solid was filtered. The solid was washed with 50% EtOAc/toluene (160 ml) and dried under $N_2$ to give 23.7 g (73%) of 4-(3-chloro-4-fluorophenyl)-3-[4-(2-(methyl)amino]ethylamino)-1,2-5-oxadiazol-3-yl]-1,2,4-oxadiazol-5(4H)-one hydrochloride as a tan solid that was used without further purification.

Step 10. 4-(3-Chloro-4-fluorophenyl)-3-{4-[(2-(aminosulfonyl)(methyl)amino]ethylamino)-1,2-5-oxadiazol-3-yl}-1,2,4-oxadiazol-5(4H)-one

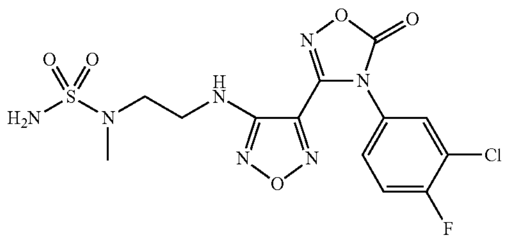 [SMILES: CN(CCNc1nonc1-c1noc(=O)n1-c1ccc(F)c(Cl)c1)S(N)(=O)=O]

A solution of crude 4-(3-chloro-4-fluorophenyl)-3-[4-(2-(methyl)amino]ethylamino)-1,2-5-oxadiazol-3-yl]-1,2,4-oxadiazol-5(4H)-one hydrochloride (23.7 g, ~60.8 mmol) and sulfamide (23.3 g, 243 mmol) in pyridine (275 mL) was heated at ~100° C. for 2.5 h. A light suspension formed at ~95° C. that developed into a gummy residue at the end of the reflux period. The mixture was cooled to room temperature, the pyridine solution decanted from the gummy residue, and the remaining pyridine was evaporated under reduced pressure. The residual brown oil was partitioned between EtOAc (500 mL) and 1N HCl (200 mL). The organic phase was washed sequentially with 1N HCl (2×200 mL), $H_2O$ (200 mL), and brine (200 mL), and then dried over $Na_2SO_4$, filtered and the solution concentrated under reduced pressure to give 31.1 g of crude 4-(3-chloro-4-fluorophenyl)-3-{4-[(2-(aminosulfonyl)(methyl)amino] ethyl-amino)-1,2-5-oxadiazol-3-yl}-1,2,4-oxadiazol-5(4H)-one as a viscous brown oil that solidified on standing overnight. The crude product was used without further purification.

Step 11. 4-(2-[(Aminosulfonyl)(methyl)amino]ethyl-amino)-N-(3-Chloro-4-fluorophenyl)-N'-hydroxy-1,2,5-oxadiazole-3-carboximidamide

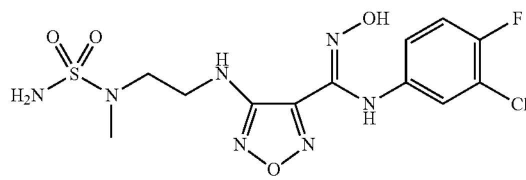 [SMILES: CN(CCNc1nonc1/C(=N/O)Nc1ccc(F)c(Cl)c1)S(N)(=O)=O]

10% aqueous NaOH (150 mL) was added slowly to a suspension of crude 4-(3-chloro-4-fluorophenyl)-3-{4-[(2-(aminosulfonyl)(methyl)amino]ethylamino)-1,2-5-oxadiazol-3-yl}-1,2,4-oxadiazol-5(4H)-one (53.3 g) in MeOH (500 mL). The reaction temperature increased from 19 to 29° C. A clear brown solution slowly developed followed by formation of a light suspension formed after ~0.25 h. After 0.75 h at room temperature the reaction was complete. The mixture was concentrated under reduced pressure to remove most of the MeOH and the aqueous residue was diluted with $H_2O$. The mixture was cooled in an ice-bath and adjusted to pH ~2 with conc HCl/ice to give a gummy oil. The mixture was extracted with EtOAc (1 L). The organic solution was washed with sat'd aqueous $NaHCO_3$ (500 mL), brine (500 mL), dried over $Na_2SO_4$, filtered and the solution concentrated under reduced pressure to give a viscous brown oil that partially solidified on standing several days. The crude product was redissolved in a minimal amount of EtOAc, absorbed on to silica gel and dry loaded on a column of silica gel packed in 33% EtOAc/heptane. The column was eluted with 33% EtOAc/heptane (3 L), 50% EtOAc/heptane (4 L), and 67% EtOAc/heptane (3 L). Product fractions were concentrated until a slight turbidity developed. The mixture was slowly concentrated to dryness to give an off-white solid. The solid was suspended in IPA (220 mL, 6 mL/g) and heated to ~75° C. (clear solution at ~30° C.). Heptane (550 mL, 15 mL/g) was added slowly via an addition funnel at 73-75° C. When addition was complete the solution was allowed to cool slowly. When a slight turbidity developed (~55° C.) the mixture was seeded. Solids began precipitating as the mixture slowly cooled. After cooling to room temperature the suspension was further cooled in an ice/brine bath and stirred at −4 to 0° for 3 h. The mixture was filtered, washing the solids with heptane (200 mL) then dried to give 31.0 g of 4-(2-[(aminosulfonyl)(methyl)amino]ethylamino)-N-(3-chloro-4-fluorophenyl)-N'-hydroxy-1,2,5-oxadiazole-3-carboximidamide as a white solid. $^1H$ NMR (400 MHz, DMSO-d6) δ 11.50 (s, 1H), 8.92 (s, 1H), 7.20 (dd, J=9.1 Hz, 1H), 6.98 (dd, J=6.5, 2.7 Hz, 1H), 6.76 (s, 2H), 6.73-6.68 (m, 1H), 6.23 (t, J=6.0 Hz, 1H), 3.42-3.36 (m, 2H), 3.12 (t, J=6.2

Hz, 2H), 2.66 (s, 3H). LCMS for $C_{12}H_{16}ClFN_7O_4S$ $(M+H)^+$: m/z=408.1; Found: 408.0. $IC_{50}$: 132 nM. This number is the average of five lots.

Compound Data

Human indoleamine 2,3-dioxygenasae (IDO) enzyme assay: Human indoleamine 2,3-dioxygenasae (IDO) with an N-terminal His tag was expressed in *E. coli* and purified to homogeneity. IDO catalyzes the oxidative cleavage of the pyrrole ring of the indole nucleus of tryptophan to yield N'-formylkynurenine. The assays were performed at room temperature as described in the literature using 95 nM IDO and 2 mM D-Trp in the presence of 20 mM ascorbate, 5 µM methylene blue and 0.2 mg/mL catalase in 50 mM potassium phosphate buffer (pH 6.5). The initial reaction rates were recorded by continuously following the absorbance increase at 321 nm due to the formation of N'-formlylkynurenine (See: Sono, M., et al., 1980, J. Biol. Chem. 255, 1339-1345).

Select physical and biological activity data for the compounds of Examples 1-19 are summarized in Table 4 below. $IC_{50}$ data are from the IDO enzyme assay described above.

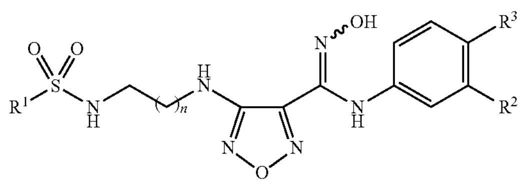

TABLE 4

| Ex. No. | $R_1$ | $R_2$ | $R_3$ | n | IDO $IC_{50}$ (nM) | MS [M + H] |
|---|---|---|---|---|---|---|
| 1 | $NH_2$ | Br | F | 1 | <200 | 437.9, 439.9 |
| 2 | Me | Br | F | 1 | <200 | 437.0, 439.0 |
| 3 | $NH_2$ | Br | F | 2 | <100 | 451.8, 453.9 |
| 4 | Me | Br | F | 2 | <100 | 451.0, 453.0 |
| 5 | $NH_2$ | Cl | F | 1 | <200 | 394.0 |
| 6 | Me | Cl | F | 1 | <200 | 393.0 |
| 7 | $NH_2$ | Cl | F | 2 | <200 | 408.1 |
| 8 | Me | Cl | F | 2 | <200 | 407.1 |
| 9 | $NH_2$ | $CF_3$ | F | 1 | <100 | 428.0 |
| 10 | Me | $CF_3$ | F | 1 | <100 | 427.0 |
| 11 | $NH_2$ | $CF_3$ | F | 2 | <100 | 442.0 |
| 12 | Me | $CF_3$ | F | 2 | <100 | 441.1 |
| 13 | $NH_2$ | $CF_3$ | H | 1 | <500 | 410.0 |
| 14 | Me | $CF_3$ | H | 1 | <200 | 409.1 |
| 15 | $NH_2$ | $CF_3$ | H | 2 | <200 | 424.0 |
| 16 | Me | $CF_3$ | H | 2 | <200 | 423.1 |
| 17 | Me | $CF_3$ | F | 1 | <500 | 373.1 |
| 18 | $NH_2$ | CN | F | 1 | <750 | 385.0 |
| 19 | Me | CN | F | 1 | <500 | 406.0* |

*[M + Na]

Compound Data

IDO $IC_{50}$ data for the compounds of Examples 20, 21, and 24 is provided below in Table 5.

TABLE 5

| Ex. No. | IDO $IC_{50}$ (nM) |
|---|---|
| 20 | <500 |
| 21 | <750 |
| 24 | <200 |

All of the compositions and/or methods disclosed and claimed herein can be made and executed without undue experimentation in light of the present disclosure. While the compositions and methods of this invention have been described in terms of some embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references and any others listed herein, to the extent that they provide exemplary procedural or other details supplementary to those set forth herein, are specifically incorporated herein by reference in their entirety.

WO 99/29310
WO 03/087347
WO 2004/094409
U.S. 2004/0234623
U.S. 2006/0258719
U.S. 2007/0185165
U.S. Pat. No. 6,682,736
U.S. Pat. No. 6,984,720
U.S. Pat. No. 7,034,121
U.S. Pat. No. 7,109,003
U.S. Pat. No. 7,132,281
U.S. Pat. No. 7,229,628
U.S. Pat. No. 7,307,064
U.S. Pat. No. 7,311,910
U.S. Pat. No. 8,088,803
U.S. patent Ser. No. 12/498,782
Blank et al., *Cancer Res.,* 64:1140-1145, 2004.
Brown et al., *J Immunol.* 177:4521-4529, 2006.
Daubener, et al., *Adv. Exp. Med. Biol.,* 467: 517-24, 1999.
Elpek et al., *The Journal of Immunology,* 178: 6840-6848, 2007.
Gajewski et al., *Cancer J.,* 16:399-403, 2010.
Gajewski et al., *Immunol. Rev.,* 213:131-145, 2006.
Grohmann, et al., *Trends Immunol.,* 24: 242-8, 2003.
Harlin et al., *Cancer Immunol. Immunother.,* 55:1185-1197, 2006.
Harlin et al., *Cancer Res.,* 69(7):3077-85, 2009.
Kline et al., *Clin. Cancer Res.* 14:3156-3167, 2008.
Logan, et al., *Immunology,* 105: 478-87, 2002.
Muller et al., *Nature Med.,* 11: 312-9, 2005.
Munn, et al., *Curr Pharm Des,* 9(3):257-64, 2003.
Munn, et al., *J Exp Med,* 189(9):1363-72, 1999.
Munn, et al., *J. Clin. Invest.,* 114(2): 280-90, 2004.
Munn, et al., *Science,* 297: 1867-70, 2002.
Posner et al., *Hybridoma,* 6(6):611-25, 1987
Quezada et al., *J CHn Invest.,* 116: 1935-1945, 2006.

Taylor, et al., *FASEB J.,* 5: 2516-22, 1991.
Uyttenhove et al., *Nature Med.,* 9: 1269-74, 2003.
Wermuth, et al., *Handbook of Pharmaceutical Salts: Properties, and Use*. Switzerland: Verlag Helvetica Chimica Acta, 2002.
Wirleitner, et al., *Curr. Med. Chem.,* 10: 1581-91, 2003.
Zha et al., *Nat. Immunol.* 7:1166-1173, 2006.
Zhang et al., *Blood,* 114:1545-1552, 2009.

The invention claimed is:

1. A method of treating cancer in a subject comprising administering to the subject a therapeutically effective amount of an inhibitor of CTLA-4 and one of: an inhibitor of indoleamine-2,3-dioxygenase (IDO) or an inhibitor of the PD-L1/PD-1 pathway, wherein the CTLA-4 inhibitor comprises ipilimumab; tremelimumab or UC10-4F10-11; and wherein the IDO inhibitor is:

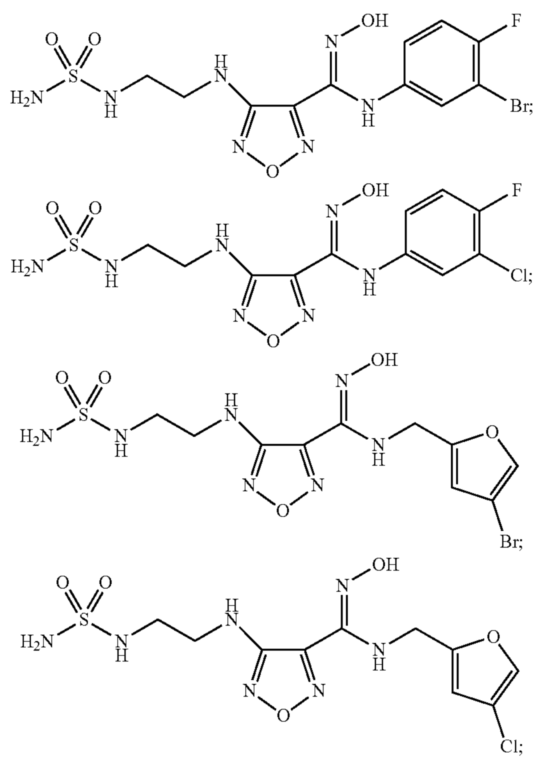

or a combination thereof.

2. The method of claim 1, wherein the method comprises administering the inhibitor of IDO and the inhibitor of CTLA-4.

3. The method of claim 1, wherein the method comprises administering the inhibitor of the PD-L1/PD-1 pathway and the inhibitor of CTLA-4.

4. The method of claim 1, wherein the inhibitor of the PD-L1/PD-1 pathway is an anti-PD-L1 antibody or an anti-PD-1 antibody.

5. The method of claim 4, wherein the anti-PD-L1 antibody is BMS-936559, MPDL3280A, BMS-936558, MK-3475, CT-011, or MEDI4736.

6. The method of claim 1, wherein the anti-CTLA-4 inhibitor is ipilimumab.

7. The method of claim 1, wherein treating cancer is further defined as reducing the size of a tumor of the cancer or inhibiting growth of a tumor of the cancer.

8. The method of claim 1, wherein the cancer is melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplastic syndrome, multiple myeloma, transitional cell carcinoma, neuroblastoma, plasma cell neoplasms, Wilm's tumor, or hepatocellular carcinoma.

9. The method of claim 8, wherein the cancer is melanoma.

10. The method of claim 1, wherein the inhibitor of CTLA-4 and the one of the inhibitor of indoleamine-2,3-dioxygenase (IDO) or the inhibitor of the PD-L1/PD-1 pathway are administered to the subject at least two, three, four, five, six, seven, eight, nine or ten times.

11. The method of claim 1, wherein said subject is further administered a distinct cancer therapy.

12. The method of claim 11, wherein said distinct cancer therapy comprises surgery, radiotherapy, chemotherapy, toxin therapy, immunotherapy, cryotherapy or gene therapy.

13. The method of claim 1, wherein the cancer is a chemotherapy-resistant or radio-resistant cancer.

14. The method of claim 1, wherein the subject is administered at least 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 150, 200, 250, or 300 mg/kg of the CTLA-4 inhibitor and the one of the IDO inhibitor or the PD-L1/PD-1 inhibitor.

15. The method of claim 1, wherein the CTLA-4 inhibitor is ipilimumab and the IDO inhibitor is

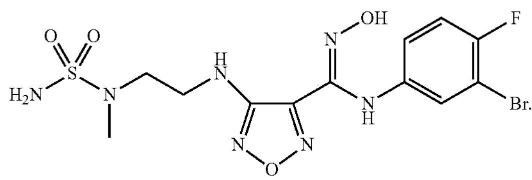 [SMILES: CN(CCNc1nonc1/C(=N/O)Nc1ccc(F)c(Br)c1)S(N)(=O)=O]

16. The method of claim 8, wherein the CTLA-4 inhibitor is ipilimumab and the IDO inhibitor is

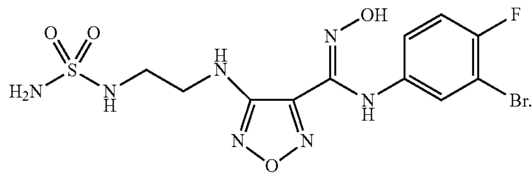 [SMILES: NS(=O)(=O)NCCNc1nonc1/C(=N/O)Nc1ccc(F)c(Br)c1]

17. The method of claim 2, further comprising administering to the subject a therapeutically effective amount of an inhibitor of the PD-L1/PD-1 pathway.

18. The method of claim 3, further comprising administering to the subject a therapeutically effective amount of an inhibitor of IDO, wherein the inhibitor of IDO inhibitor is:

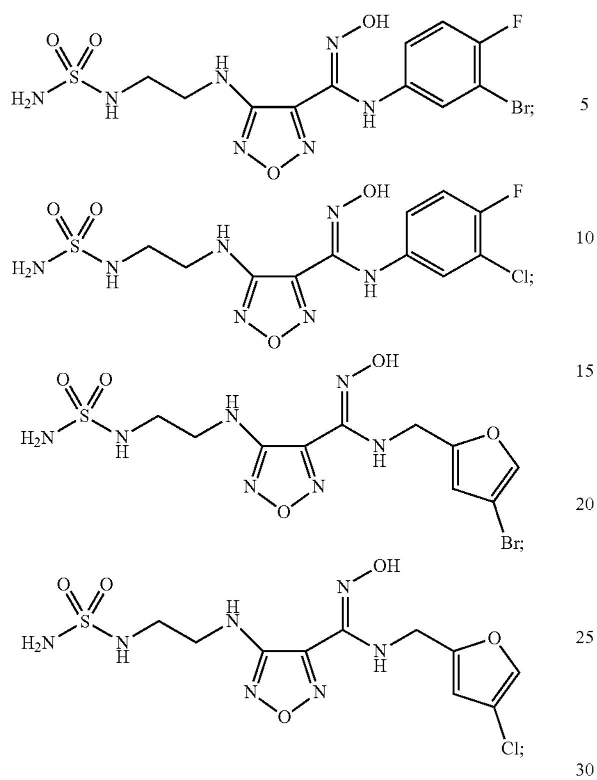
or a combination thereof.
* * * * *